(12) United States Patent
Sharma

(10) Patent No.: US 11,351,050 B2
(45) Date of Patent: Jun. 7, 2022

(54) INTRAGASTRIC DEVICE FOR TREATING OBESITY

(71) Applicant: SynerZ Medical, Inc., Newark, DE (US)

(72) Inventor: Virender K. Sharma, Paradise Valley, AZ (US)

(73) Assignee: SynerZ Medical, Inc., Newark, DE (US)

( * ) Notice: Subject to any disclaimer, the term of this patent is extended or adjusted under 35 U.S.C. 154(b) by 312 days.

(21) Appl. No.: 16/540,691

(22) Filed: Aug. 14, 2019

(65) Prior Publication Data
US 2019/0365552 A1 Dec. 5, 2019

Related U.S. Application Data

(63) Continuation of application No. 14/096,505, filed on Dec. 4, 2013, now Pat. No. 10,413,436, which is a (Continued)

(51) Int. Cl.
*A61F 5/00* (2006.01)
*A61F 2/04* (2013.01)
*A61F 2/915* (2013.01)

(52) U.S. Cl.
CPC .......... *A61F 5/0013* (2013.01); *A61F 5/0036* (2013.01); *A61F 5/0089* (2013.01); (Continued)

(58) Field of Classification Search
CPC ................. A61F 5/0013; A61F 5/0036; A61F 2002/9155; A61F 2220/0016; A61F 2230/0071
See application file for complete search history.

(56) References Cited

U.S. PATENT DOCUMENTS 1,899,781 A   2/1933 Twiss
2,464,933 A   3/1949 Kaslow
(Continued)

FOREIGN PATENT DOCUMENTS

AU   2010271294 A1   2/2012
AU   2011203951 A1   7/2012
(Continued)

OTHER PUBLICATIONS

US 8,668,662 B2, 03/2014, Levine (withdrawn)
(Continued)

*Primary Examiner* — Richard G Louis

(57) ABSTRACT

The present invention is directed toward an intragastric device used to treat obesity that includes a wire mesh structure capable of changing from a compressed pre-deployment shape to an expanded post-deployment shape with a greatly increased volume. The post-deployment shape contains a light weight at the top and a heavier weight at the bottom to ensure proper positioning within the stomach. In the post-deployment shape, the device contains larger spaces in the upper portion and smaller spaces in the lower portion to sequester food and delay gastric emptying. Alternatively, the device can be enveloped by a membrane containing larger holes at the top and smaller holes at the bottom to sequester food and delay gastric emptying. The device has a dynamic weight where the weight of the device in the pre-feeding stage is less than the weight of the device in feeding or post-feeding stage.

19 Claims, 26 Drawing Sheets

Related U.S. Application Data continuation of application No. 12/814,481, filed on Jun. 13, 2010, now Pat. No. 8,628,554.

(52) U.S. Cl.
CPC . *A61F 2002/045* (2013.01); *A61F 2002/9155* (2013.01); *A61F 2220/0016* (2013.01); *A61F 2230/0071* (2013.01)

(56) References Cited

U.S. PATENT DOCUMENTS

| | | |
|---|---|---|
| 3,780,740 A | 12/1973 | Rhea |
| 4,133,315 A | 1/1979 | Berman et al. |
| 4,134,405 A | 1/1979 | Smit |
| 4,246,893 A | 1/1981 | Berson |
| 4,270,542 A | 6/1981 | Plumley |
| 4,279,251 A | 7/1981 | Ruesch |
| 4,315,509 A | 2/1982 | Smit |
| 4,403,604 A | 9/1983 | Wilkinson et al. |
| 4,416,267 A | 11/1983 | Garren et al. |
| 4,441,215 A | 4/1984 | Kaster |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,738,667 A | 4/1988 | Galloway |
| 4,763,653 A | 8/1988 | Rockey |
| 4,767,627 A | 8/1988 | Caldwell et al. |
| 4,823,808 A | 4/1989 | Clegg et al. |
| 4,846,836 A | 7/1989 | Reich |
| 4,878,905 A | 11/1989 | Blass |
| 4,899,747 A | 2/1990 | Garren et al. |
| 4,913,141 A | 4/1990 | Hillstead |
| 5,035,706 A | 7/1991 | Giantureo et al. |
| 5,037,387 A | 8/1991 | Quinn et al. |
| 5,041,126 A | 8/1991 | Gianturco |
| 5,057,091 A | 10/1991 | Andersen |
| 5,104,399 A | 4/1992 | Lazarus |
| 5,152,756 A | 10/1992 | Quinn et al. |
| 5,163,952 A | 11/1992 | Froix |
| 5,188,104 A | 2/1993 | Wernicke et al. |
| 5,211,658 A | 5/1993 | Clouse |
| 5,234,454 A | 8/1993 | Bangs |
| 5,236,423 A | 8/1993 | Mix et al. |
| 5,246,456 A | 9/1993 | Wilkinson |
| 5,259,399 A | 11/1993 | Brown |
| 5,279,553 A | 1/1994 | Winkler et al. |
| 5,282,824 A | 2/1994 | Gianturco |
| 5,290,217 A | 3/1994 | Campos |
| 5,306,300 A | 4/1994 | Berry |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,327,914 A | 7/1994 | Shlain |
| 5,345,949 A | 9/1994 | Shlain |
| 5,364,353 A | 11/1994 | Corfitsen et al. |
| 5,387,235 A | 2/1995 | Chuter |
| 5,401,241 A | 3/1995 | Delany |
| 5,405,377 A | 4/1995 | Cragg |
| 5,405,378 A | 4/1995 | Strecker |
| 5,423,872 A | 6/1995 | Cigaina |
| 5,432,872 A | 7/1995 | Stewart et al. |
| 5,443,498 A | 8/1995 | Fontaine |
| 5,456,713 A | 10/1995 | Chuter |
| 5,480,423 A | 1/1996 | Ravenscroft et al. |
| 5,507,767 A | 4/1996 | Maeda et al. |
| 5,507,771 A | 4/1996 | Gianturco |
| 5,514,176 A | 5/1996 | Bosley, Jr. |
| 5,536,274 A | 7/1996 | Neuss |
| 5,562,697 A | 10/1996 | Christiansen |
| 5,569,219 A | 10/1996 | Hakki et al. |
| 5,593,434 A | 1/1997 | Williams |
| 5,611,787 A | 3/1997 | Demeter et al. |
| 5,624,430 A | 4/1997 | Eton et al. |
| 5,630,797 A | 5/1997 | Diedrich et al. |
| 5,637,699 A | 6/1997 | Dorn et al. |
| 5,653,743 A | 8/1997 | Martin |
| 5,658,322 A | 8/1997 | Fleming |
| 5,662,713 A | 9/1997 | Andersen et al. |
| 5,665,064 A | 9/1997 | Bodicky et al. |
| 5,668,263 A | 9/1997 | Hoyer et al. |
| 5,674,241 A | 10/1997 | Bley et al. |
| 5,690,692 A | 11/1997 | Fleming |
| 5,693,084 A | 12/1997 | Chuter |
| 5,700,272 A | 12/1997 | Gordon et al. |
| 5,709,657 A | 1/1998 | Zimmon |
| 5,713,910 A | 2/1998 | Gordon et al. |
| 5,715,832 A | 2/1998 | Koblish et al. |
| 5,720,776 A | 2/1998 | Chuter et al. |
| 5,733,325 A | 3/1998 | Robinson et al. |
| 5,741,277 A | 4/1998 | Gordon et al. |
| 5,741,279 A | 4/1998 | Gordon et al. |
| 5,749,918 A | 5/1998 | Hogendijk et al. |
| 5,755,777 A | 5/1998 | Chuter |
| 5,771,903 A | 6/1998 | Jakobsson et al. |
| 5,800,456 A | 9/1998 | Maeda et al. |
| 5,800,526 A | 9/1998 | Anderson et al. |
| 5,817,466 A | 10/1998 | Hoyer et al. |
| 5,820,584 A | 10/1998 | Crabb |
| 5,830,229 A | 11/1998 | Konya et al. |
| 5,835,897 A | 11/1998 | Jang |
| 5,843,164 A | 12/1998 | Frantzen et al. |
| 5,861,036 A | 1/1999 | Godin |
| 5,868,141 A | 2/1999 | Ellias |
| 5,876,445 A | 3/1999 | Andersen et al. |
| 5,887,594 A | 3/1999 | Locicero, III |
| 5,891,845 A | 4/1999 | Myers |
| 5,922,019 A | 7/1999 | Hankh et al. |
| 5,955,579 A | 9/1999 | Leonard et al. |
| 5,965,396 A | 10/1999 | Pan et al. |
| 5,993,483 A | 11/1999 | Gianotti |
| 6,027,508 A | 2/2000 | Ren et al. |
| 6,048,351 A | 4/2000 | Gordon et al. |
| 6,087,129 A | 7/2000 | Newgard et al. |
| 6,099,552 A | 8/2000 | Adams |
| 6,102,922 A | 8/2000 | Jakobsson et al. |
| 6,113,609 A | 9/2000 | Adams |
| 6,117,911 A | 9/2000 | Grainger et al. |
| 6,132,471 A | 10/2000 | Johlin, Jr. |
| 6,146,416 A | 11/2000 | Andersen et al. |
| 6,159,238 A | 12/2000 | Killion et al. |
| 6,180,082 B1 | 1/2001 | Woltering et al. |
| 6,183,461 B1 | 2/2001 | Matsuura et al. |
| 6,184,254 B1 | 2/2001 | Bukoski et al. |
| 6,200,336 B1 | 3/2001 | Pavcnik et al. |
| 6,200,600 B1 | 3/2001 | Rashid |
| 6,241,738 B1 | 6/2001 | Dereume |
| 6,245,761 B1 | 6/2001 | Britton et al. |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,302,891 B1 | 10/2001 | Nadal |
| 6,302,917 B1 | 10/2001 | Dua et al. |
| 6,303,637 B1 | 10/2001 | Bao et al. |
| 6,322,538 B1 | 11/2001 | Elbert et al. |
| 6,331,190 B1 | 12/2001 | Shokoohi et al. |
| 6,332,877 B1 | 12/2001 | Michels |
| 6,364,868 B1 | 4/2002 | Ikeguchi |
| 6,370,511 B1 | 4/2002 | Dang |
| 6,387,114 B2 | 5/2002 | Adams |
| 6,406,840 B1 | 6/2002 | Li et al. |
| 6,410,587 B1 | 6/2002 | Grainger et al. |
| 6,424,864 B1 | 7/2002 | Matsuura |
| 6,450,989 B2 | 9/2002 | Dubrul et al. |
| 6,454,785 B2 | 9/2002 | De Hoyos Garza |
| 6,485,409 B1 | 11/2002 | Voloshin et al. |
| 6,494,888 B1 | 12/2002 | Laufer et al. |
| 6,503,264 B1 | 1/2003 | Birk |

(56) References Cited

U.S. PATENT DOCUMENTS

| | | |
|---|---|---|
| 6,508,833 B2 | 1/2003 | Pavcnik et al. |
| 6,524,335 B1 | 2/2003 | Hartley et al. |
| 6,524,336 B1 | 2/2003 | Papazolgou et al. |
| 6,530,951 B1 | 3/2003 | Bates et al. |
| 6,531,491 B1 | 3/2003 | Kania et al. |
| 6,534,524 B1 | 3/2003 | Kania et al. |
| 6,537,247 B2 | 3/2003 | Shannon |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor |
| 6,565,597 B1 | 5/2003 | Fearnot et al. |
| 6,571,127 B1 | 5/2003 | Ben-Haim et al. |
| 6,572,627 B2 | 6/2003 | Gabbay |
| 6,572,629 B2 | 6/2003 | Kalloo et al. |
| 6,575,896 B2 | 6/2003 | Silverman et al. |
| 6,589,213 B2 | 7/2003 | Reydel |
| 6,589,275 B1 | 7/2003 | Ivancev et al. |
| 6,596,023 B1 | 7/2003 | Nunez et al. |
| 6,623,518 B2 | 9/2003 | Thompson et al. |
| 6,630,123 B1 | 10/2003 | Woltering et al. |
| 6,635,079 B2 | 10/2003 | Unsworth et al. |
| 6,656,194 B1 | 12/2003 | Gannoe et al. |
| 6,663,639 B1 | 12/2003 | Laufer et al. |
| 6,666,848 B2 | 12/2003 | Stone |
| 6,675,809 B2 | 1/2004 | Stack et al. |
| 6,676,692 B2 | 1/2004 | Rabkin et al. |
| 6,685,962 B2 | 2/2004 | Friedman et al. |
| 6,695,875 B2 | 2/2004 | Stelter et al. |
| 6,696,575 B2 | 2/2004 | Schmidt et al. |
| 6,699,263 B2 | 3/2004 | Cope |
| 6,733,512 B2 | 5/2004 | McGhan |
| 6,734,208 B2 | 5/2004 | Grainger et al. |
| 6,740,121 B2 | 5/2004 | Geitz |
| 6,743,198 B1 | 6/2004 | Tihon |
| 6,755,869 B2 | 6/2004 | Geitz |
| 6,761,733 B2 | 7/2004 | Chobotov et al. |
| 6,764,518 B2 | 7/2004 | Godin |
| 6,773,440 B2 | 8/2004 | Gannoe et al. |
| 6,773,441 B1 | 8/2004 | Laufer et al. |
| 6,776,791 B1 | 8/2004 | Stallings et al. |
| 6,776,999 B1 | 8/2004 | Krumme |
| 6,802,846 B2 | 10/2004 | Hauschild et al. |
| 6,802,868 B2 | 10/2004 | Silverman et al. |
| 6,844,349 B2 | 1/2005 | Kath et al. |
| 6,845,776 B2 | 1/2005 | Stack et al. |
| 6,855,153 B2 | 2/2005 | Saadat |
| 6,884,890 B2 | 4/2005 | Kania et al. |
| 6,890,924 B2 | 5/2005 | Kath et al. |
| 6,891,044 B2 | 5/2005 | Kania et al. |
| 6,911,198 B2 | 6/2005 | Shachar et al. |
| 6,932,838 B2 | 8/2005 | Schwartz et al. |
| 6,939,370 B2 | 9/2005 | Hartley et al. |
| 6,947,792 B2 | 9/2005 | Ben-Haim et al. |
| 6,950,707 B2 | 9/2005 | Whitehurst |
| 6,994,095 B2 | 2/2006 | Burnett |
| 7,019,147 B1 | 3/2006 | Barth et al. |
| 7,025,791 B2 | 4/2006 | Levine et al. |
| 7,033,373 B2 | 4/2006 | De et al. |
| 7,033,384 B2 | 4/2006 | Gannoe et al. |
| 7,037,344 B2 | 5/2006 | Kagan et al. |
| 7,041,120 B2 | 5/2006 | Li et al. |
| 7,044,979 B2 | 5/2006 | Silverman et al. |
| 7,056,305 B2 | 6/2006 | Garza Alvarez |
| 7,060,080 B2 | 6/2006 | Bachmann |
| 7,063,860 B2 | 6/2006 | Chancellor et al. |
| 7,066,945 B2 | 6/2006 | Hashiba et al. |
| 7,071,337 B2 | 7/2006 | Kath et al. |
| 7,083,629 B2 | 8/2006 | Weller et al. |
| 7,084,171 B2 | 8/2006 | Grainger et al. |
| 7,090,699 B2 | 8/2006 | Geitz |
| 7,097,665 B2 | 8/2006 | Stack et al. |
| 7,111,627 B2 | 9/2006 | Stack et al. |
| 7,120,497 B2 | 10/2006 | Ben-Haim et al. |
| 7,121,283 B2 | 10/2006 | Stack et al. |
| 7,122,058 B2 | 10/2006 | Levine et al. |
| 7,128,750 B1 | 10/2006 | Stergiopulos |
| 7,141,581 B2 | 11/2006 | Bender et al. |
| 7,141,587 B2 | 11/2006 | Kania et al. |
| 7,145,008 B2 | 12/2006 | Kath et al. |
| 7,146,984 B2 | 12/2006 | Stack et al. |
| 7,148,380 B2 | 12/2006 | Wang et al. |
| 7,152,607 B2 | 12/2006 | Stack et al. |
| 7,153,314 B2 | 12/2006 | Laufer et al. |
| 7,172,613 B2 | 2/2007 | Wazne |
| 7,189,750 B2 | 3/2007 | Assaf et al. |
| 7,196,093 B2 | 3/2007 | Yuan |
| 7,208,499 B2 | 4/2007 | Kath et al. |
| 7,211,114 B2 | 5/2007 | Bessler et al. |
| 7,220,284 B2 | 5/2007 | Kagan et al. |
| 7,221,978 B2 | 5/2007 | Ben-Haim et al. |
| 7,230,098 B2 | 6/2007 | Cui et al. |
| 7,235,562 B2 | 6/2007 | Kath et al. |
| 7,238,191 B2 | 7/2007 | Bachmann |
| 7,267,694 B2 | 9/2007 | Levine et al. |
| 7,271,262 B2 | 9/2007 | La et al. |
| 7,273,451 B2 | 9/2007 | Sekine et al. |
| 7,288,099 B2 | 10/2007 | Deem et al. |
| 7,288,101 B2 | 10/2007 | Deem et al. |
| 7,306,614 B2 | 12/2007 | Weller et al. |
| 7,309,858 B2 | 12/2007 | Pappin et al. |
| 7,314,443 B2 | 1/2008 | Jordan et al. |
| 7,316,716 B2 | 1/2008 | Egan |
| 7,320,696 B2 | 1/2008 | Gazi et al. |
| 7,329,285 B2 | 2/2008 | Levine et al. |
| 7,330,747 B2 | 2/2008 | Maier |
| 7,330,753 B2 | 2/2008 | Policker et al. |
| 7,332,493 B2 | 2/2008 | Kath et al. |
| 7,332,513 B2 | 2/2008 | Assaf et al. |
| 7,335,210 B2 | 2/2008 | Smit |
| 7,335,646 B2 | 2/2008 | Kieffer et al. |
| 7,338,433 B2 | 3/2008 | Coe |
| 7,347,868 B2 | 3/2008 | Burnett et al. |
| 7,347,875 B2 | 3/2008 | Levine et al. |
| 7,354,454 B2 | 4/2008 | Stack et al. |
| 7,364,591 B2 | 4/2008 | Silverman et al. |
| 7,368,577 B2 | 5/2008 | Assaf et al. |
| 7,371,862 B2 | 5/2008 | Vanotti et al. |
| 7,410,988 B2 | 8/2008 | Dickson et al. |
| 7,416,885 B2 | 8/2008 | Freeman et al. |
| 7,427,415 B2 | 9/2008 | Scharp et al. |
| 7,435,739 B2 | 10/2008 | Chen et al. |
| 7,462,487 B2 | 12/2008 | Tsao |
| 7,468,355 B2 | 12/2008 | Hamdi et al. |
| 7,476,256 B2 | 1/2009 | Meade et al. |
| 7,483,746 B2 | 1/2009 | Lee et al. |
| 7,498,445 B2 | 3/2009 | Assaf et al. |
| 7,503,922 B2 | 3/2009 | Deem et al. |
| 7,510,559 B2 | 3/2009 | Deem et al. |
| 7,511,070 B2 | 3/2009 | Grainger et al. |
| 7,513,914 B2 | 4/2009 | Schurr |
| 7,530,985 B2 | 5/2009 | Takemoto et al. |
| 7,547,312 B2 | 6/2009 | Bauman et al. |
| 7,579,477 B2 | 8/2009 | Assaf et al. |
| 7,582,313 B2 | 9/2009 | Faustman |
| 7,585,869 B2 | 9/2009 | Bhattacharya et al. |
| 7,594,926 B2 | 9/2009 | Linder et al. |
| 7,601,525 B2 | 10/2009 | Batich et al. |
| 7,604,649 B2 | 10/2009 | McGuckin et al. |
| 7,608,114 B2 | 10/2009 | Levine et al. |
| 7,620,454 B2 | 11/2009 | Dinsmoor et al. |
| 7,620,560 B2 | 11/2009 | Dang |
| 7,625,939 B2 | 12/2009 | Heiser et al. |
| 7,628,821 B2 | 12/2009 | Stack et al. |
| 7,628,988 B2 | 12/2009 | Faustman |
| 7,637,905 B2 | 12/2009 | Saadat et al. |
| 7,637,919 B2 | 12/2009 | Ishikawa et al. |
| 7,654,951 B2 | 2/2010 | Ishikawa |
| 7,662,929 B2 | 2/2010 | Brown et al. |
| 7,674,396 B2 | 3/2010 | Sterling et al. |
| 7,674,457 B2 | 3/2010 | Borlongan et al. |
| 7,678,068 B2 | 3/2010 | Levine et al. |
| 7,682,330 B2 | 3/2010 | Meade et al. |

(56) References Cited

U.S. PATENT DOCUMENTS

| | | | |
|---|---|---|---|
| 7,691,152 | B2 | 4/2010 | Silverman et al. |
| 7,695,446 | B2 | 4/2010 | Levine et al. |
| 7,696,213 | B2 | 4/2010 | Cheng et al. |
| 7,699,863 | B2 | 4/2010 | Marco et al. |
| 7,725,333 | B2 | 5/2010 | Dang |
| 7,727,143 | B2 | 6/2010 | Birk et al. |
| 7,731,757 | B2 | 6/2010 | Taylor et al. |
| 7,736,373 | B2 | 6/2010 | Laufer et al. |
| 7,741,336 | B2 | 6/2010 | Kath et al. |
| 7,742,818 | B2 | 6/2010 | Dinsmoor et al. |
| 7,749,254 | B2 | 7/2010 | Sobelman et al. |
| 7,758,535 | B2 | 7/2010 | Levine et al. |
| 7,765,008 | B2 | 7/2010 | Ben-Haim et al. |
| 7,766,861 | B2 | 8/2010 | Levine et al. |
| 7,766,973 | B2 | 8/2010 | Levine et al. |
| 7,771,382 | B2 | 8/2010 | Levine et al. |
| 7,774,216 | B2 | 8/2010 | Dang |
| 7,780,590 | B2 | 8/2010 | Birk et al. |
| 7,794,447 | B2 | 9/2010 | Dann et al. |
| 7,795,290 | B2 | 9/2010 | Dickson et al. |
| 7,798,954 | B2 | 9/2010 | Birk et al. |
| 7,799,088 | B2 | 9/2010 | Geitz |
| 7,803,177 | B2 | 9/2010 | Hartley et al. |
| 7,803,195 | B2 | 9/2010 | Levy et al. |
| 7,811,298 | B2 | 10/2010 | Birk |
| 7,811,299 | B2 | 10/2010 | Bachmann et al. |
| 7,815,589 | B2 | 10/2010 | Meade et al. |
| 7,815,591 | B2 | 10/2010 | Levine et al. |
| 7,819,836 | B2 | 10/2010 | Levine et al. |
| 7,833,280 | B2 | 11/2010 | Stack et al. |
| 7,837,643 | B2 | 11/2010 | Levine et al. |
| 7,837,669 | B2 | 11/2010 | Dann et al. |
| 7,838,524 | B2 | 11/2010 | Lee et al. |
| 7,840,269 | B2 | 11/2010 | Policker et al. |
| 7,846,138 | B2 | 12/2010 | Dann et al. |
| 7,850,704 | B2 | 12/2010 | Burnett et al. |
| 7,862,574 | B2 | 1/2011 | Deem et al. |
| 7,867,283 | B2 | 1/2011 | Krueger et al. |
| 7,881,797 | B2 | 2/2011 | Griffin et al. |
| 7,883,524 | B2 | 2/2011 | Chen |
| 7,892,214 | B2 | 2/2011 | Kagan et al. |
| 7,892,827 | B2 | 2/2011 | Matschiner et al. |
| 7,901,419 | B2 | 3/2011 | Bachmann et al. |
| 7,909,838 | B2 | 3/2011 | Deem et al. |
| 7,922,684 | B2 | 4/2011 | Weitzner et al. |
| 7,928,109 | B2 | 4/2011 | Luzzio et al. |
| 7,935,073 | B2 | 5/2011 | Levine et al. |
| 7,945,323 | B2 | 5/2011 | Jaax et al. |
| 7,959,552 | B2 | 6/2011 | Jordan et al. |
| 7,959,640 | B2 | 6/2011 | Kantsevoy et al. |
| 7,960,345 | B2 | 6/2011 | Kim |
| 7,966,071 | B2 | 6/2011 | Ben-Haim et al. |
| 7,968,575 | B2 | 6/2011 | Assaf et al. |
| 7,972,346 | B2 | 7/2011 | Bachmann et al. |
| 7,976,488 | B2 | 7/2011 | Levine et al. |
| 7,979,290 | B2 | 7/2011 | Dang |
| 7,981,162 | B2 | 7/2011 | Stack et al. |
| 7,981,163 | B2 | 7/2011 | Meade et al. |
| 7,985,844 | B2 | 7/2011 | Brown et al. |
| 7,998,220 | B2 | 8/2011 | Murphy |
| 7,998,966 | B2 | 8/2011 | Bearss et al. |
| 8,002,731 | B2 | 8/2011 | Weitzner et al. |
| 8,003,806 | B2 | 8/2011 | Bloxham et al. |
| 8,006,701 | B2 | 8/2011 | Bilotti et al. |
| 8,007,507 | B2 | 8/2011 | Waller |
| 8,008,449 | B2 | 8/2011 | Korman et al. |
| 8,012,135 | B2 | 9/2011 | Dann et al. |
| 8,012,140 | B1 | 9/2011 | Kagan et al. |
| 8,012,162 | B2 | 9/2011 | Bachmann |
| 8,012,966 | B2 | 9/2011 | Tang et al. |
| 8,021,693 | B2 | 9/2011 | Faustman |
| 8,043,206 | B2 | 10/2011 | Birk |
| 8,043,248 | B2 | 10/2011 | Pasricha |
| 8,048,169 | B2 | 11/2011 | Burnett et al. |
| 8,048,170 | B2 | 11/2011 | Silverman et al. |
| 8,057,420 | B2 | 11/2011 | Meade et al. |
| 8,057,494 | B2 | 11/2011 | Laufer et al. |
| 8,062,656 | B2 | 11/2011 | Oh-Lee et al. |
| 8,066,689 | B2 | 11/2011 | Mitelberg et al. |
| 8,070,743 | B2 | 12/2011 | Kagan et al. |
| 8,070,824 | B2 | 12/2011 | Burnett et al. |
| 8,075,577 | B2 | 12/2011 | Deem et al. |
| 8,079,974 | B2 | 12/2011 | Stergiopulos |
| 8,080,022 | B2 | 12/2011 | Deem et al. |
| 8,080,025 | B2 | 12/2011 | Deem et al. |
| 8,084,457 | B2 | 12/2011 | Choidas et al. |
| 8,084,484 | B2 | 12/2011 | Frank et al. |
| 8,092,482 | B2 | 1/2012 | Gannoe et al. |
| 8,095,219 | B2 | 1/2012 | Lee et al. |
| 8,096,966 | B2 | 1/2012 | Levine et al. |
| 8,105,392 | B2 | 1/2012 | Durgin |
| 8,106,197 | B2 | 1/2012 | Cui et al. |
| 8,109,895 | B2 | 2/2012 | Williams et al. |
| 8,114,045 | B2 | 2/2012 | Surti |
| 8,114,893 | B2 | 2/2012 | Baell et al. |
| 8,116,883 | B2 | 2/2012 | Williams et al. |
| 8,118,774 | B2 | 2/2012 | Dann et al. |
| 8,121,869 | B2 | 2/2012 | Dang |
| 8,123,765 | B2 | 2/2012 | Deem et al. |
| 8,123,766 | B2 | 2/2012 | Bauman et al. |
| 8,123,767 | B2 | 2/2012 | Bauman et al. |
| 8,134,010 | B2 | 3/2012 | Assaf |
| 8,137,301 | B2 | 3/2012 | Levine et al. |
| 8,137,662 | B2 | 3/2012 | Freeman et al. |
| 8,142,469 | B2 | 3/2012 | Sosnowski et al. |
| 8,142,514 | B2 | 3/2012 | Geitz |
| 8,147,561 | B2 | 4/2012 | Binmoeller |
| 8,162,871 | B2 | 4/2012 | Levine et al. |
| 8,173,129 | B2 | 5/2012 | Faustman |
| 8,177,853 | B2 | 5/2012 | Stack et al. |
| 8,182,441 | B2 | 5/2012 | Swain et al. |
| 8,182,459 | B2 | 5/2012 | Dann et al. |
| 8,182,543 | B2 | 5/2012 | Schurr |
| 8,187,289 | B2 | 5/2012 | Tacchino et al. |
| 8,207,166 | B2 | 6/2012 | Lee et al. |
| 8,211,186 | B2 | 7/2012 | Belhe et al. |
| 8,216,266 | B2 | 7/2012 | Hively |
| 8,216,268 | B2 | 7/2012 | Haller et al. |
| 8,219,201 | B2 | 7/2012 | Ben-Haim et al. |
| 8,226,593 | B2 | 7/2012 | Graham et al. |
| 8,226,602 | B2 | 7/2012 | Quijana et al. |
| 8,232,273 | B2 | 7/2012 | Baell et al. |
| 8,236,023 | B2 | 8/2012 | Birk et al. |
| 8,247,411 | B2 | 8/2012 | Luzzio et al. |
| 8,252,816 | B2 | 8/2012 | Frank et al. |
| 8,268,821 | B2 | 9/2012 | Nadeson et al. |
| 8,273,755 | B2 | 9/2012 | Cheng et al. |
| 8,277,468 | B2 | 10/2012 | Laufer et al. |
| 8,282,598 | B2 | 10/2012 | Belhe et al. |
| 8,282,666 | B2 | 10/2012 | Birk |
| 8,290,582 | B2 | 10/2012 | Lin et al. |
| 8,292,800 | B2 | 10/2012 | Stone et al. |
| 8,296,165 | B2 | 10/2012 | Dang |
| 8,299,022 | B2 | 10/2012 | Dong |
| 8,303,669 | B2 | 11/2012 | Meade et al. |
| 8,308,630 | B2 | 11/2012 | Birk et al. |
| 8,308,813 | B2 | 11/2012 | Krueger et al. |
| 8,317,677 | B2 | 11/2012 | Bertolote et al. |
| 8,323,180 | B2 | 12/2012 | Birk et al. |
| 8,323,229 | B2 | 12/2012 | Shin et al. |
| 8,334,263 | B2 | 12/2012 | Nadeson et al. |
| 8,337,567 | B2 | 12/2012 | Stack et al. |
| 8,337,829 | B2 | 12/2012 | Freeman et al. |
| 8,357,501 | B2 | 1/2013 | Jackson et al. |
| 8,362,251 | B2 | 1/2013 | Tang et al. |
| 8,366,602 | B2 | 2/2013 | Birk et al. |
| 8,376,929 | B2 | 2/2013 | Birk et al. |
| 8,377,081 | B2 | 2/2013 | Bachmann et al. |
| 8,382,780 | B2 | 2/2013 | Birk |
| 8,398,654 | B2 | 3/2013 | Franklin et al. |
| 8,399,223 | B2 | 3/2013 | Park et al. |
| 8,403,877 | B2 | 3/2013 | Priplata et al. |
| 8,409,221 | B2 | 4/2013 | Franklin et al. |
| 8,409,226 | B2 | 4/2013 | Kantsevoy et al. |

(56) References Cited

U.S. PATENT DOCUMENTS

| | | |
|---|---|---|
| 8,414,559 B2 | 4/2013 | Gross |
| 8,425,451 B2 | 4/2013 | Levine et al. |
| 8,430,894 B2 | 4/2013 | Brooks et al. |
| 8,430,895 B2 | 4/2013 | Brooks et al. |
| 8,431,597 B2 | 4/2013 | Munchhof et al. |
| 8,436,011 B2 | 5/2013 | Bellevergue et al. |
| 8,440,822 B2 | 5/2013 | Luzzio et al. |
| 8,465,447 B2 | 6/2013 | Krueger et al. |
| 8,470,815 B2 | 6/2013 | Saulnier et al. |
| 8,475,401 B2 | 7/2013 | Priplata et al. |
| 8,486,153 B2 | 7/2013 | Levine et al. |
| 8,491,472 B2 | 7/2013 | Mitelberg et al. |
| 8,491,519 B2 | 7/2013 | Chin |
| 8,496,931 B2 | 7/2013 | Pogue et al. |
| 8,506,517 B2 | 8/2013 | Stergiopulos |
| 8,506,532 B2 | 8/2013 | Olroyd et al. |
| 8,507,274 B2 | 8/2013 | Melton et al. |
| 8,515,542 B2 | 8/2013 | Jaax et al. |
| 8,517,915 B2 | 8/2013 | Perron et al. |
| 8,518,970 B2 | 8/2013 | Baell et al. |
| 8,529,943 B2 | 9/2013 | Kliger et al. |
| 8,556,918 B2 | 10/2013 | Bauman et al. |
| 8,556,925 B2 | 10/2013 | Makower et al. |
| 8,556,934 B2 | 10/2013 | Godin |
| 8,568,488 B2 | 10/2013 | Stack et al. |
| 8,579,988 B2 | 11/2013 | Burnett et al. |
| 8,585,628 B2 | 11/2013 | Harris et al. |
| 8,585,753 B2 | 11/2013 | Scanlon et al. |
| 8,585,771 B2 | 11/2013 | Binmoeller et al. |
| 8,591,452 B2 | 11/2013 | Priplata et al. |
| 8,591,533 B2 | 11/2013 | Needleman et al. |
| 8,591,598 B2 | 11/2013 | Silverman et al. |
| 8,597,224 B2 | 12/2013 | Vargas |
| 8,603,186 B2 | 12/2013 | Binmoeller |
| 8,613,749 B2 | 12/2013 | Deem et al. |
| 8,623,893 B2 | 1/2014 | Lassalle et al. |
| 8,628,554 B2 | 1/2014 | Sharma |
| 8,628,583 B2 | 1/2014 | Meade et al. |
| 8,633,204 B2 | 1/2014 | Cheng et al. |
| 8,636,683 B2 | 1/2014 | Chin et al. |
| 8,636,751 B2 | 1/2014 | Albrecht et al. |
| 8,642,623 B2 | 2/2014 | Frank et al. |
| 8,652,083 B2 | 2/2014 | Weitzner et al. |
| 8,657,885 B2 | 2/2014 | Burnett et al. |
| 8,663,301 B2 | 3/2014 | Riina et al. |
| 8,663,338 B2 | 3/2014 | Burnett et al. |
| 8,678,993 B2 | 3/2014 | Stroumpoulis |
| 8,679,137 B2 | 3/2014 | Bauman et al. |
| 8,683,881 B2 | 4/2014 | Bouasaysy et al. |
| 8,691,271 B2 | 4/2014 | Burnett et al. |
| 8,698,373 B2 | 4/2014 | Augarten et al. |
| 8,702,641 B2 | 4/2014 | Belhe et al. |
| 8,702,642 B2 | 4/2014 | Belhe et al. |
| 8,708,979 B2 | 4/2014 | Honaryar et al. |
| 8,715,158 B2 | 5/2014 | Honaryar et al. |
| 8,725,435 B2 | 5/2014 | Snow et al. |
| 8,753,369 B2 | 6/2014 | Murature et al. |
| 8,758,221 B2 | 6/2014 | Snow et al. |
| 8,764,624 B2 | 7/2014 | Snow et al. |
| 8,771,219 B2 | 7/2014 | Meade et al. |
| 8,795,301 B2 | 8/2014 | Burnett et al. |
| 8,801,597 B2 | 8/2014 | Franklin et al. |
| 8,801,647 B2 | 8/2014 | Melanson et al. |
| 8,808,270 B2 | 8/2014 | Dann et al. |
| 8,821,373 B2 | 9/2014 | Schwab et al. |
| 8,821,429 B2 | 9/2014 | Vargas |
| 8,821,430 B2 | 9/2014 | Stergiopulos |
| 8,821,521 B2 | 9/2014 | Burnett |
| 8,821,584 B2 | 9/2014 | Burnett et al. |
| 8,834,405 B2 | 9/2014 | Meade et al. |
| 8,834,553 B2 | 9/2014 | Melanson et al. |
| 8,840,541 B2 | 9/2014 | Snow et al. |
| 8,840,679 B2 | 9/2014 | Durgin |
| 8,840,952 B2 | 9/2014 | Ashby et al. |
| 8,845,513 B2 | 9/2014 | Coe |
| 8,845,672 B2 | 9/2014 | Alverdy |
| 8,858,421 B2 | 10/2014 | Honaryar |
| 8,864,840 B2 | 10/2014 | Dominguez et al. |
| 8,870,806 B2 | 10/2014 | Levine et al. |
| 8,870,966 B2 | 10/2014 | Schwab et al. |
| 8,876,694 B2 | 11/2014 | Honaryar et al. |
| 8,882,655 B2 | 11/2014 | Nitka et al. |
| 8,882,698 B2 | 11/2014 | Levine et al. |
| 8,882,728 B2 | 11/2014 | Harders et al. |
| 8,882,798 B2 | 11/2014 | Schwab et al. |
| 8,888,732 B2 | 11/2014 | Raven et al. |
| 8,888,797 B2 | 11/2014 | Burnett et al. |
| 8,894,568 B2 | 11/2014 | Kwok et al. |
| 8,900,117 B2 | 12/2014 | Birk |
| 8,900,118 B2 | 12/2014 | Birk et al. |
| 8,905,915 B2 | 12/2014 | Birk |
| 8,905,916 B2 | 12/2014 | Jacobs et al. |
| 8,920,358 B2 | 12/2014 | Levine et al. |
| 8,920,447 B2 | 12/2014 | Dominguez |
| 8,932,247 B2 | 1/2015 | Stergiopulos |
| 8,939,888 B2 | 1/2015 | Augarten et al. |
| 8,956,318 B2 | 2/2015 | Miller et al. |
| 8,956,380 B2 | 2/2015 | Dominguez et al. |
| 8,961,393 B2 | 2/2015 | Rion et al. |
| 8,961,394 B2 | 2/2015 | Honaryar et al. |
| 8,968,177 B2 | 3/2015 | Silverman et al. |
| 8,968,270 B2 | 3/2015 | Kagan et al. |
| 8,979,735 B2 | 3/2015 | Augarten |
| 8,992,415 B2 | 3/2015 | Deuel et al. |
| 8,992,559 B2 | 3/2015 | Weitzner et al. |
| 9,017,358 B2 | 4/2015 | Schwab et al. |
| 9,023,062 B2 | 5/2015 | Franklin et al. |
| 9,023,063 B2 | 5/2015 | Franklin et al. |
| 9,028,394 B2 | 5/2015 | Honaryar et al. |
| 9,039,649 B2 | 5/2015 | Neisz et al. |
| 9,044,298 B2 | 6/2015 | Franklin et al. |
| 9,044,300 B2 | 6/2015 | Belhe et al. |
| 9,050,165 B2 | 6/2015 | Perron |
| 9,050,168 B2 | 6/2015 | Neisz et al. |
| 9,050,174 B2 | 6/2015 | Pecor et al. |
| 9,060,844 B2 | 6/2015 | Kagan et al. |
| 9,066,780 B2 | 6/2015 | Weber |
| 9,072,579 B2 | 7/2015 | Birk et al. |
| 9,084,669 B2 | 7/2015 | Meade et al. |
| 9,089,395 B2 | 7/2015 | Honaryar |
| 9,095,405 B2 | 8/2015 | Babkes et al. |
| 9,095,416 B2 | 8/2015 | Meade et al. |
| 9,526,648 B2 | 12/2016 | Sharma |
| 10,010,439 B2 | 7/2018 | Sharma et al. |
| 10,413,436 B2 | 9/2019 | Sharma |
| 10,420,665 B2 | 9/2019 | Sharma et al. |
| 10,512,557 B2 | 12/2019 | Sharma |
| 10,779,980 B2 | 9/2020 | Sharma et al. |
| 2001/0011543 A1 | 8/2001 | Forsell |
| 2002/0006962 A1 | 1/2002 | Wang et al. |
| 2002/0071857 A1 | 6/2002 | Kararli et al. |
| 2002/0091439 A1 | 7/2002 | Baker et al. |
| 2002/0137086 A1 | 9/2002 | Olek et al. |
| 2002/0143387 A1 | 10/2002 | Soetikno et al. |
| 2002/0155100 A1 | 10/2002 | Kieffer et al. |
| 2002/0165572 A1 | 11/2002 | Saadat |
| 2002/0165738 A1 | 11/2002 | Dang |
| 2002/0169165 A1 | 11/2002 | Kath et al. |
| 2002/0173987 A1 | 11/2002 | Dang |
| 2002/0173988 A1 | 11/2002 | Dang |
| 2002/0173989 A1 | 11/2002 | Dang |
| 2002/0173992 A1 | 11/2002 | Dang |
| 2002/0183768 A1 | 12/2002 | Deem et al. |
| 2002/0193816 A1 | 12/2002 | Laufer et al. |
| 2002/0193828 A1 | 12/2002 | Griffin et al. |
| 2002/0197656 A1 | 12/2002 | Li et al. |
| 2003/0018299 A1 | 1/2003 | Stone |
| 2003/0040804 A1* | 2/2003 | Stack .................. A61F 5/0069 623/23.7 |
| 2003/0040808 A1 | 2/2003 | Stack et al. |
| 2003/0050684 A1 | 3/2003 | Abrams et al. |
| 2003/0053985 A1 | 3/2003 | Shachar et al. |
| 2003/0055465 A1 | 3/2003 | Ben-Haim et al. |
| 2003/0055466 A1 | 3/2003 | Ben-Haim et al. |

(56) References Cited

U.S. PATENT DOCUMENTS

| | | |
|---|---|---|
| 2003/0055467 A1 | 3/2003 | Ben-Haim et al. |
| 2003/0064970 A1 | 4/2003 | Grainger et al. |
| 2003/0065359 A1 | 4/2003 | Weller et al. |
| 2003/0066987 A1 | 4/2003 | Schmidt et al. |
| 2003/0086975 A1 | 5/2003 | Ringeisen |
| 2003/0108597 A1 | 6/2003 | Chancellor et al. |
| 2003/0109892 A1 | 6/2003 | Deem et al. |
| 2003/0109935 A1 | 6/2003 | Geitz |
| 2003/0120265 A1 | 6/2003 | Deem et al. |
| 2003/0153905 A1 | 8/2003 | Edwards et al. |
| 2003/0158217 A1 | 8/2003 | Kath et al. |
| 2003/0171261 A1 | 9/2003 | Livingston et al. |
| 2003/0171386 A1 | 9/2003 | Connell et al. |
| 2003/0190368 A1 | 10/2003 | Stoughton et al. |
| 2003/0191476 A1 | 10/2003 | Smit |
| 2003/0191492 A1 | 10/2003 | Gellman et al. |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208260 A1 | 11/2003 | Lau et al. |
| 2003/0232752 A1 | 12/2003 | Freeman et al. |
| 2004/0024386 A1 | 2/2004 | Deem et al. |
| 2004/0028658 A1 | 2/2004 | Faustman |
| 2004/0039350 A1 | 2/2004 | McKittrick |
| 2004/0039452 A1 | 2/2004 | Bessler |
| 2004/0044357 A1 | 3/2004 | Gannoe et al. |
| 2004/0045045 A1 | 3/2004 | Mather et al. |
| 2004/0062778 A1 | 4/2004 | Shefer et al. |
| 2004/0073278 A1 | 4/2004 | Pachys |
| 2004/0087876 A1 | 5/2004 | Eskuri |
| 2004/0092892 A1 | 5/2004 | Kagan et al. |
| 2004/0097428 A1 | 5/2004 | Hamdi et al. |
| 2004/0106892 A1 | 6/2004 | Stone |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122456 A1 | 6/2004 | Saadat et al. |
| 2004/0127800 A1 | 7/2004 | Kimball et al. |
| 2004/0133147 A1 | 7/2004 | Woo |
| 2004/0138529 A1 | 7/2004 | Wiltshire et al. |
| 2004/0138760 A1 | 7/2004 | Schurr |
| 2004/0143342 A1 | 7/2004 | Stack et al. |
| 2004/0147816 A1 | 7/2004 | Policker et al. |
| 2004/0147871 A1 | 7/2004 | Burnett |
| 2004/0148034 A1 | 7/2004 | Kagan et al. |
| 2004/0158331 A1 | 8/2004 | Stack et al. |
| 2004/0170631 A1 | 9/2004 | Yacoby-Zeevi et al. |
| 2004/0171634 A1 | 9/2004 | Kania et al. |
| 2004/0172143 A1 | 9/2004 | Geitz |
| 2004/0180086 A1 | 9/2004 | Ramtoola et al. |
| 2004/0181242 A1 | 9/2004 | Stack et al. |
| 2004/0192598 A1 | 9/2004 | Kragie |
| 2004/0193184 A1 | 9/2004 | Laufer et al. |
| 2004/0204429 A1 | 10/2004 | Yuan |
| 2004/0220177 A1 | 11/2004 | Kath et al. |
| 2004/0220248 A1 | 11/2004 | Kania et al. |
| 2004/0220682 A1 | 11/2004 | Levine et al. |
| 2004/0225191 A1 | 11/2004 | Sekine et al. |
| 2004/0236381 A1 | 11/2004 | Dinsmoor et al. |
| 2004/0236382 A1 | 11/2004 | Dinsmoor et al. |
| 2004/0242604 A1 | 12/2004 | Bhattacharya et al. |
| 2004/0243152 A1 | 12/2004 | Taylor et al. |
| 2004/0254204 A1 | 12/2004 | Kath et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0009840 A1 | 1/2005 | Cui et al. |
| 2005/0020667 A1 | 1/2005 | Grainger et al. |
| 2005/0037999 A1 | 2/2005 | La et al. |
| 2005/0038097 A1 | 2/2005 | Bender et al. |
| 2005/0055039 A1 | 3/2005 | Burnett et al. |
| 2005/0075354 A1 | 4/2005 | Li et al. |
| 2005/0085923 A1 | 4/2005 | Levine et al. |
| 2005/0089577 A1 | 4/2005 | Yokoyama et al. |
| 2005/0101011 A1 | 5/2005 | Tsao |
| 2005/0101618 A1 | 5/2005 | Connell et al. |
| 2005/0124599 A1 | 6/2005 | Kath et al. |
| 2005/0124662 A1 | 6/2005 | Kania et al. |
| 2005/0125020 A1 | 6/2005 | Meade et al. |
| 2005/0125075 A1 | 6/2005 | Meade et al. |
| 2005/0130994 A1 | 6/2005 | Chen et al. |
| 2005/0143765 A1 | 6/2005 | Bachmann et al. |
| 2005/0143766 A1 | 6/2005 | Bachmann et al. |
| 2005/0158288 A1 | 7/2005 | Faustman |
| 2005/0159435 A1 | 7/2005 | Kath et al. |
| 2005/0159769 A1 | 7/2005 | Alverdy |
| 2005/0164388 A1 | 7/2005 | Son et al. |
| 2005/0169902 A1 | 8/2005 | Borlongan et al. |
| 2005/0171556 A1 | 8/2005 | Murphy |
| 2005/0192614 A1 | 9/2005 | Binmoeller |
| 2005/0196423 A1 | 9/2005 | Batich et al. |
| 2005/0197714 A1 | 9/2005 | Sayet |
| 2005/0251182 A1 | 11/2005 | Bachmann |
| 2005/0256111 A1 | 11/2005 | Kath et al. |
| 2005/0256125 A1 | 11/2005 | Kath et al. |
| 2005/0256144 A1 | 11/2005 | Kath et al. |
| 2005/0256587 A1 | 11/2005 | Egan |
| 2005/0267595 A1 | 12/2005 | Chen et al. |
| 2005/0273060 A1 | 12/2005 | Levy et al. |
| 2005/0277975 A1* | 12/2005 | Saadat .............. A61B 17/0218 606/191 |
| 2006/0002899 A1 | 1/2006 | Rice et al. |
| 2006/0009858 A1 | 1/2006 | Levine et al. |
| 2006/0015125 A1 | 1/2006 | Swain |
| 2006/0015151 A1 | 1/2006 | Aldrich |
| 2006/0020278 A1 | 1/2006 | Burnett et al. |
| 2006/0025799 A1 | 2/2006 | Basu |
| 2006/0052416 A1 | 3/2006 | Dickson et al. |
| 2006/0064120 A1 | 3/2006 | Levine et al. |
| 2006/0069138 A1 | 3/2006 | Assaf et al. |
| 2006/0069139 A1 | 3/2006 | Assaf et al. |
| 2006/0069400 A1 | 3/2006 | Burnett et al. |
| 2006/0074073 A1 | 4/2006 | Steinfeldt et al. |
| 2006/0078993 A1 | 4/2006 | Phan et al. |
| 2006/0084696 A1 | 4/2006 | Grainger et al. |
| 2006/0089571 A1 | 4/2006 | Gertner |
| 2006/0089627 A1 | 4/2006 | Burnett et al. |
| 2006/0105454 A1 | 5/2006 | Son et al. |
| 2006/0116383 A1 | 6/2006 | Bloxham et al. |
| 2006/0127437 A1 | 6/2006 | Kennedy et al. |
| 2006/0134109 A1 | 6/2006 | Gaitanaris et al. |
| 2006/0134186 A1 | 6/2006 | Carlton et al. |
| 2006/0142731 A1 | 6/2006 | Brooks |
| 2006/0142787 A1 | 6/2006 | Weller et al. |
| 2006/0161187 A1 | 7/2006 | Levine et al. |
| 2006/0161265 A1 | 7/2006 | Levine et al. |
| 2006/0183718 A1 | 8/2006 | Assaf et al. |
| 2006/0183912 A1 | 8/2006 | Assaf et al. |
| 2006/0183913 A1 | 8/2006 | Assaf et al. |
| 2006/0228775 A1 | 10/2006 | Collier et al. |
| 2006/0241130 A1 | 10/2006 | Keinan et al. |
| 2006/0241748 A1 | 10/2006 | Lee et al. |
| 2006/0271088 A1 | 11/2006 | Alfrhan |
| 2006/0276713 A1 | 12/2006 | Maier |
| 2007/0003610 A1 | 1/2007 | Chancellor et al. |
| 2007/0021382 A1 | 1/2007 | Assaf et al. |
| 2007/0021988 A1 | 1/2007 | Dang |
| 2007/0027548 A1 | 2/2007 | Levine et al. |
| 2007/0032879 A1 | 2/2007 | Levine et al. |
| 2007/0037883 A1 | 2/2007 | Dusting et al. |
| 2007/0060940 A1 | 3/2007 | Brazzini et al. |
| 2007/0072874 A1 | 3/2007 | Cui et al. |
| 2007/0072885 A1 | 3/2007 | Bhattacharya et al. |
| 2007/0078435 A1 | 4/2007 | Stone et al. |
| 2007/0083224 A1 | 4/2007 | Hively |
| 2007/0083271 A1 | 4/2007 | Levine et al. |
| 2007/0088389 A1 | 4/2007 | Dunkin et al. |
| 2007/0100367 A1 | 5/2007 | Quijano et al. |
| 2007/0100368 A1 | 5/2007 | Quijano et al. |
| 2007/0104754 A1 | 5/2007 | Sterling et al. |
| 2007/0105861 A1 | 5/2007 | Lee et al. |
| 2007/0112020 A1 | 5/2007 | Vanotti et al. |
| 2007/0118158 A1 | 5/2007 | Deem et al. |

(56) References Cited

U.S. PATENT DOCUMENTS

| | | |
|---|---|---|
| 2007/0118159 A1 | 5/2007 | Deem et al. |
| 2007/0118168 A1 | 5/2007 | Lointier et al. |
| 2007/0135335 A1 | 6/2007 | Collier et al. |
| 2007/0135825 A1 | 6/2007 | Binmoeller |
| 2007/0135829 A1 | 6/2007 | Paganon |
| 2007/0135831 A1 | 6/2007 | Burnett |
| 2007/0148129 A1 | 6/2007 | Shortman et al. |
| 2007/0149994 A1 | 6/2007 | Sosnowski et al. |
| 2007/0156248 A1 | 7/2007 | Marco et al. |
| 2007/0167963 A1 | 7/2007 | Deem et al. |
| 2007/0173881 A1 | 7/2007 | Birk et al. |
| 2007/0178160 A1 | 8/2007 | Burnett |
| 2007/0185176 A1 | 8/2007 | Van et al. |
| 2007/0185540 A1 | 8/2007 | Ben-Haim et al. |
| 2007/0191344 A1 | 8/2007 | Choidas et al. |
| 2007/0198039 A1 | 8/2007 | Jones et al. |
| 2007/0198074 A1 | 8/2007 | Dann et al. |
| 2007/0207186 A1 | 9/2007 | Scanlon et al. |
| 2007/0210018 A1 | 9/2007 | Wallwiener et al. |
| 2007/0213740 A1 | 9/2007 | Deem et al. |
| 2007/0213748 A1 | 9/2007 | Deem et al. |
| 2007/0219570 A1 | 9/2007 | Deem et al. |
| 2007/0250083 A1 | 10/2007 | Deem et al. |
| 2007/0250132 A1 | 10/2007 | Burnett |
| 2007/0255379 A1 | 11/2007 | Williams et al. |
| 2007/0265598 A1 | 11/2007 | Karasik |
| 2007/0265709 A1 | 11/2007 | Rajan et al. |
| 2007/0275902 A1 | 11/2007 | Gonda et al. |
| 2007/0275962 A1 | 11/2007 | Koul et al. |
| 2007/0276428 A1 | 11/2007 | Haller et al. |
| 2007/0282349 A1 | 12/2007 | Deem et al. |
| 2007/0282452 A1 | 12/2007 | Weitzner et al. |
| 2007/0282453 A1 | 12/2007 | Weitzner et al. |
| 2007/0286856 A1 | 12/2007 | Brown et al. |
| 2007/0293716 A1 | 12/2007 | Baker et al. |
| 2007/0293885 A1 | 12/2007 | Binmoeller |
| 2007/0299320 A1 | 12/2007 | Policker et al. |
| 2008/0021742 A1 | 1/2008 | Dang |
| 2008/0026072 A1 | 1/2008 | Nakayama et al. |
| 2008/0027469 A1 | 1/2008 | Bachmann |
| 2008/0039463 A1 | 2/2008 | Nadeson et al. |
| 2008/0051849 A1 | 2/2008 | Ben-Haim et al. |
| 2008/0058887 A1 | 3/2008 | Griffin et al. |
| 2008/0058889 A1 | 3/2008 | Ben-Haim et al. |
| 2008/0058891 A1 | 3/2008 | Ben-Haim et al. |
| 2008/0059231 A1 | 3/2008 | Dang |
| 2008/0065136 A1 | 3/2008 | Young |
| 2008/0065421 A1 | 3/2008 | Dang |
| 2008/0071383 A1 | 3/2008 | Levine et al. |
| 2008/0090801 A1 | 4/2008 | Cheng et al. |
| 2008/0097466 A1 | 4/2008 | Levine et al. |
| 2008/0097513 A1 | 4/2008 | Kaji et al. |
| 2008/0097788 A1 | 4/2008 | Dang |
| 2008/0120734 A1 | 5/2008 | Kieffer et al. |
| 2008/0154129 A1 | 6/2008 | Mizunuma |
| 2008/0161838 A1 | 7/2008 | D et al. |
| 2008/0175828 A1 | 7/2008 | Freeman et al. |
| 2008/0187575 A1 | 8/2008 | Klebl et al. |
| 2008/0194574 A1 | 8/2008 | Eikhoff et al. |
| 2008/0194596 A1 | 8/2008 | Letrent |
| 2008/0195226 A1 | 8/2008 | Williams et al. |
| 2008/0207677 A1 | 8/2008 | Muller et al. |
| 2008/0208241 A1 | 8/2008 | Weiner et al. |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0214545 A1 | 9/2008 | Lee et al. |
| 2008/0221595 A1 | 9/2008 | Surti |
| 2008/0228030 A1 | 9/2008 | Godin |
| 2008/0228066 A1 | 9/2008 | Waitzman |
| 2008/0233163 A1 | 9/2008 | Assaf |
| 2008/0234718 A1 | 9/2008 | Paganon et al. |
| 2008/0234834 A1 | 9/2008 | Meade et al. |
| 2008/0243071 A1 | 10/2008 | Quijano et al. |
| 2008/0243166 A1 | 10/2008 | Paganon et al. |
| 2008/0243167 A1 | 10/2008 | Paganon et al. |
| 2008/0249533 A1 | 10/2008 | Godin |
| 2008/0249635 A1 | 10/2008 | Weitzner et al. |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0260797 A1 | 10/2008 | Oh-Lee et al. |
| 2008/0261258 A1 | 10/2008 | Smith et al. |
| 2008/0262529 A1 | 10/2008 | Jacques |
| 2008/0269289 A1 | 10/2008 | Frank et al. |
| 2008/0269555 A1 | 10/2008 | Paganon et al. |
| 2008/0281257 A1 | 11/2008 | Waller |
| 2008/0281375 A1 | 11/2008 | Chen |
| 2008/0293618 A1 | 11/2008 | Heiser et al. |
| 2008/0293733 A1 | 11/2008 | Bearss et al. |
| 2008/0300234 A1 | 12/2008 | Kath et al. |
| 2008/0302855 A1 | 12/2008 | Bilotti et al. |
| 2008/0319471 A1 | 12/2008 | Sosnowski et al. |
| 2009/0005867 A1 | 1/2009 | Lefranc et al. |
| 2009/0012544 A1 | 1/2009 | Thompson et al. |
| 2009/0042785 A1 | 2/2009 | Matschiner et al. |
| 2009/0048313 A1 | 2/2009 | Dickson et al. |
| 2009/0053182 A1 | 2/2009 | Ichim et al. |
| 2009/0054395 A1 | 2/2009 | Luzzio et al. |
| 2009/0062401 A1 | 3/2009 | Odermatt et al. |
| 2009/0088676 A1 | 4/2009 | Murata |
| 2009/0093839 A1 | 4/2009 | Kelleher |
| 2009/0105562 A1 | 4/2009 | Chiou et al. |
| 2009/0111805 A1 | 4/2009 | Morris et al. |
| 2009/0138094 A1 | 5/2009 | Schurr |
| 2009/0142413 A1 | 6/2009 | Allen et al. |
| 2009/0149849 A1 | 6/2009 | Lin et al. |
| 2009/0156590 A1 | 6/2009 | Frank et al. |
| 2009/0164028 A1 | 6/2009 | Chen |
| 2009/0171383 A1 | 7/2009 | Cole et al. |
| 2009/0178153 A1 | 7/2009 | Gaitanaris et al. |
| 2009/0182303 A1 | 7/2009 | Walak et al. |
| 2009/0182424 A1 | 7/2009 | Marco et al. |
| 2009/0187197 A1 | 7/2009 | Roeber et al. |
| 2009/0187200 A1 | 7/2009 | Burnett et al. |
| 2009/0187201 A1 | 7/2009 | Burnett et al. |
| 2009/0196912 A1 | 8/2009 | Eickhoff et al. |
| 2009/0198254 A1 | 8/2009 | Laufer et al. |
| 2009/0214474 A1 | 8/2009 | Jennings |
| 2009/0216262 A1 | 8/2009 | Burnett et al. |
| 2009/0217401 A1 | 8/2009 | Korman et al. |
| 2009/0226907 A1 | 9/2009 | Nice et al. |
| 2009/0227641 A1 | 9/2009 | Bhattacharya et al. |
| 2009/0259240 A1 | 10/2009 | Graham et al. |
| 2009/0264345 A1 | 10/2009 | McAlpine et al. |
| 2009/0275511 A1 | 11/2009 | Dong |
| 2009/0276055 A1 | 11/2009 | Harris et al. |
| 2009/0287231 A1 | 11/2009 | Brooks et al. |
| 2009/0299486 A1 | 12/2009 | Shohat et al. |
| 2009/0299487 A1 | 12/2009 | Stack et al. |
| 2009/0306186 A1 | 12/2009 | Jackson et al. |
| 2009/0317374 A1 | 12/2009 | Park et al. |
| 2010/0004239 A1 | 1/2010 | Tang et al. |
| 2010/0016353 A1 | 1/2010 | Henne et al. |
| 2010/0029615 A1 | 2/2010 | Munchhof et al. |
| 2010/0036481 A1 | 2/2010 | Dubrul et al. |
| 2010/0048471 A1 | 2/2010 | Kim |
| 2010/0049224 A1* | 2/2010 | Vargas ............... A61F 5/0003 606/153 |
| 2010/0068177 A1 | 3/2010 | Faustman |
| 2010/0114150 A1 | 5/2010 | Magal |
| 2010/0121371 A1 | 5/2010 | Brooks et al. |
| 2010/0136114 A1 | 6/2010 | Mao |
| 2010/0137279 A1 | 6/2010 | Cheng et al. |
| 2010/0145301 A1 | 6/2010 | Magal |
| 2010/0150893 A1 | 6/2010 | Faustman |
| 2010/0152765 A1 | 6/2010 | Haley |
| 2010/0158896 A1 | 6/2010 | Brown et al. |
| 2010/0158902 A1 | 6/2010 | Pogue et al. |
| 2010/0168563 A1 | 7/2010 | Braver |
| 2010/0179584 A1 | 7/2010 | Carpenter et al. |
| 2010/0190782 A1 | 7/2010 | Baell et al. |
| 2010/0204093 A1 | 8/2010 | Kaushal et al. |
| 2010/0204221 A1 | 8/2010 | Vankayalapati et al. |

(56) References Cited

U.S. PATENT DOCUMENTS

| | | |
|---|---|---|
| 2010/0204688 A1 | 8/2010 | Hoey et al. |
| 2010/0209488 A1 | 8/2010 | Wrasidlo et al. |
| 2010/0210622 A1 | 8/2010 | Baell et al. |
| 2010/0221233 A1 | 9/2010 | Borlongan et al. |
| 2010/0222381 A1 | 9/2010 | Vankayalapati et al. |
| 2010/0234435 A1 | 9/2010 | Bhattacharya et al. |
| 2010/0234886 A1 | 9/2010 | Godin |
| 2010/0235197 A1 | 9/2010 | Dang |
| 2010/0247691 A1 | 9/2010 | Kim |
| 2010/0249822 A1 | 9/2010 | Nihalani |
| 2010/0249825 A1* | 9/2010 | Nihalani ......... A61B 17/12163 606/198 |
| 2010/0255087 A1 | 10/2010 | Coulter |
| 2010/0256654 A1 | 10/2010 | Pasricha |
| 2010/0256775 A1 | 10/2010 | Belhe et al. |
| 2010/0261162 A1 | 10/2010 | Nice et al. |
| 2010/0266675 A1 | 10/2010 | Gerwick et al. |
| 2010/0268260 A1 | 10/2010 | Riina et al. |
| 2010/0286628 A1 | 11/2010 | Gross |
| 2010/0286660 A1 | 11/2010 | Gross |
| 2010/0298631 A1 | 11/2010 | Stack et al. |
| 2010/0298741 A1 | 11/2010 | Gross et al. |
| 2010/0305590 A1 | 12/2010 | Holmes et al. |
| 2010/0324572 A1 | 12/2010 | Needleman et al. |
| 2010/0324928 A1 | 12/2010 | Dang |
| 2011/0004146 A1 | 1/2011 | Priplata et al. |
| 2011/0004320 A1 | 1/2011 | Priplata et al. |
| 2011/0009801 A1 | 1/2011 | Blaeser et al. |
| 2011/0040230 A1 | 2/2011 | Laufer |
| 2011/0040232 A1 | 2/2011 | Magal |
| 2011/0066175 A1 | 3/2011 | Gross |
| 2011/0068143 A1 | 3/2011 | Laufer et al. |
| 2011/0082535 A1 | 4/2011 | Shin et al. |
| 2011/0092482 A1 | 4/2011 | Nadeson et al. |
| 2011/0097280 A1 | 4/2011 | Dees et al. |
| 2011/0098730 A1 | 4/2011 | Kelleher |
| 2011/0118650 A1 | 5/2011 | Nihalani |
| 2011/0124643 A1 | 5/2011 | Bellevergue et al. |
| 2011/0125211 A1 | 5/2011 | Griffin et al. |
| 2011/0130775 A1 | 6/2011 | Tacchino et al. |
| 2011/0136809 A1 | 6/2011 | Lee et al. |
| 2011/0137428 A1 | 6/2011 | Terliuc |
| 2011/0142905 A1 | 6/2011 | Bar-Shalom et al. |
| 2011/0152608 A1 | 6/2011 | Bachmann et al. |
| 2011/0152899 A1 | 6/2011 | Deem et al. |
| 2011/0166120 A1 | 7/2011 | Luzzio et al. |
| 2011/0172585 A1 | 7/2011 | Weitzner et al. |
| 2011/0185439 A1 | 7/2011 | Gaitanaris et al. |
| 2011/0190905 A1 | 8/2011 | Behan |
| 2011/0206760 A1 | 8/2011 | Kliger et al. |
| 2011/0213469 A1 | 9/2011 | Chin et al. |
| 2011/0214189 A1 | 9/2011 | Gaitanaris et al. |
| 2011/0218143 A1 | 9/2011 | Kaushal et al. |
| 2011/0218563 A1 | 9/2011 | Brooks et al. |
| 2011/0245752 A1 | 10/2011 | Levine et al. |
| 2011/0256123 A1 | 10/2011 | Ilan et al. |
| 2011/0257580 A1 | 10/2011 | Meade et al. |
| 2011/0263504 A1 | 10/2011 | Cerami et al. |
| 2011/0269772 A1 | 11/2011 | Bearss et al. |
| 2011/0270405 A1 | 11/2011 | Geitz et al. |
| 2011/0270410 A1 | 11/2011 | Stack et al. |
| 2011/0275891 A1 | 11/2011 | Shemi |
| 2011/0276091 A1 | 11/2011 | Melanson et al. |
| 2011/0288080 A1 | 11/2011 | Saulnier et al. |
| 2011/0295054 A1 | 12/2011 | Aldridge et al. |
| 2011/0295055 A1 | 12/2011 | Albrecht et al. |
| 2011/0295151 A1 | 12/2011 | Bakos et al. |
| 2011/0295286 A1 | 12/2011 | Harris et al. |
| 2011/0301156 A1 | 12/2011 | Frank et al. |
| 2011/0301353 A1 | 12/2011 | Tang et al. |
| 2011/0307075 A1 | 12/2011 | Sharma |
| 2011/0320219 A1 | 12/2011 | Dang |
| 2012/0003204 A1 | 1/2012 | Park et al. |
| 2012/0003634 A1 | 1/2012 | Frumkin et al. |
| 2012/0004676 A1 | 1/2012 | Vargas |
| 2012/0029550 A1 | 2/2012 | Forsell |
| 2012/0029635 A1 | 2/2012 | Schoenhoeffer et al. |
| 2012/0041465 A1 | 2/2012 | Shalon |
| 2012/0046718 A1 | 2/2012 | Singh |
| 2012/0058107 A1 | 3/2012 | Tang et al. |
| 2012/0059431 A1 | 3/2012 | Williams et al. |
| 2012/0065571 A1 | 3/2012 | Thompson et al. |
| 2012/0083819 A1 | 4/2012 | Wang et al. |
| 2012/0087910 A1 | 4/2012 | Trieu et al. |
| 2012/0088300 A1 | 4/2012 | Melton et al. |
| 2012/0088967 A1 | 4/2012 | Laufer et al. |
| 2012/0089170 A1 | 4/2012 | Dominguez |
| 2012/0095384 A1 | 4/2012 | Babkes et al. |
| 2012/0095385 A1 | 4/2012 | Dominguez et al. |
| 2012/0095483 A1 | 4/2012 | Babkes et al. |
| 2012/0095494 A1 | 4/2012 | Dominguez et al. |
| 2012/0095495 A1 | 4/2012 | Babkes et al. |
| 2012/0095497 A1 | 4/2012 | Babkes et al. |
| 2012/0108590 A1 | 5/2012 | Birtalan et al. |
| 2012/0110682 A1 | 5/2012 | Mather et al. |
| 2012/0116286 A1 | 5/2012 | Williams et al. |
| 2012/0121594 A1 | 5/2012 | Smith |
| 2012/0142760 A1 | 6/2012 | Kieffer et al. |
| 2012/0148540 A1 | 6/2012 | Freeman et al. |
| 2012/0157470 A1 | 6/2012 | Catron et al. |
| 2012/0157495 A1 | 6/2012 | Munchhof et al. |
| 2012/0158026 A1 | 6/2012 | Behan |
| 2012/0179086 A1 | 7/2012 | Shank et al. |
| 2012/0184541 A1 | 7/2012 | Baell et al. |
| 2012/0184893 A1 | 7/2012 | Thompson et al. |
| 2012/0184967 A1 | 7/2012 | Levine et al. |
| 2012/0208786 A1 | 8/2012 | Lyles et al. |
| 2012/0209400 A1 | 8/2012 | Schurr |
| 2012/0213731 A1 | 8/2012 | Faustman |
| 2012/0214848 A1 | 8/2012 | Zhang et al. |
| 2012/0215152 A1 | 8/2012 | Levine et al. |
| 2012/0232460 A1 | 9/2012 | Raven et al. |
| 2012/0232577 A1 | 9/2012 | Birk et al. |
| 2012/0245087 A1 | 9/2012 | Jackson et al. |
| 2012/0245553 A1 | 9/2012 | Raven et al. |
| 2012/0253259 A1 | 10/2012 | Belhe et al. |
| 2012/0253260 A1 | 10/2012 | Belhe et al. |
| 2012/0253529 A1 | 10/2012 | Carlson et al. |
| 2012/0258126 A1 | 10/2012 | Schoeller et al. |
| 2012/0263781 A1 | 10/2012 | Chancellor et al. |
| 2012/0271217 A1 | 10/2012 | Stack et al. |
| 2012/0277210 A1 | 11/2012 | Catron et al. |
| 2012/0277271 A1 | 11/2012 | Nadeson et al. |
| 2012/0296365 A1 | 11/2012 | Nguyen |
| 2012/0301475 A1 | 11/2012 | Shemesh et al. |
| 2012/0302602 A1 | 11/2012 | Frank et al. |
| 2012/0309775 A1 | 12/2012 | Cheng et al. |
| 2013/0005724 A1 | 1/2013 | Lassalle et al. |
| 2013/0005964 A1 | 1/2013 | Luzzio et al. |
| 2013/0006382 A1 | 1/2013 | Behan |
| 2013/0006672 A1 | 1/2013 | Dang |
| 2013/0011332 A1 | 1/2013 | Boyden et al. |
| 2013/0013084 A1* | 1/2013 | Birk ................. A61F 5/0079 623/23.68 |
| 2013/0030350 A1 | 1/2013 | Albrecht et al. |
| 2013/0030351 A1 | 1/2013 | Belhe et al. |
| 2013/0034844 A1 | 2/2013 | Boyle et al. |
| 2013/0035576 A1 | 2/2013 | O'Grady et al. |
| 2013/0041424 A1 | 2/2013 | Neisz |
| 2013/0071466 A1 | 3/2013 | Chancellor et al. |
| 2013/0079329 A1 | 3/2013 | Hood et al. |
| 2013/0079345 A1 | 3/2013 | Eickhoff et al. |
| 2013/0079603 A1 | 3/2013 | Vargas |
| 2013/0133091 A1 | 5/2013 | Korman et al. |
| 2013/0156726 A1 | 6/2013 | Ichim et al. |
| 2013/0164371 A1 | 6/2013 | Imran |
| 2013/0164372 A1 | 6/2013 | Imran |
| 2013/0164373 A1 | 6/2013 | Imran |
| 2013/0165372 A1 | 6/2013 | Imran |
| 2013/0165373 A1 | 6/2013 | Imran |
| 2013/0165772 A1 | 6/2013 | Traverso et al. |
| 2013/0165859 A1 | 6/2013 | Imran |
| 2013/0171244 A1 | 7/2013 | Imran |
| 2013/0171245 A1 | 7/2013 | Imran |

(56) References Cited

U.S. PATENT DOCUMENTS

| | | |
|---|---|---|
| 2013/0171246 A1 | 7/2013 | Imran |
| 2013/0171247 A1 | 7/2013 | Imran |
| 2013/0172257 A1 | 7/2013 | Imran |
| 2013/0177527 A1 | 7/2013 | Imran |
| 2013/0177550 A1 | 7/2013 | Imran |
| 2013/0178472 A1 | 7/2013 | Bellevergue et al. |
| 2013/0189240 A1 | 7/2013 | Cho et al. |
| 2013/0189353 A1 | 7/2013 | Imran |
| 2013/0190675 A1 | 7/2013 | Sandoski |
| 2013/0195970 A1 | 8/2013 | Imran |
| 2013/0197421 A1 | 8/2013 | Sharvit et al. |
| 2013/0204208 A1 | 8/2013 | Olson et al. |
| 2013/0210800 A1 | 8/2013 | Nair et al. |
| 2013/0218289 A1 | 8/2013 | Gao et al. |
| 2013/0245068 A1 | 9/2013 | Kwon et al. |
| 2013/0247233 A1 | 9/2013 | Gaitanaris et al. |
| 2013/0253408 A1 | 9/2013 | Krueger et al. |
| 2013/0273061 A1 | 10/2013 | Huang et al. |
| 2013/0274659 A1 | 10/2013 | Imran et al. |
| 2013/0274789 A1 | 10/2013 | Brooks et al. |
| 2013/0281911 A1 | 10/2013 | Babkes et al. |
| 2013/0289139 A1 | 10/2013 | Radford et al. |
| 2013/0289466 A1 | 10/2013 | Babkes et al. |
| 2013/0296764 A1 | 11/2013 | Stack et al. |
| 2013/0296913 A1 | 11/2013 | Foote et al. |
| 2013/0310727 A1 | 11/2013 | Stack et al. |
| 2013/0310833 A1 | 11/2013 | Brown et al. |
| 2013/0324902 A1 | 12/2013 | Miller et al. |
| 2013/0324906 A1 | 12/2013 | Neisz et al. |
| 2013/0324907 A1 | 12/2013 | Huntley et al. |
| 2013/0331359 A1 | 12/2013 | Yun et al. |
| 2013/0331383 A1 | 12/2013 | Saulnier et al. |
| 2013/0331759 A1 | 12/2013 | Neisz et al. |
| 2013/0337563 A1 | 12/2013 | Phan et al. |
| 2013/0338741 A1 | 12/2013 | Singh |
| 2013/0344173 A1 | 12/2013 | Fogelman et al. |
| 2013/0345670 A1 | 12/2013 | Rajagopalan et al. |
| 2014/0004175 A1 | 1/2014 | Kliger et al. |
| 2014/0005190 A1 | 1/2014 | Baell et al. |
| 2014/0018719 A1* | 1/2014 | Chamorro, III ...... A61F 5/0076 604/8 |
| 2014/0024114 A1 | 1/2014 | Melton et al. |
| 2014/0024991 A1 | 1/2014 | Chin |
| 2014/0039250 A1 | 2/2014 | Bachmann et al. |
| 2014/0044641 A1 | 2/2014 | Toporik et al. |
| 2014/0044736 A1 | 2/2014 | Hammers |
| 2014/0045815 A1 | 2/2014 | Hood et al. |
| 2014/0051645 A1 | 2/2014 | Matschiner et al. |
| 2014/0081416 A1 | 3/2014 | Clerc et al. |
| 2014/0094734 A1 | 4/2014 | Stack et al. |
| 2014/0121585 A1 | 5/2014 | Baker et al. |
| 2014/0142720 A1 | 5/2014 | Stack et al. |
| 2014/0180188 A1 | 6/2014 | Chin et al. |
| 2014/0180192 A1 | 6/2014 | Ortiz et al. |
| 2014/0194806 A1 | 7/2014 | Belhe et al. |
| 2014/0194917 A1 | 7/2014 | Sharma |
| 2014/0200502 A1 | 7/2014 | Belhe et al. |
| 2014/0213960 A1 | 7/2014 | Belhe et al. |
| 2014/0221899 A1 | 8/2014 | Vargas |
| 2014/0243992 A1 | 8/2014 | Walsh et al. |
| 2014/0276336 A1 | 9/2014 | Sharma |
| 2015/0196412 A1 | 7/2015 | Roselauf et al. |
| 2015/0196419 A1 | 7/2015 | Roselauf et al. |
| 2016/0049149 A1 | 2/2016 | Lacher |
| 2016/0095733 A1 | 4/2016 | Sharma et al. |
| 2017/0312111 A1 | 11/2017 | Sharma et al. |
| 2018/0263803 A1 | 9/2018 | Sharma et al. |
| 2020/0015990 A1 | 1/2020 | Sharma et al. |
| 2020/0206006 A1 | 7/2020 | Sharma |
| 2021/0015645 A1 | 1/2021 | Sharma et al. |

FOREIGN PATENT DOCUMENTS

| | | |
|---|---|---|
| AU | 2012211067 A1 | 8/2013 |
| AU | 2010232570 B2 | 11/2013 |
| AU | 2014200766 A1 | 3/2014 |
| AU | 2012315575 A1 | 4/2014 |
| CA | 2756991 A1 | 10/2010 |
| CN | 1575155 A | 2/2005 |
| CN | 1713870 A | 12/2005 |
| CN | 2756991 Y | 2/2006 |
| CN | 102014763 A | 4/2011 |
| CN | 102387762 A | 3/2012 |
| CN | 102470038 A | 5/2012 |
| CN | 102551938 A | 7/2012 |
| CN | 102824239 A | 12/2012 |
| CN | 103635212 A | 3/2014 |
| CN | 105263439 A | 1/2016 |
| EP | 0278937 B1 | 10/1993 |
| EP | 0480667 B1 | 3/1996 |
| EP | 0774571 A1 | 5/1997 |
| EP | 0754017 B1 | 6/2002 |
| EP | 0843538 B1 | 6/2002 |
| EP | 1420730 A2 | 5/2004 |
| EP | 1492477 A1 | 1/2005 |
| EP | 1492478 A1 | 1/2005 |
| EP | 2451411 A2 | 5/2012 |
| EP | 2521513 A1 | 11/2012 |
| EP | 2667910 A2 | 12/2013 |
| EP | 2413849 B1 | 7/2014 |
| EP | 2760502 A1 | 8/2014 |
| JP | 04-212348 A | 8/1992 |
| JP | 0672569 B2 | 9/1994 |
| JP | 2005-500127 A | 1/2005 |
| JP | 2010-523262 A | 7/2010 |
| JP | 2011-152425 A | 8/2011 |
| JP | 2012-501812 A | 1/2012 |
| JP | 2012-522595 A | 9/2012 |
| JP | 2015-534887 A | 12/2015 |
| JP | 6725691 B2 | 7/2020 |
| KR | 10-1065368 B1 | 9/2011 |
| KR | 2012-0008492 A | 1/2012 |
| WO | 88/00027 A1 | 1/1988 |
| WO | 91/01117 A1 | 2/1991 |
| WO | 94/01165 A1 | 1/1994 |
| WO | 00/12027 A1 | 3/2000 |
| WO | 00/32137 A1 | 6/2000 |
| WO | 00/42949 A2 | 7/2000 |
| WO | 01/45485 A2 | 6/2001 |
| WO | 01/49359 A1 | 7/2001 |
| WO | 02/96327 A2 | 12/2002 |
| WO | 03/17882 A2 | 3/2003 |
| WO | 03/86246 A1 | 10/2003 |
| WO | 03/86247 A1 | 10/2003 |
| WO | 03/86360 A1 | 10/2003 |
| WO | 03/94784 A2 | 11/2003 |
| WO | 03/94785 A1 | 11/2003 |
| WO | 2004/049982 A2 | 6/2004 |
| WO | 2004/064680 A1 | 8/2004 |
| WO | 2004/064685 A1 | 8/2004 |
| WO | 2004/069331 A2 | 8/2004 |
| WO | 2004/069332 A1 | 8/2004 |
| WO | 2004/087014 A2 | 10/2004 |
| WO | 2004/087233 A2 | 10/2004 |
| WO | 2006/064503 A2 | 6/2006 |
| WO | 2007/007339 A2 | 1/2007 |
| WO | 2007/072469 A2 | 6/2007 |
| WO | 2008/023374 A2 | 2/2008 |
| WO | 2008/112894 A1 | 9/2008 |
| WO | 2008/121409 A1 | 10/2008 |
| WO | 2008/121831 A1 | 10/2008 |
| WO | 2008/154450 A1 | 12/2008 |
| WO | 2010/115011 A1 | 10/2010 |
| WO | 2010/128495 A1 | 11/2010 |
| WO | 2011/006098 A2 | 1/2011 |
| WO | 2011/085234 A1 | 7/2011 |
| WO | 2011/159271 A1 | 12/2011 |
| WO | 2012/068377 A1 | 5/2012 |
| WO | 2012/103531 A2 | 8/2012 |
| WO | 2013/049779 A1 | 4/2013 |

(56) References Cited

FOREIGN PATENT DOCUMENTS

| WO | 2014/113483 A1 | 7/2014 |
|---|---|---|
| WO | 2014/153267 A2 | 9/2014 |
| WO | 2015/071496 A1 | 5/2015 |
| WO | 2015/200554 A1 | 12/2015 |
| WO | 2016/049149 A2 | 3/2016 |
| WO | 2017/013266 A1 | 1/2017 |
| WO | 2017/132676 A1 | 8/2017 |
| WO | 2017/189682 A1 | 11/2017 |

OTHER PUBLICATIONS

European Application No. 18162640.1—Search Report dated Apr. 16, 2018.
First Office Action for Application No. CN 201080068476, dated Sep. 2, 2014.
International Preliminary Report on Patentability received for PCT Patent Application No. PCT/US2014/029846, dated Sep. 24, 2015, 16 pages.
International Preliminary Report on Patentability received for PCT Patent Application No. PCT/US2015/051668, dated Apr. 6, 2017, 10 pages.
International Preliminary Report on Patentability received for PCT Patent Application No. PCT/US2016/028509, dated Apr. 5, 2018, 7 pages.
International Preliminary Report on Patentability received for PCT Patent Application No. PCT/US2017/029571, dated Nov. 8, 2018, 12 pages.
International Search Report—Application No. PCT/US2017/029571 dated Sep. 11, 2017.
International Search Report and Written Opinion received for PCT Patent Application No. PCT/US2016/028509, dated Aug. 12, 2016, 8 pages.
International Search Report for PCT/US2002/027177, dated Feb. 14, 2003.
International Search Report for PCT/US2003/038238, dated Oct. 14, 2004.
International Search Report for PCT/US2010/038444, dated Sep. 16, 2010.
International Search Report for PCT/US2015/051668, dated Apr. 19, 2016.
International Written Opinion received for PCT Patent Application No. PCT/US2014/029846, dated Apr. 2, 2015 14 pages.
International Written Opinion received for PCT Patent Application No. PCT/US2015/051668, dated Apr. 19, 2016, 8 pages.
International Written Opinion received for PCT Patent Application No. PCT/US2017/029571, dated Sep. 11, 2017, 10 pages.
Klausner et al., "Expandable gastroretentive dosage forms", Journal of Controlled Release 90:143-162 (2003).
Notice of Allowance dated Sep. 30, 2013 for U.S. Appl. No. 12/814,431.
Office Action dated Jan. 4, 2013 for U.S. Appl. No. 12/814,481.
Office Action dated May 29, 2012 for U.S. Appl. No. 12/814,481.
Second Office Action for Application No. CN 201080068476, dated Jun. 3, 2015.
Sun et al., "Intestinal electric stimulation decreases fat absorption in rats: Therapeutic potential for obesity", Obes Res. Aug. 2004; 12(8):1235-42.
Supplementary Partial European Search Report for EP20100853335, dated Nov. 5, 2014.
Third Office Action for Application No. CN 201080068476, dated Nov. 13, 2015.
U.S. Pat. No. 8,668,662, Mar. 2014, Levine (withdrawn).

\* cited by examiner

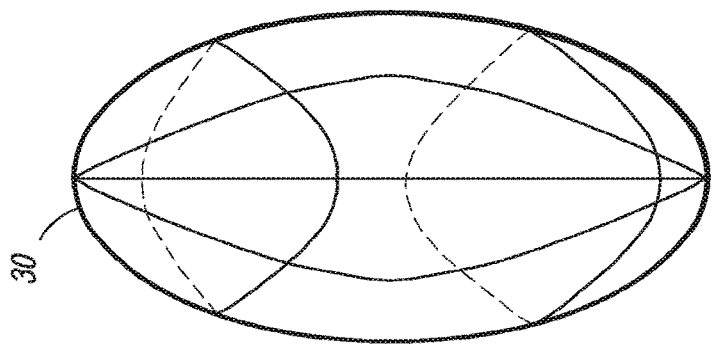
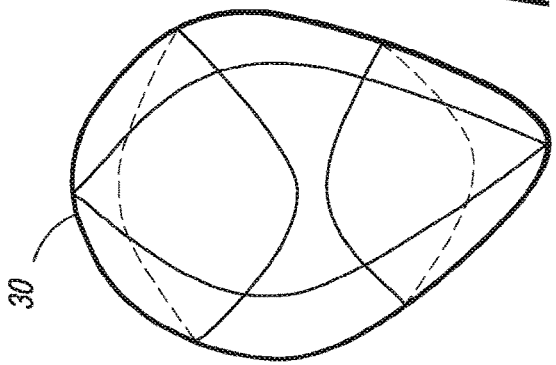
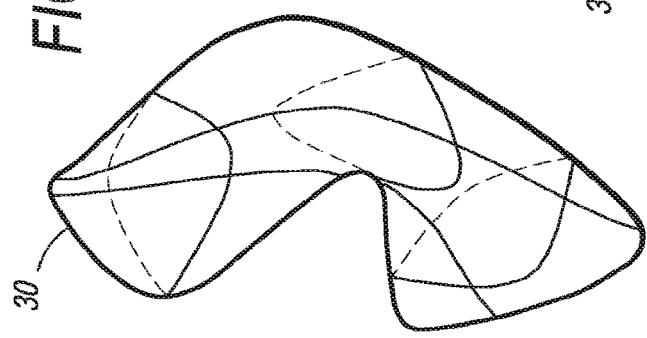
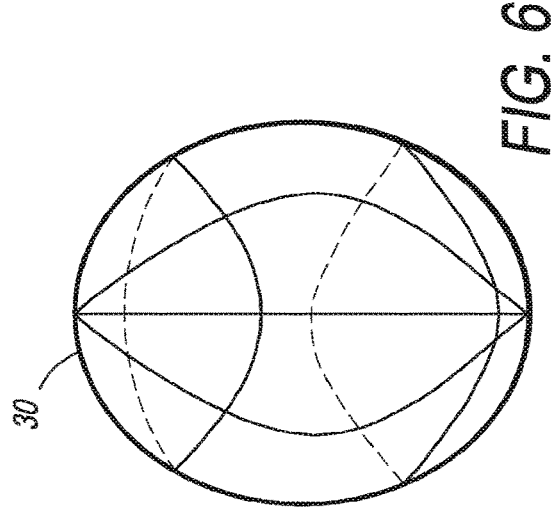
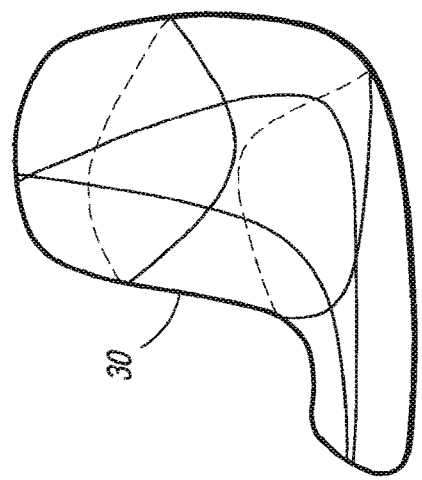
FIG. 6
FIG. 6A
FIG. 6B
FIG. 6C
FIG. 6D

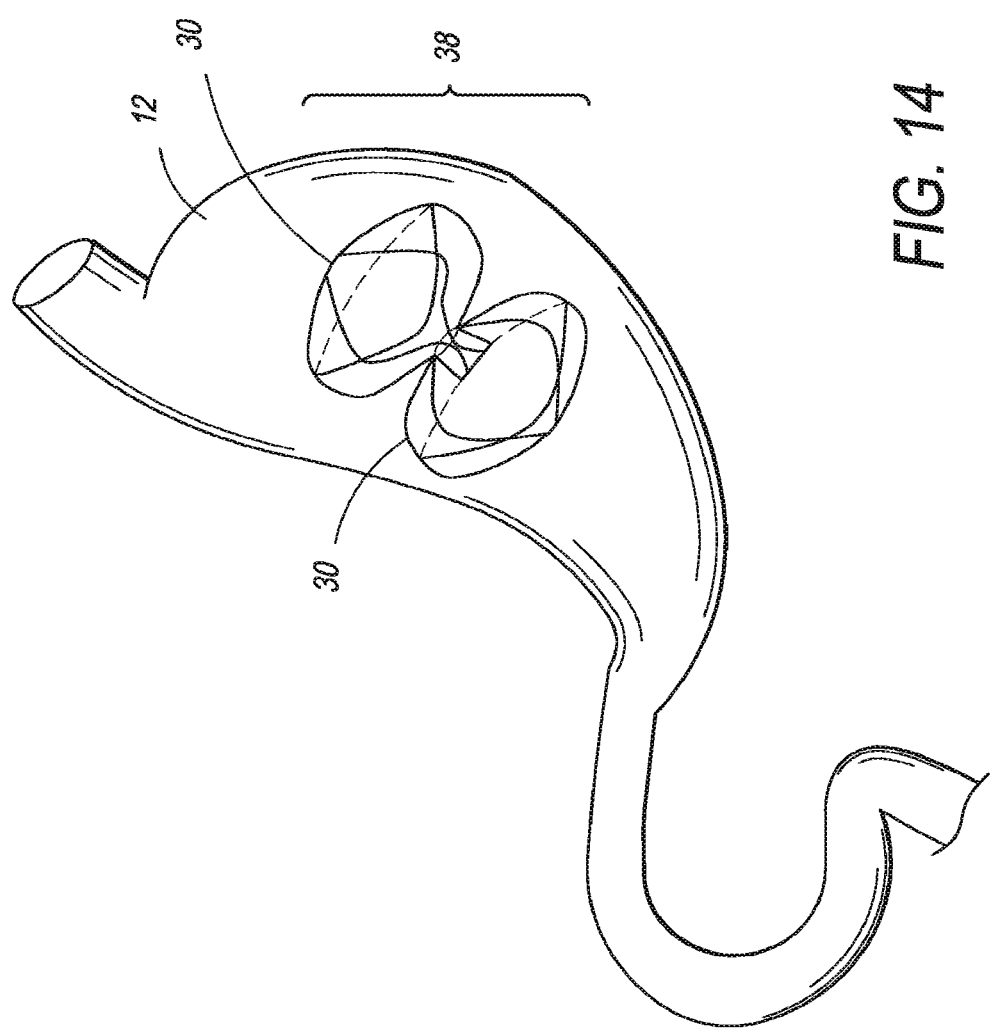

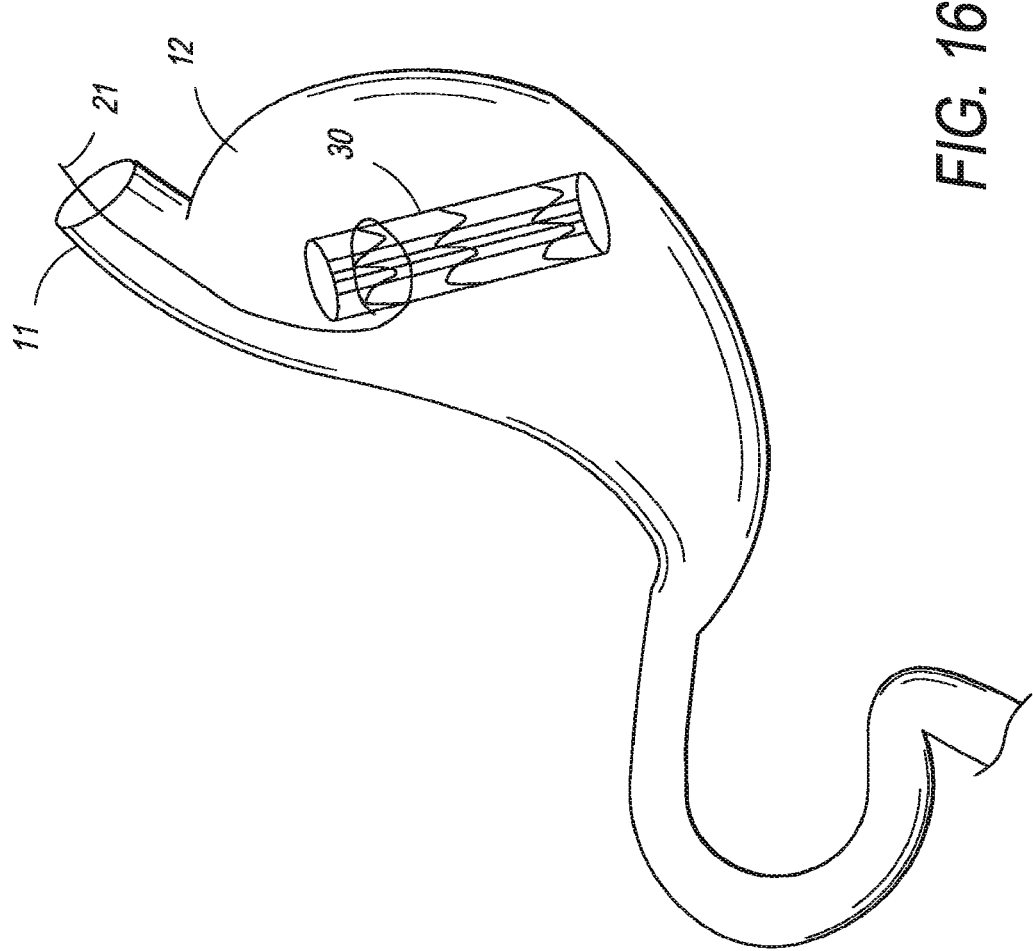

INTRAGASTRIC DEVICE FOR TREATING OBESITY

CROSS-REFERENCE TO RELATED APPLICATION

This application is a continuation of U.S. application Ser. No. 14/096,505, filed Dec. 4, 2013, which is a continuation of U.S. application Ser. No. 12/814,481, filed Jun. 13, 2010, now U.S. Pat. No. 8,628,554, both of which are incorporated herein by reference in their entireties for all purposes.

FIELD OF THE INVENTION

The present invention relates to a medical device useful in the treatment of obesity. More particularly, the present invention relates to an intragastric device of dynamic weight that reduces gastric volume and slows gastric emptying, thereby inducing satiety leading to patient weight loss.

BACKGROUND OF THE INVENTION

Obesity is a common condition and major public health problem in developed nations including the United States. As of 2009, more than two thirds of American adults, approximately 127 million people, were either overweight or obese. Data suggest that 300,000 Americans die prematurely from obesity-related complications each year. Many children in the United States are also either overweight or obese. Hence, the overall number of overweight Americans is expected to rise in the future. It has been estimated that obesity costs the United States approximately $100 billion annually in direct and indirect health care expenses and in lost productivity. This trend is also apparent in many other developed nations.

For adults, the body mass index (BMI) is used to determine if one is overweight or obese. A person's BMI is calculated by multiplying body weight in pounds by 703 and then dividing the total by height in inches squared. A person's BMI is expressed as kilograms per meter squared. An adult is considered overweight if his or her BMI is between 25 and 30 kg/m2. Obesity is defined as possessing a BMI between 30 and 40 kg/m2. A BMI greater than 30 kg/m2 is associated with significant co-morbidities. Morbid obesity is defined as possessing either a body weight more than 100 pounds greater than ideal or a BMI greater than 40 kg/m2. Approximately 5% of the U.S. population meets at least one of the criteria for morbid obesity. Morbid obesity is associated with many diseases and disorders including, for example: diabetes; hypertension; heart attack; stroke; dyslipidemia; sleep apnea; pickwickian syndrome; asthma; lower back and disc disease; weight-bearing osteoarthritis of the hips, knees, ankles and feet; thrombophlebitis and pulmonary emboli; intertriginous dermatitis; urinary stress incontinence; gastroesophageal reflux disease (GERD); gallstones; and, sclerosis and carcinoma of the liver. In women, infertility, cancer of the uterus, and cancer of the breast are additionally associated with morbid obesity. Taken together, the diseases associated with morbid obesity markedly reduce the odds of attaining an average lifespan. The sequelae raise annual mortality rates in affected people by a factor of 10 or more.

Current treatments for obesity include diet, exercise, behavioral treatments, medications, surgery (open and laparoscopic), and endoscopic devices. New drug treatments for obesity are currently being evaluated in clinical trials. However, a high efficacy pharmaceutical treatment has not yet been developed. Further, short-term and long-term side effects of current pharmaceutical treatments often concern consumers, pharmaceutical providers, and/or their insurers. Generally, diet or drug therapy programs have been consistently disappointing, failing to bring about significant, sustained weight loss in the majority of morbidly obese people.

Currently, most operations used to treat morbid obesity include gastric restrictive procedures, involving the creation of a small (e.g., 15-35 ml) upper gastric pouch that drains through a small outlet (e.g., 0.75-1.2 cm), setting in motion the body's satiety mechanism. About 15% of operations used to treat morbid obesity performed in the United States involve combining a gastric restrictive procedure with a malabsorptive procedure. Typical malabsorptive procedures divide small intestinal flow into a biliary-pancreatic conduit and a food conduit. Potential long-term side effects associated with abdominal surgical procedures include herniation and small bowel obstruction. In addition, long-term problems specific to bariatric procedures also include gastric outlet obstruction, marginal ulceration, protein malnutrition, and vitamin deficiency.

Other surgical strategies for treating obesity include endoscopic procedures, many of which are still in development. Endoscopic procedures and devices to produce gastric pouch and gastrojejunal anastomosis are used to replicate laparoscopic procedures. Endoscopically placed gastric balloons restrict gastric volume and result in satiety with smaller meals. For example, U.S. Pat. No. 7,172,613, assigned to Districlass Medical SA, describes "An intragastric device inserted by endoscopic path into a patient's stomach. The device includes a balloon or envelope having a specific nominal volume. The balloon is sealingly connected to connecting elements consisting of a disc forming a support base for the balloon against an inner wall of the stomach. The device also includes a flexible tube or catheter for connecting the balloon to a filling device and catching element integral with the tube or catheter. The connection elements enable a doctor to set and/or remove the balloon and to fix, either inside the patient's body, or subcutaneously the filling device and to be able to bring the balloon or envelope to its predetermined nominal volume."

The silicon intragastric balloon (IGB) has been developed as a temporary aid to achieve weight loss specifically for people who weigh 40% or more of their ideal weight and who have had unsatisfactory results in their treatment of obesity, despite being cared for by a multidisciplinary team. This treatment is also indicated for morbidly obese patients who have a high morbidity and mortality risk for surgery. The placement and removal of the IGB is an endoscopic procedure and the balloon is designed to float freely inside the stomach. The IGB technique reduces the volume of the stomach and leads to a premature feeling of satiety. However, use of IGBs did not show convincing evidence of a greater weight loss. The relative risks for minor complications, for example, gastric ulcers and erosions, were significantly raised. All inflatable IGB devices suffer from the problem of deterioration of the balloon over time. This deterioration can result in deflation with loss of efficacy and complications such as small bowel obstruction secondary to balloon migration. Due to loss of efficacy over time, IGB devices are recommended only for short (<6 month) durations. In addition, rapid inflation of the balloon poses the risk of esophageal or gastric perforations, both of which are surgical emergencies. Deaths have been reported in patients using IGB treatment.

Endoscopic procedures are also used to deploy mesh structures into the stomach in an effort to occupy stomach volume and create the artificial sensation of being full. For example, United States Patent Application Number 2007098039, assigned to Wilson-Cook Medical, Inc., describes "An intragastric device generally comprises a strip digestive-resistant mesh material that is operable between a first configuration and a second configuration. The first configuration is sufficiently small to permit introduction of the digestive-resistant mesh material into a gastric lumen of the mammal. The second configuration is sufficiently large to prevent the digestive-resistant mesh material from passing through the mammal's pylorus, thereby permitting the mesh member to act as an artificial bezoar."

Although endoscopically placed balloon structures can be effective, they are not without their associated risks and complications. Mesh structures are effective in occupying available gastric volume but they do not address gastric emptying. Migration and small bowel obstruction from such devices continue to remain a significant problem. Therefore, a need exists for an intragastric device to treat obesity that combines the benefits obtained through reducing stomach volume and slowing gastric emptying while remaining relatively safe. This device should limit side effects and be able to be deployed and removed in a non-invasive manner with relative ease. In addition, this new device should have the option of further treating obesity by including the benefits obtained by malabsorptive diversion procedures. The addition of this optional benefit would make the device effective in treating not only obesity, but type II diabetes as well.

SUMMARY OF THE INVENTION

The present invention is directed toward an intragastric device having a top and a bottom comprising: a structure having a pre-deployment shape with a first volume and a post-deployment shape with a second volume, wherein said first volume is less than said second volume; wherein, in said post-deployment shape, said device comprises at least one first opening proximate to the top of said device, each first opening defined by an area where a sum of the areas of the first openings is equal to a first area; wherein, in said post-deployment shape, said device comprises at least one second opening proximate to the bottom of said device, each second opening defined by an area where a sum of the areas of the second openings is equal to a second area; and wherein said first area is equal or larger than said second area. Optionally, the pre-deployment shape is linear, cylindrical, conical, a non-linear cylinder, spherical, a cube or a cuboid. Optionally, the structure comprises at least one of a mesh structure, a spiral structure, or a lattice structure.

Optionally, the wire mesh has a plurality of vertical and horizontal elements which, when expanded, create the at least one first opening and the at least one second opening. The wire mesh vertical and horizontal elements comprise at least one of a metal, an alloy, a polymer, a shape memory metal, or a shape memory polymer. The structure in enveloped by a partially perforated membrane having a surface area. The membrane comprises at least one of latex, parylene, polyurethane, polytetrafluoroethylene [PTFE], fluorinated ethylene-propylene, Dacron, or Polyethylene terephthalate (PET). The membrane has at least one first membrane opening, each first membrane opening having a first membrane opening area where a sum of said first membrane opening areas is equal to a third area, wherein said at least one first membrane opening is proximate to the top of the device.

The membrane has at least one second membrane opening, each second membrane opening having a second membrane opening area where a sum of said second membrane opening areas is equal to a fourth area, wherein said at least one second membrane opening is proximate to the bottom of the device and wherein the third area is equal or larger than the fourth area. The sum of said third area and fourth area is between one and ninety-nine percent of the membrane surface area. The membrane comprises at least one opening and wherein said opening has at least one valve that controls a directionality of flow of food or nutrients in and out of the device.

Optionally, the device is attached to a catheter, wherein said catheter is configured to induce a change from the pre-deployment shape to said post-deployment shape. A sleeve is attached to the bottom of said device, wherein said sleeve has a length sufficient to extend from the bottom of the device, through a patient's pylorus and duodenum, and into the patient's jejunum. The sleeve comprises at least one of latex, parylene, polyurethane, polytetrafluoroethylene [PTFE], fluorinated ethylene-propylene, Dacron, or Polyethylene terephthalate (PET). The device is configured to receive a second intragastric device.

In another embodiment, the present invention is directed toward an intragastric device having a top and a bottom comprising: a structure having a pre-deployment shape with a first volume and a post-deployment shape with a second volume, wherein said first volume is less than said second volume; wherein, in said post-deployment shape, said device comprises a plurality of first openings, each of said plurality of first openings defined by an area where a sum of the areas of the plurality of first openings is equal to a first area; wherein, in said post-deployment shape, said device comprises a plurality of second openings, each of said plurality of second openings defined by an area where a sum of the areas of the plurality of second openings is equal to a second area; wherein said first area is equal to larger than said second area; wherein said first area is closer to the top of device relative to the second area; and wherein said structure is enveloped by a membrane that does not cover said first area or said second area.

In another embodiment, the present invention is directed toward an intragastric device having a top and a bottom comprising: a structure having a pre-deployment shape with a first volume and a post-deployment shape with a second volume, wherein said first volume is less than said second volume; wherein, in said post-deployment shape, said device comprises at least one first opening to allow for entry of food into the device and at least one second opening to allow for exit of food from the device, wherein the device has a first weight when a patient is in a pre-feeding stage and a second weight when a patient is in a feeding or a post-feeding stage, and wherein the second weight is greater than the first weight. A patient is in a feeding stage when a patient is actively ingesting food or nutrients. This stage typically lasts between 1 minute and 1 hour. A patient is in a post-feeding stage after the patient has stopped ingesting food or nutrients and till most of the food or nutrients have exited the stomach. This stage normally lasts between 15 minutes and 4 hours and depends upon amount and type of food or nutrients ingested. This state is also affected by the health of patient and can be significantly prolonged in patients having gastric emptying abnormalities such as gastroparesis. A patient is in a pre-feeding stage between the end of post-feeding stage and the beginning of the feeding stage. The first opening is the same as the second opening. The first opening is different from the second opening. The device has a top half with a first weight and a bottom half with a second weight and wherein the first weight is different from the second weight.

BRIEF DESCRIPTION OF THE DRAWINGS

These and other features and advantages of the present invention will be appreciated as they become better understood by reference to the following detailed description when considered in connection with the accompanying drawings, wherein:

FIG. 6 is an illustration of one embodiment depicting a first exemplary configuration of the intragastric device post-deployment;

FIG. 6A is an illustration of one embodiment depicting a second exemplary configuration of the intragastric device post-deployment;

FIG. 6B is an illustration of one embodiment depicting a third exemplary configuration of the intragastric device post-deployment;

FIG. 6C is an illustration of one embodiment depicting a fourth exemplary configuration of the intragastric device post-deployment;

FIG. 6D is an illustration of one embodiment depicting another exemplary configuration of the intragastric device post-deployment;

FIG. 14 is an illustration of an exemplary fully deployed combined intragastric device in the stomach;

FIG. 16 is an illustration of an exemplary intragastric device being removed from the stomach;

DETAILED DESCRIPTION

Figure 1:
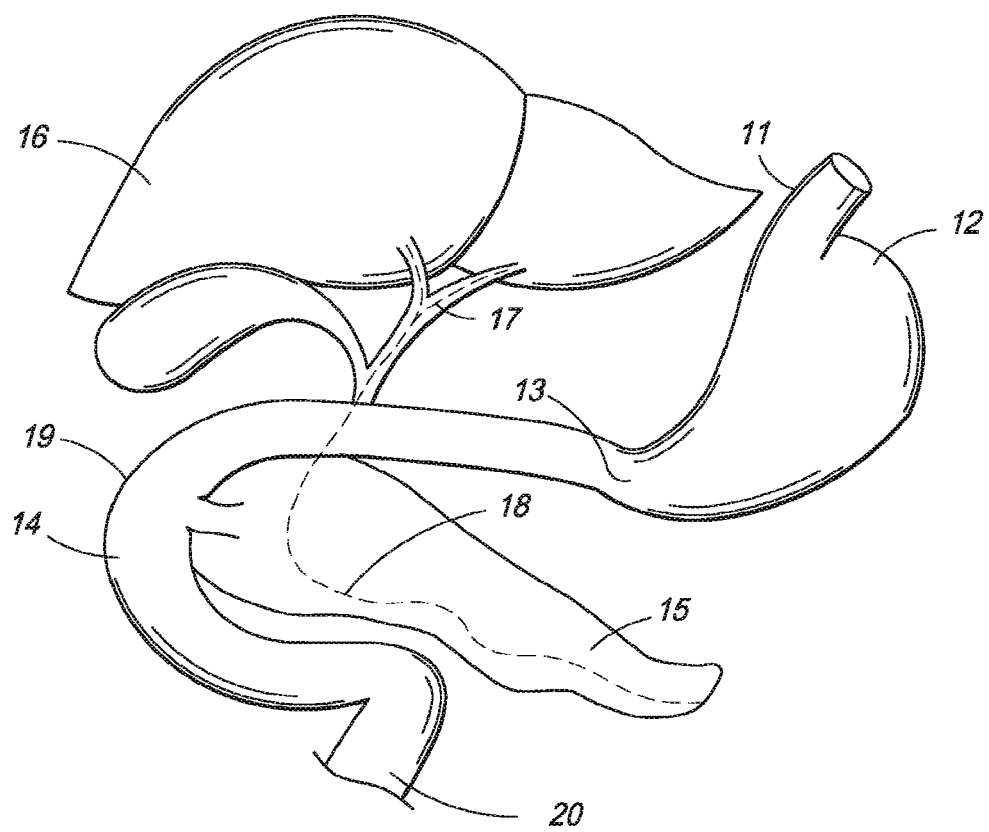
FIG. 1 is an illustration of the upper gastrointestinal system.

In one embodiment, the present invention is directed towards an intragastric device of dynamic weight used in obese patients to induce weight loss. In one embodiment, the intragastric device contains a non-inflatable wire mesh structure, or a spiral structure made of shape memory metal or shape memory polymer that changes from a pre-deployment compressed cylindrical shape to a post-deployment sphere, oval, kidney bean or any predefined shape of significant volume. The device changes back and forth from the pre-deployment shape to post-deployment shape by minimal mechanical force and/or temperature changes arising from the room temperature pre-deployment shape to the body temperature post-deployment shape. The device is delivered endoscopically to the stomach via a catheter. The device can be placed through the endoscope, over an endoscope or over a guidewire with endoscopic or fluoroscopic guidance/assistance.

The device has a pre-deployment compressed shape to facilitate insertion and post-deployment expanded shape that resides in the gastric lumen. Post-deployment volume of the device is significantly larger than pre-deployment volume. The post-deployment device occupies a significant volume in the stomach, thereby reducing available gastric volume available for storage of ingested food. This restricts the amount of food intake, inducing satiety and curbing one's appetite.

In one embodiment, the wire structure contains differently weighted material to assist in proper positioning within the stomach. In one embodiment, lighter weighted material is positioned at the top of the wire structure proximate to the top openings and heavier weighted material is positioned at the bottom of the structure, proximate to the bottom openings. This differential weighting insures that the device will be properly situated within the stomach to effectuate the intended effect of slower gastric emptying. In addition, the differential weighting provides for proper gastric positioning without the need of physically anchoring the wire mesh structure to the stomach wall. The differential weight property can also be provided by the ingested food material that enters the device and is selectively accumulated toward the bottom of the device facilitated by the gravitational pull. The wire mesh structure is free to move about within the stomach while still maintaining its correct top to bottom alignment facilitated by the gravitational pull.

In one embodiment, the present invention is directed toward a wire mesh or spiral structure with an exterior housing structure that is defined by openings, holes, voids or spaces of varying sizes. The wire mesh or spiral structure has larger spaces or openings within its upper portion and smaller spaces within its bottom portion. The larger or more spaces or openings within the upper portion of the device are preferably aligned with, and directed toward, the esophagus, the cardia, the fundus or the body of the stomach and the fewer or smaller spaces or openings within the bottom portion of the device are preferably aligned with, and directed toward, the gastric antrum or the intestines. These spaces or openings provide two additional benefits beyond the feeling of satiety provided by the expanded second configuration.

First, differential sizes or numbers resulting in differential surface area of the upper and lower openings enable the device to act like a time release capsule. The larger surface area of the openings toward the top two-thirds of the structure permit a larger volume of food to enter into the device, as compared to the volume of food permitted to leave the device via the smaller surface area of the openings that define the bottom of the device, thereby making the device a temporary storage unit with a delayed release of the nutrients. As the stomach grinds solid food into liquid food, or chyme, the chyme passes into and is sequestered inside the intragastric device. The chyme is then slowly released back into the stomach, thereby delaying gastric emptying and inducing satiety. The gastric emptying can also be controlled by varying both the number and size of these openings, holes, spaces or voids to differentially control the inflow and outflow of the food from the device. In essence, the ratio of the surface area of the inflow and the outflow as calculated by the size and the number of inflow and outflow opening controls the rate of emptying from the device and hence the gastric emptying.

An additional embodiment of the device has large holes or opening in the middle and smaller opening in the top and bottom halves, thereby allowing the partially digested food to enter in the middle portion with the option to leave from either the top or the bottom half. In another embodiment the top two-thirds of the device has an opening but the lower one-third of the device has a membrane without any openings than stores the partially digested food in the upright position as a bowl and release the food back through the same openings in the top two thirds of the device when the patient is supine. In addition, liquid foods, such as ice cream, will also be sequestered into the dependent portion of the device and released into the stomach more slowly at a later time.

Second, the varying shape, size and number of the openings or spaces in the wire mesh structure allow the device to store ingested food and undergo meal induced dynamic weight change. The device will have a greater weight during and post feeding resulting in an appropriately timed feeling of fullness or satiety. Heavier intra-gastric devices are associated with more satiety and weight loss however they have more side-effects such as nausea and abdominal pain. Slowly, as the food is released out of the device, the weight of the device will decrease over time and return to its baseline weight. Eventually, the device will have a lower weight during fasting, diminishing the side effects commonly associated with an intragastric device, improving patient tolerance. Conventional water filled intragastric balloons are heavier than air filled balloons resulting in a greater feeling of satiety and weight loss but patients suffer from increased side effects resulting higher intolerance and need for premature removal. Air filled balloons are lighter and therefore more tolerable, but are less effective in inducing satiety and hence weight loss. The present invention improves upon both devices by inducing a greater and more normalized feeling of satiety during feeding and post-feeding stage while reducing side effects during the fasting stage.

In another embodiment, the present invention is directed towards a wire mesh or spiral structure partially encompassed, housed, or otherwise enclosed by a membrane. When expanded into the second configuration, the membrane contains opening, holes, voids, or spaces proximate to the top of the device and holes proximate to the bottom of the device. The openings on the top of the device have larger surface area and are preferably aligned with, and directed toward, the esophagus, cardia, fundus or the body of the stomach and the openings at the bottom of the device have same or less surface area compared to the openings on the top and are preferably aligned with, and directed toward, the antrum or pylorus of the stomach or the small intestines. These openings provide two additional benefits beyond the feeling of satiety provided by the expanded second configuration.

First, the device with differentially sized membrane opening, holes or voids acts as a time release capsule. More food enters into the device from the large surface area of the openings at the top than exits from the smaller surface area of the openings at the bottom, resulting in a device that functions as a temporary storage unit with a delayed release of nutrients. As the stomach grinds solid food into liquid food, or chyme, the chyme is sequestered inside the wire mesh device. The chyme is then slowly released back into the stomach, thereby delaying gastric emptying and inducing satiety. In addition, liquid foods, such as ice cream, will also be sequestered into the dependent portion of the device and released back into the stomach more slowly.

Second, the two sets of openings in the wire mesh structure membrane allow the device to undergo dynamic weight change. The device will have a greater weight during and post feeding resulting in an appropriately timed feeling of fullness or satiety. Slowly, as the food exits the device, the weight of the device will decrease over time. Eventually, the device will have a lower weight during fasting, diminishing the side effects commonly associated with an intragastric device, such as nausea and pain. Conventional water filled intragastric balloons are heavier than air filled balloons resulting in a greater feeling of satiety but patients suffer from increased side effects. Air filled balloons are lighter and therefore more tolerable, but are less effective in inducing satiety. The present invention improves upon both devices by inducing a greater and more normalized feeling of satiety during the feeding and post-feeding stage while reducing the side effects.

In another embodiment, the wire mesh structure has portions that are completely covered by a membrane and some portions that are not, resulting in differential release of food. In one embodiment, the top and bottom of the wire mesh structure are completely covered by the membrane and the middle of the structure has openings in the membrane to allow the passage of food. In another embodiment, the wire mesh structure is 90-99% covered by the membrane, leaving only a small area for food passage, thereby increasing the time for gastric emptying. In another embodiment, the membrane covering the wire mesh structure has a ring of large openings in the upper hemisphere of the structure and a ring of smaller openings in the bottom hemisphere of the structure. In another embodiment, the membrane covering the wire mesh structure has more number of openings in the upper hemisphere of the structure and less number of openings in the bottom hemisphere of the structure. In another embodiment, the membrane covering the wire mesh structure has a greater surface area of openings in the upper hemisphere of the structure and lesser surface area of openings in the bottom hemisphere of the structure. This different configuration also results in delayed gastric emptying and dynamic weight change of the wire mesh structure.

Gastric fundus is involved in the release various gut hormones such as "hunger hormones", ghrelin, orexin and PYY 3-36, and "satiety hormones", e.g., leptin, obestatin, nesfatin-1. The release of these hormones is mediated by contact of gastric mucosa with various nutrients in the ingested food. Further, the membrane of the top portion of the wire mesh structure will prevent sequestered food from coming into contact with the gastric cardia and fundus. This results in physiological exclusion of the gastric cardia and fundus, a mechanism thought to play a role in satiety and weight loss and one of the mechanism in play in RGB gastric bypass surgery.

In another embodiment, layers of membrane act as a flap valve controlling the directionality of the movement of the food in the various portions of the intragastric device. Just like the size of the openings, the size, shape, position and directionality of the valves can be varied to achieve desired gastric emptying effect.

In another embodiment, a sleeve can be attached to the intragastric device, where the sleeve extends from the stomach through the duodenum and into the jejunum. The sleeve functions to transit the sequestered chyme from the wire mesh structure directly to the mid-jejunum. The sleeve therefore acts to bypass portions of the gastrointestinal (GI) tract in order to limit the absorption of specific materials in the intestine. The benefits provided by a sleeve are similar to those provided by Roux-en-Y gastric bypass surgery, namely, weight loss and improvement of type II diabetes. These benefits are accomplished in at least two ways.

First, bypass of the duodenum and proximal duodenum improves type II diabetes by changing the hormone release from the proximal portion of the small intestine. This may also induce weight loss by inhibiting or decreasing the release of pacreatico-biliary secretions and inducing maldigestion and malabsorption. Second, the sleeve acts to release undigested nutrients into the m id-jejunum, improving type II diabetes by changing the hormone release from the mid portion of the small intestine. This may induce weight loss by maldigestion and malabsorption of these nutrients. While conventional sleeve devices may perform certain of these functions, conventional sleeves must be anchored in the GI tract to avoid migration. Anchoring often results in complications, including infection, bleeding, perforation, and, if not anchored correctly, migration of the sleeve leading to possible obstruction and death. In the present invention, the sleeve is physically attached to the intragastric device, where the intragastric device serves as the anchor for the sleeve. This removes the need for the sleeve to be physically anchored to the GI tract, eliminating the associated complications. In addition, the current device offers functional advantages over conventional sleeves by concurrently controlling food and calorie intake, inducing satiety, and controlling gastric emptying, which is not accomplished by traditional sleeve devices.

In another embodiment the intragastric device has multiple opening, holes, voids or spaces in the top half and a membrane with at least one opening, hole, or void in the bottom half where the bottom opening directs the food preferentially into the sleeve device. In this embodiment, the bottom half of the intragastric device acts as a funnel, collecting all the food entering the device through the top half in the bottom half and preferentially releasing it into the sleeve which in turn will deliver the food/nutrients to the mid small intestine thus bypassing the proximal small intestine.

In one embodiment the entire intragastric device is covered by the membrane with opening that have valves throughout the device directing the food into the intragastric device where it get sequestered and is preferentially emptied through the opening in the bottom half of the device into the sleeve and delivering it to the mid small bowel thus bypassing the proximal small intestine. In this embodiment, the intragastric device sequesters the nutrients/food and, through the sleeve attachment, empties them into the mid small intestine.

The above two embodiments mimic Roux-en-Y gastric bypass (RGB) surgery by creating gastric restriction, isolation of gastric fundus and bypassing the proximal small intestine thus resulting in maximum weight loss and control of Type-II diabetes. In addition the device has ability to regulate gastric emptying in a manner that cannot be traditionally achieved by RGB gastric bypass surgery. The controlled and prolonged release of nutrients into the mid and distal small bowel will result in prolonged satiety via modulation of release of gut hormones such as "hunger hormones", ghrelin, orexin, and PYY 3-36, and "satiety hormones", e.g., leptin, obestatin, and nesfatin-1.

In one embodiment, a second intragastric device can be attached to an already deployed intragastric device, thereby increasing the volume occupied in the stomach. This serves to further limit the amount of food ingested by a patient and also further delays gastric emptying as food flows from one intragastric device into the other before releasing back into the stomach or into the attached sleeve device. This allows for tailoring the therapy to a specific patient's need by increasing or decreasing the volume of the intragastric devices. In addition, this allows for the possibility of step-wise increases or decreases in the device based therapy based on therapeutic response and side-effect profile. This is usually performed in the inflatable intragastric devices by instilling or removing fluids. However, such devices do not have the ability to regulate gastric emptying.

Another part of this invention is a removal device used to remove the intragastric device. The removal device is a catheter inserted per-orally or via an endoscope and passed through a proximal and optionally through a distal opening of the intragastric device. The catheter then engages and secures the proximal and distal end of the expanded intragastric device and the device is then constrained back into its pre-deployed shape using mechanical force. The reversion to its pre-deployed state in a shape memory device can be further facilitated by instillation of cold fluid into the intragastric device, lowering the temperature of the intragastric device.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 is an illustration of the upper gastrointestinal system. After swallowing, food passes rapidly through the esophagus 11 into the stomach 12. There, it is digested for a period of time and undergoes the process of dilution to an iso-osmotic concentration by grinding and mixing with gastric juices. The stomach 12 relaxes to accommodate the volume of ingested food. As the stomach 12 gets filled with food the sensation of fullness or satiety is generated by stretch receptors in the gastric wall and the person stops eating. The iso-osmotic food, known as chyme, then passes through the pylorus 13 into the duodenum 14. Passage of chyme into the duodenum 14 results in the release of enzyme rich pancreatic secretions from the pancreas 15 and bile salt rich biliary secretions from the liver 16. The biliary secretions travel through the common bile duct 17 where they combine with the pancreatic secretions arriving through the pancreatic duct 18 to form the ampulla of water 19. The ampulla of water 19 serves as the entry point for the secretions to be deposited into the duodenum 14. In the jejunum 20, the mixing of pancreatic and biliary secretions with the chyme results in the digestion of proteins, fats, and carbohydrates, which are then absorbed into the blood stream.

Figure 2:
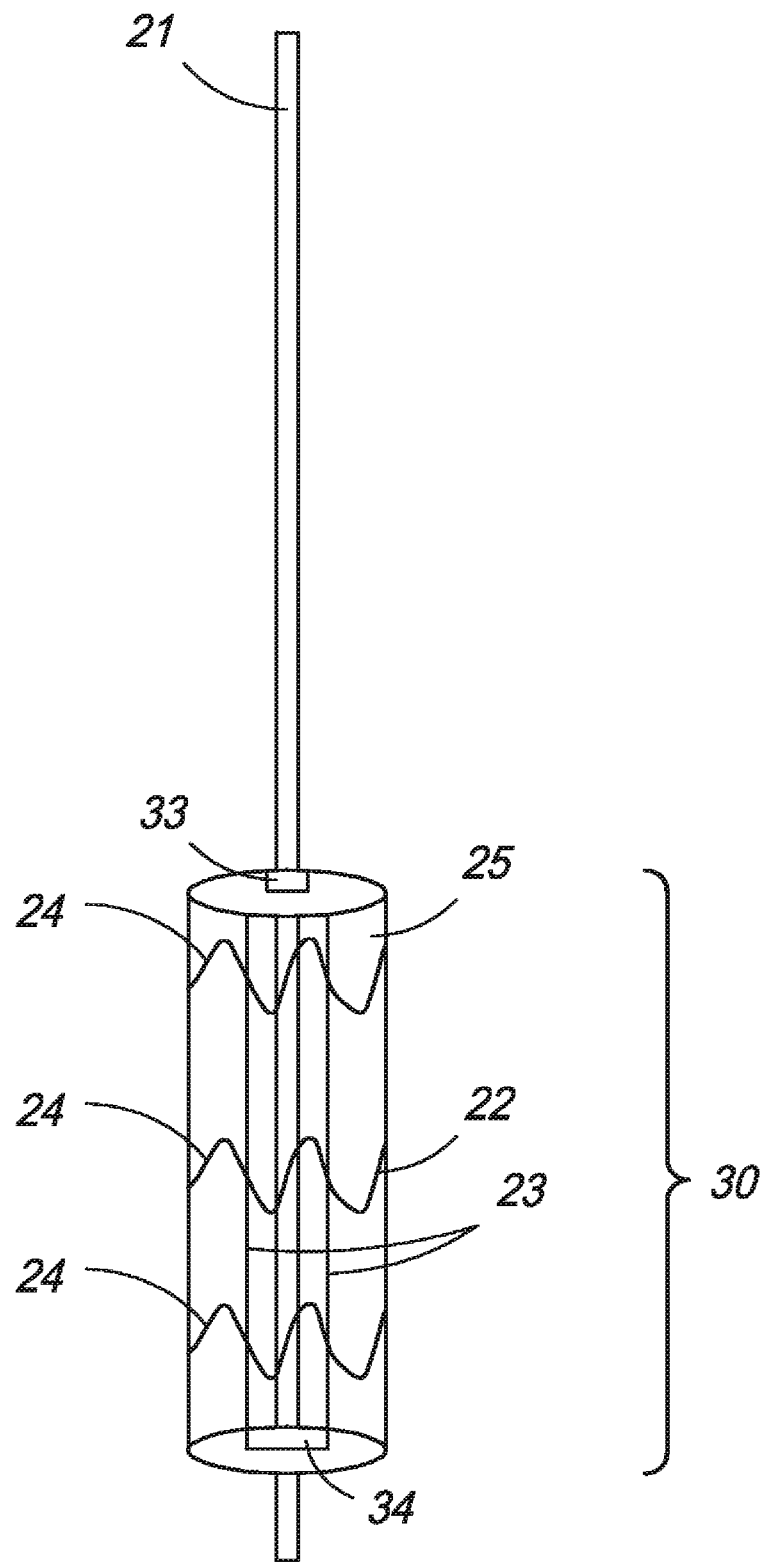
FIG. 2 is an illustration of one embodiment of the intragastric device in an exemplary pre-deployment configuration.

FIG. 2 is an illustration of one embodiment of the intragastric device 30 in the pre-deployment configuration. A catheter 21 holds the compressed wire mesh structure 22. The compressed wire mesh device is held in place by either a constraining catheter, sheath, or a silk suture or thread. The compressed wire mesh structure 22 is made of vertical elements 23 and horizontal elements 24. Optionally the intragastric device can be a metal spiral that is cylindrical, comparable to a spring, in constrained positioned and a spiral metal sphere in the deployed shape. In one embodiment, the vertical elements 23 and horizontal elements 24 comprise a metal. In another embodiment, the vertical elements 23 and horizontal elements 24 comprise an alloy. In another embodiment, the vertical elements 23 and horizontal elements 24 comprise a polymer. In yet another embodiment, the vertical elements 23 and horizontal elements 24 comprise a shape memory metal. In yet another embodiment, the vertical elements 23 and horizontal elements 24 comprise a shape memory alloy. In yet another embodiment, the vertical elements 23 and horizontal elements 24 comprise a shape memory polymer. In one embodiment, a weight 34 is positioned proximate to the bottom of the intragastric device. The weight serves to keep the intragastric device in the proper alignment when positioned in the stomach. Preferably, the weight is in a range of 1 to 500 grams, preferably between 10 and 50 grams. The catheter 21 has optional ports for passage of wire, contrast or an endoscope located in the center of the catheter shaft. One of ordinary skill in the art would appreciate the structure and configuration of a compressed structure within a catheter that, after removing a constraining sheath, is permitted to expand at a treatment location.

Figure 3:
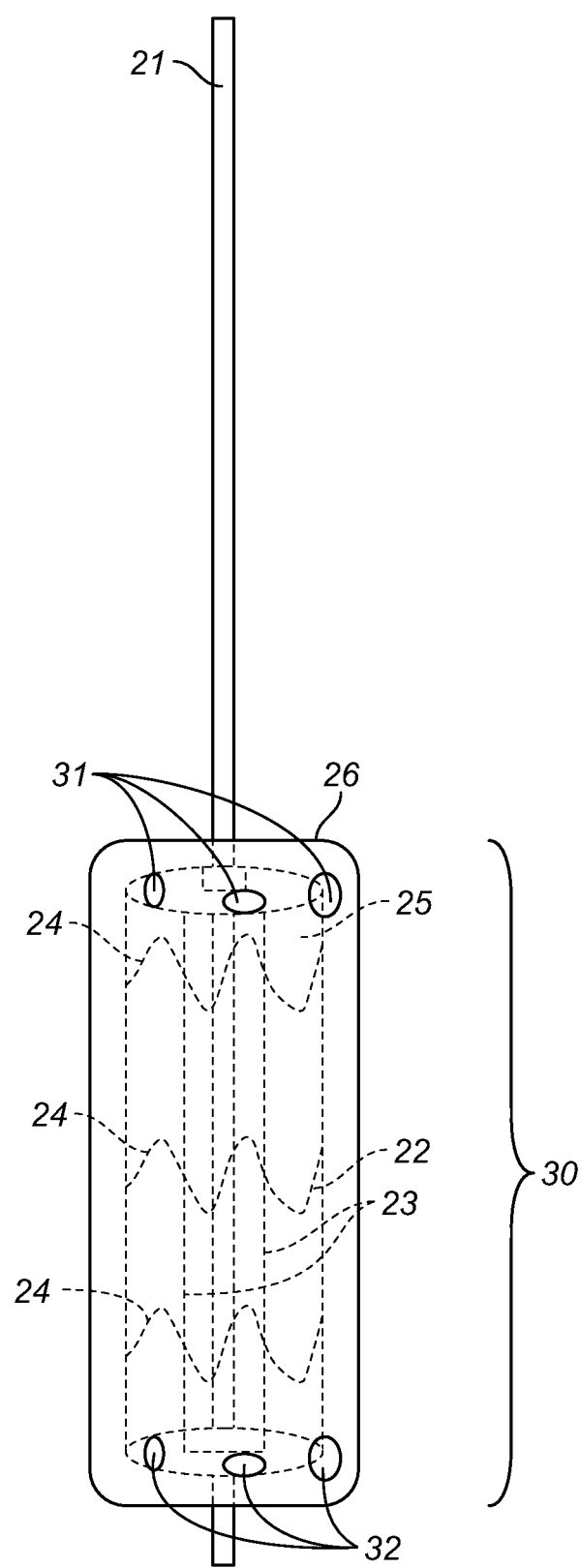
FIG. 3 is an illustration of another embodiment of the intragastric device in an exemplary pre-deployment configuration.

FIG. 3 is an illustration of another embodiment of the intragastric device 30 in the pre-deployment configuration. A catheter 21 holds the compressed wire mesh structure 22. The compressed wire mesh structure 22 is made of vertical elements 23 and horizontal elements 24. In one embodiment, the vertical elements 23 and horizontal elements 24 comprise metal. In another embodiment, the vertical elements 23 and horizontal elements 24 comprise an alloy. In another embodiment, the vertical elements 23 and horizontal elements 24 comprise a polymer. In yet another embodiment, the vertical elements 23 and horizontal elements 24 comprise a shape memory metal. In yet another embodiment, the vertical elements 23 and horizontal elements 24 comprise a shape memory alloy. In yet another embodiment, the vertical elements 23 and horizontal elements 24 comprise a shape memory polymer. In one embodiment, the compressed wire mesh structure 22 is partially enveloped by a membrane 26. The membrane 26 is made up of a digestive resistance material.

In one embodiment, the membrane 26 comprises latex. In another embodiment, the membrane 26 comprises parylene. In another embodiment, the membrane 26 comprises polyurethane. In another embodiment, the membrane 26 comprises polytetrafluoroethylene (PTFE). In another embodiment, the membrane 26 comprises fluorinated ethylene-propylene. In another embodiment, the membrane 26 comprises Dacron. In yet another embodiment, the membrane 26 comprises polyethylene terephthalate (PET). In one embodiment, the membrane 26 comprises openings 31 with larger surface area proximate the top of the intragastric device 30 for receiving chyme and openings 32 with a smaller surface area proximate the bottom of the intragastric device 30 for slow release of the sequestered chyme.

Figure 4:
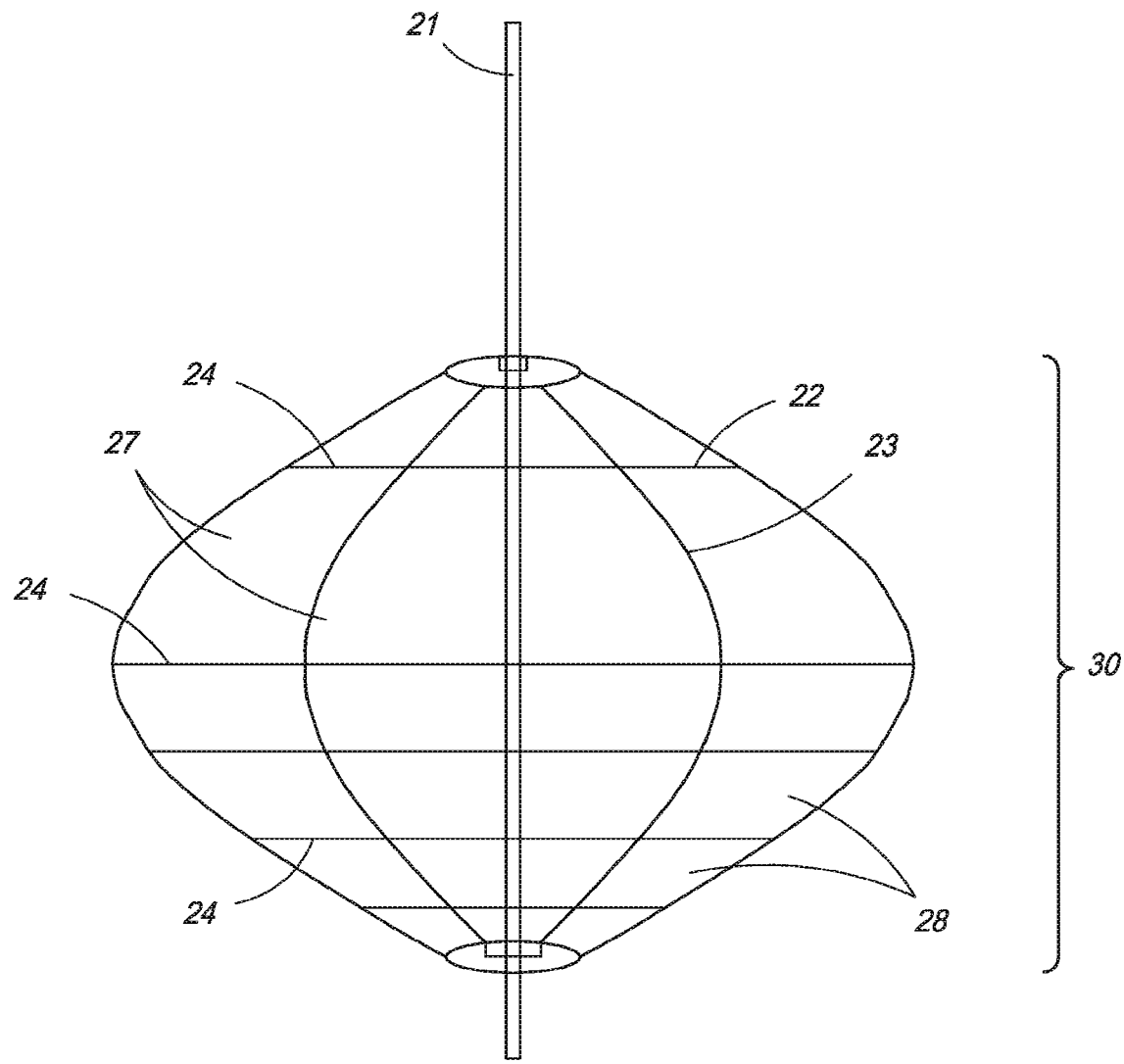
FIG. 4 is an illustration of one embodiment of the intragastric device in an exemplary post-deployment configuration.

FIG. 4 is an illustration of one embodiment of the intragastric device 30 in the post-deployment configuration. The catheter 21 is positioned into the stomach and the compressed wire mesh structure 22 is released. After deployment, the wire mesh structure 22 assumes its expanded configuration. This is achieved through the use of shape memory technology as the vertical elements 23 and horizontal elements 24 expand to assume their pre-defined, post-deployment shapes. The expansion of the vertical elements 23 and horizontal elements 24 creates the spaces 27 with larger surface area proximate the top of the intragastric device 30 and the spaces 28 with similar or smaller surface area proximate the bottom of the intragastric device 30. These differing sized spaces slow gastric emptying and induce a longer period of satiety.

The spaces within the structure can range in size between 1 μm and 10 cm, preferably between 1 mm and 5 cm and most preferably between 5 mm and 10 mm. The spaces at the top of the structure can be same size as the spaces at the bottom of the structure. Alternatively, spaces at the bottom of the structure are smaller but no smaller than 50% of the larger openings at the top of the structure, otherwise food will accumulate in the device and interfere with its functionality. In one embodiment, the gastric emptying is achieved by having each opening at the top have the same surface area as each opening at the bottom. In this embodiment, the number of openings at the bottom of the structure will be less than the number of openings at the top of the structure. If one wished to delay gastric emptying by 50%, the number of openings in the bottom will be approximately 50% of the number of the openings in the top of the structure. Alternatively, the openings at the top can have a larger surface area than the openings at the bottom and, if one wished to delay gastric emptying by 50%, the total surface area of the openings in the bottom will be approximately 50% of the total surface area of the openings in the top of the structure.

After deployment, the catheter 21 is removed, leaving the deployed intragastric device 30 in the stomach. The post-deployment intragastric device 30 occupies the gastric lumen thereby decreasing the effective volume available to accommodate ingested food. The post-deployment intragastric device 30 presses upon the gastric wall, stimulating the stretch receptors and inducing the sensation of fullness or satiety. A sphere is the most effective embodiment of the device as it has the most volume for a given pre-deployment length and surface area.

In various possible embodiments, the pre and post-deployment configurations of the intragastric device contain the following attributes:

| Pre-deployment length (cm) | Post-deployment radius (cm) | Post-deployment volume (cc) |
|---|---|---|
| 6 | 1.9 | 29 |
| 9 | 2.9 | 98 |
| 12 | 3.8 | 233 |
| 15 | 4.8 | 456 |
| 18 | 5.7 | 787 |
| 20 | 6.4 | 1080 |
| 25 | 8.0 | 2109 |
| 30 | 9.5 | 3645 |
| 40 | 12.7 | 8639 |
| 50 | 15.9 | 16873 |

The post-deployment radius (r) is equal to pre-deployment length (l) divided by pi (π) and the post-deployment volume (v) is equal to 4 13/3 π2.

Figure 5:
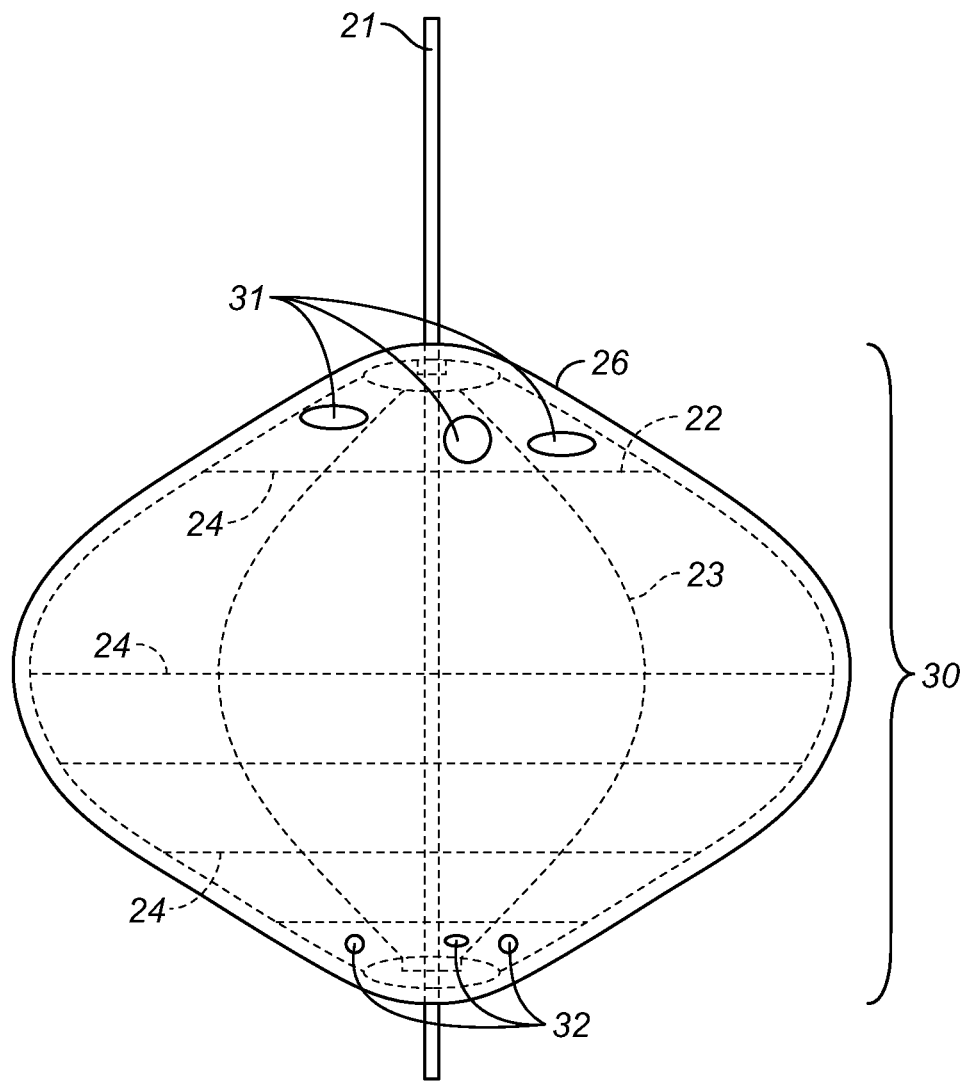
FIG. 5 is an illustration of another embodiment of the intragastric device in an exemplary post-deployment configuration.

FIG. 5 is an illustration of another embodiment of the intragastric device 30 in the post-deployment configuration. The catheter 21 is positioned into the stomach and the compressed wire mesh structure 22 is released. After deployment, the wire mesh structure 22 assumes its expanded configuration. This is achieved through the use of shape memory technology as the vertical elements 23 and horizontal elements 24 expand to assume their pre-defined, post-deployment shapes. The enveloping membrane 26 gives the intragastric device the quality of being partially permeable to gastric fluids. Large holes 31 are positioned proximate the top of the intragastric device 30 and small holes 32 are positioned proximate the bottom of the intragastric device 30. These differing sized holes in the membrane 26 allow for slowing of gastric emptying. After deployment, the catheter 21 is removed, leaving the deployed intragastric device 30 in the stomach. The post-deployment intragastric device 30 occupies the gastric lumen thereby decreasing the effective volume available to accommodate ingested food. The post-deployment intragastric device 30 presses upon the gastric wall, stimulating the stretch receptors and inducing the sensation of fullness or satiety.

Figure 5B:
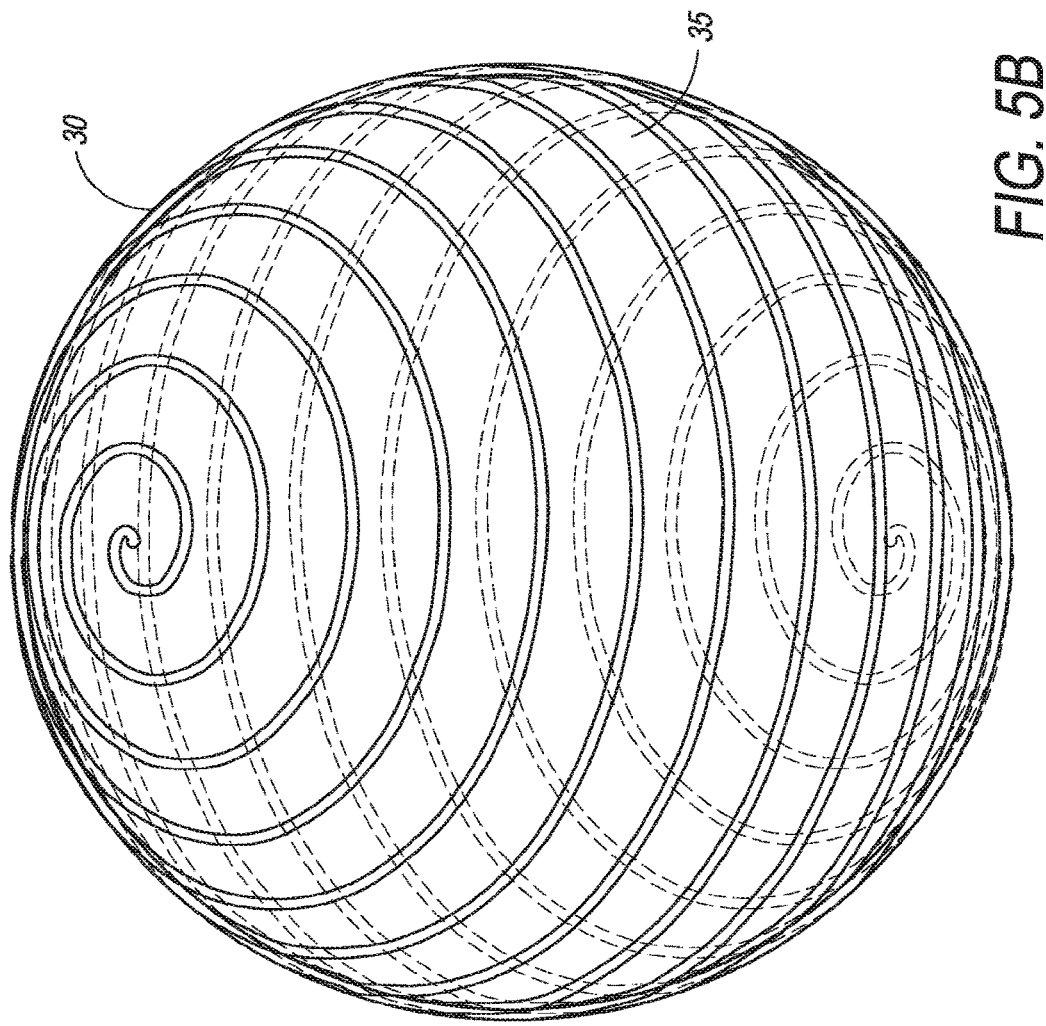
FIG. 5B is an illustration of the intragastric device of FIG. 5A in an exemplary post-deployment configuration.
Figure 5A:
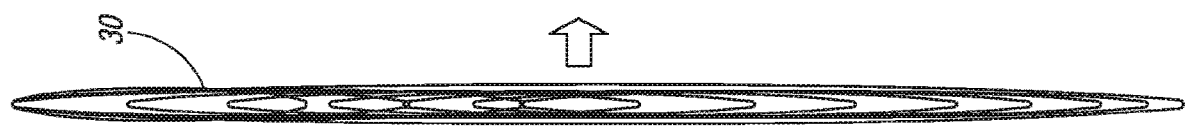
FIG. 5A is an illustration of another embodiment of the intragastric device in an exemplary pre-deployment configuration.

FIG. 5A is an illustration of another embodiment of the intragastric device 30 in an exemplary pre-deployment configuration. The pre-deployment configuration takes a compressed, cylindrical shape to facilitate insertion.

FIG. 5B is an illustration of the intragastric device 30 of FIG. 5A in an exemplary post-deployment configuration. The post-deployment configuration takes an expanded, spiral shape to occupy gastric volume and permit the sequestering of food within the device. In one embodiment, the spiral structure is covered with a membrane 35 containing openings of same or different sizes. In one embodiment, the openings have valves to direct the flow of food preferentially in an inward or an outward direction.

Figure 5D:
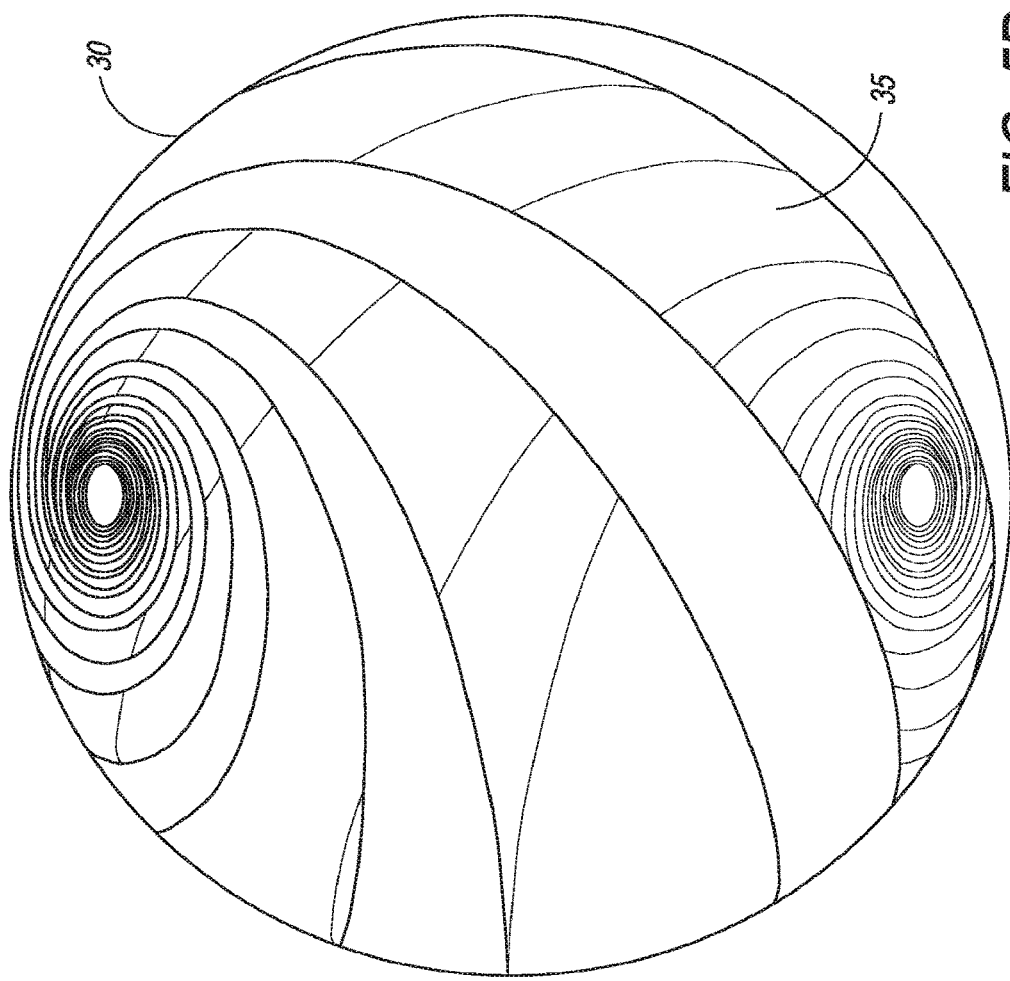
FIG. 5D is an illustration of the intragastric device of FIG. 5C in an exemplary post-deployment configuration.
Figure 5C:
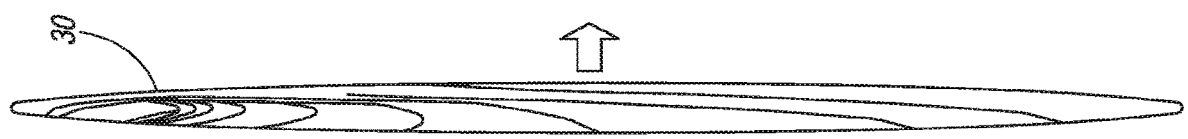
FIG. 5C is an illustration of yet another embodiment of the intragastric device in an exemplary pre-deployment configuration.

FIG. 5C is an illustration of yet another embodiment of the intragastric device 30 in an exemplary pre-deployment configuration. The pre-deployment configuration takes a compressed, cylindrical shape to facilitate insertion.

FIG. 5D is an illustration of the intragastric device 30 of FIG. 5C in an exemplary post-deployment configuration. The post-deployment configuration takes an expanded, spiral shape to occupy gastric volume and permit the sequestering of food within the device. In one embodiment, the spiral structure is covered with a membrane 35 containing openings of same or different sizes. In one embodiment, the openings have valves to direct the flow of food preferentially in an inward or an outward direction.

Figure 5F:
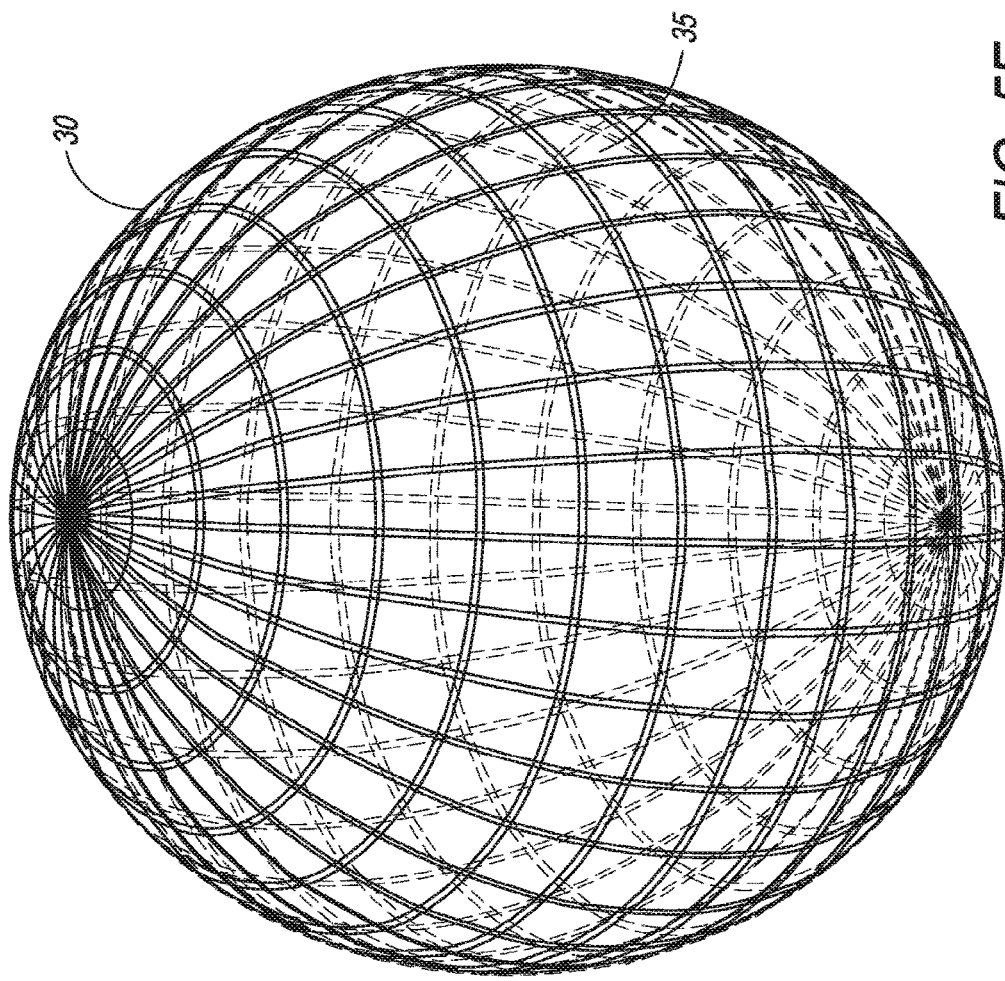
FIG. 5F is an illustration of the intragastric device of FIG. 5E in an exemplary post-deployment configuration.
Figure 5E:
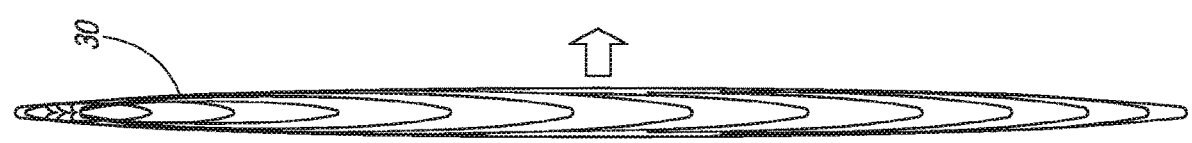
FIG. 5E is an illustration of yet another embodiment of the intragastric device in an exemplary pre-deployment configuration.

FIG. 5E is an illustration of yet another embodiment of the intragastric device 30 in an exemplary pre-deployment configuration. The pre-deployment configuration takes a compressed, cylindrical shape to facilitate insertion.

FIG. 5F is an illustration of the intragastric device 30 of FIG. 5C in an exemplary post-deployment configuration. The post-deployment configuration takes an expanded, wire mesh shape to occupy gastric volume and permit the sequestering of food within the device. In one embodiment, the wire mesh structure is covered with a membrane 35 containing openings of same or different sizes. In one embodiment, the openings have valves to direct the flow of food preferentially in an inward or an outward direction.

Figure 5G:
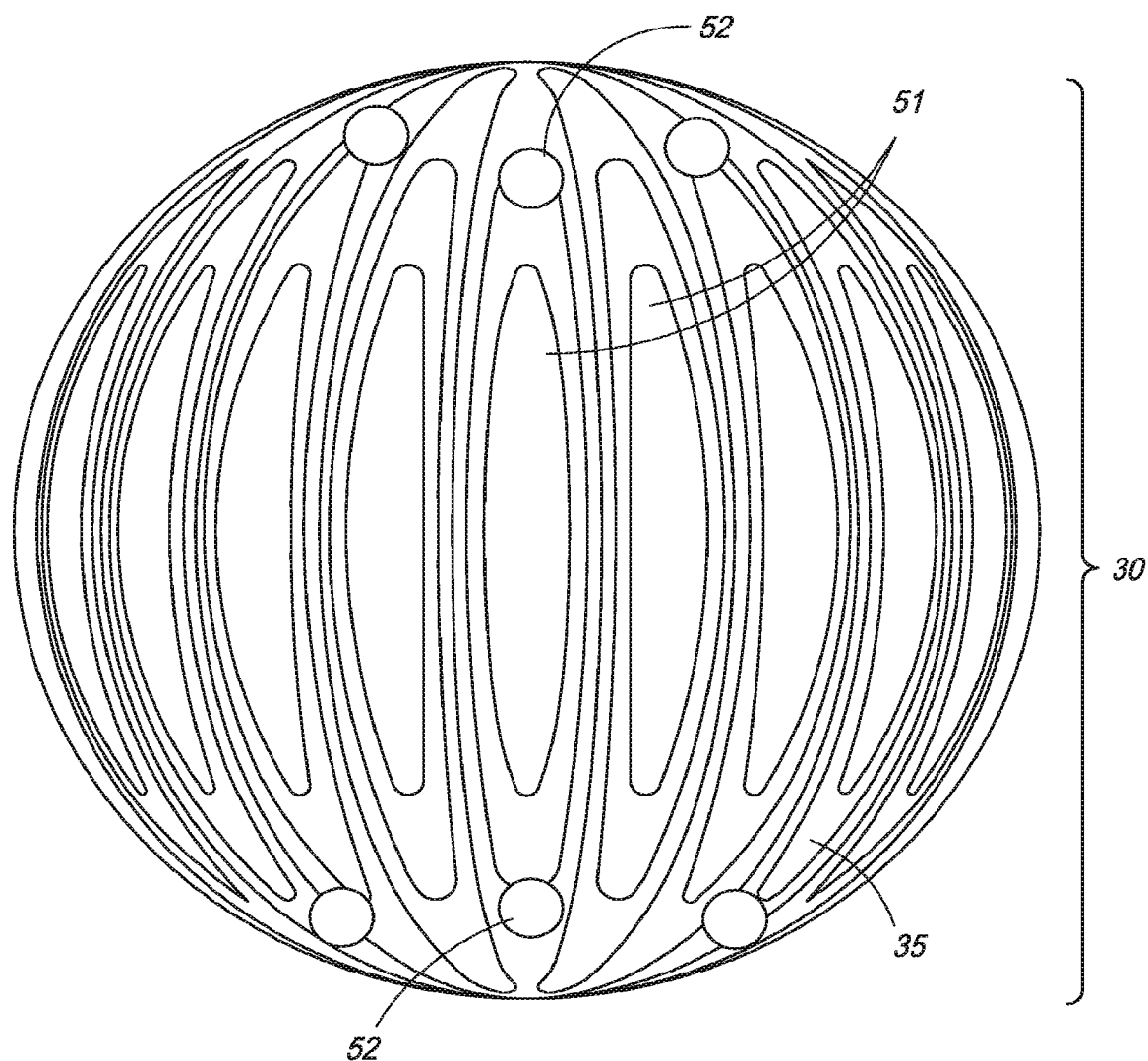
FIG. 5G is an illustration of one embodiment depicting an exemplary post-deployment membrane covered intragastric device with varying sized holes along its surface.

FIG. 5G is an illustration of one embodiment depicting an exemplary post-deployment, membrane 35 covered intragastric device 30 with varying sized openings along its surface. The middle two-thirds of the device 30 contain larger holes 51 and the top and bottom one-third contain smaller holes 52. In one embodiment, the larger holes 51 have valves composed of the same membranous material to direct the flow of food preferentially into the device 30. Thereafter, food slowly exits the device 30 through the smaller holes 52 positioned at the top and bottom of the device 30, thereby delaying gastric emptying.

FIG. 6 is an illustration of one embodiment depicting a possible configuration of the intragastric device 30 post-deployment. In this embodiment, the intragastric device takes the shape of a sphere.

FIG. 6A is an illustration of one embodiment depicting another possible configuration of the intragastric device 30 post-deployment. In this embodiment, the intragastric device 30 takes the shape of a kidney bean.

FIG. 6B is an illustration of one embodiment depicting another possible configuration of the intragastric device 30 post-deployment. In this embodiment, the intragastric device 30 takes the shape of an oval.

FIG. 6C is an illustration of one embodiment depicting another possible configuration of the intragastric device 30 post-deployment. In this embodiment, the intragastric device 30 takes the shape of a boot, with the lower, toe shaped portion positioned proximate to the pylorus.

FIG. 6D is an illustration of one embodiment depicting another possible configuration of the intragastric device 30 post-deployment. In this embodiment, the intragastric device 30 takes the shape of an inverted egg.

Figure 7:
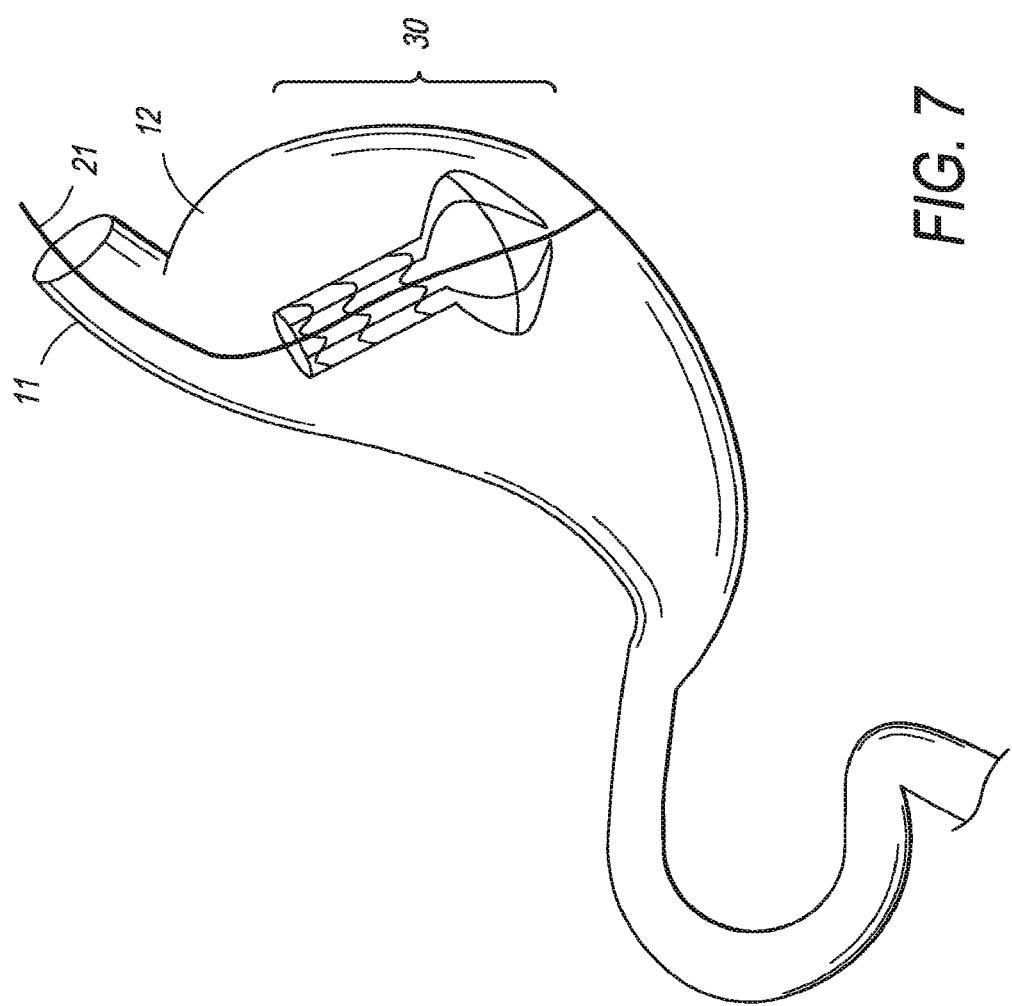
FIG. 7 is an illustration of one embodiment of an intragastric device being deployed in the stomach.

FIG. 7 is an illustration of the intragastric device 30 being deployed in the stomach 12. The catheter 21 used to deliver the intragastric device 30 is depicted as it traverses the esophagus 11. The partially deployed device 30 is shown in the stomach 12.

Figure 8:
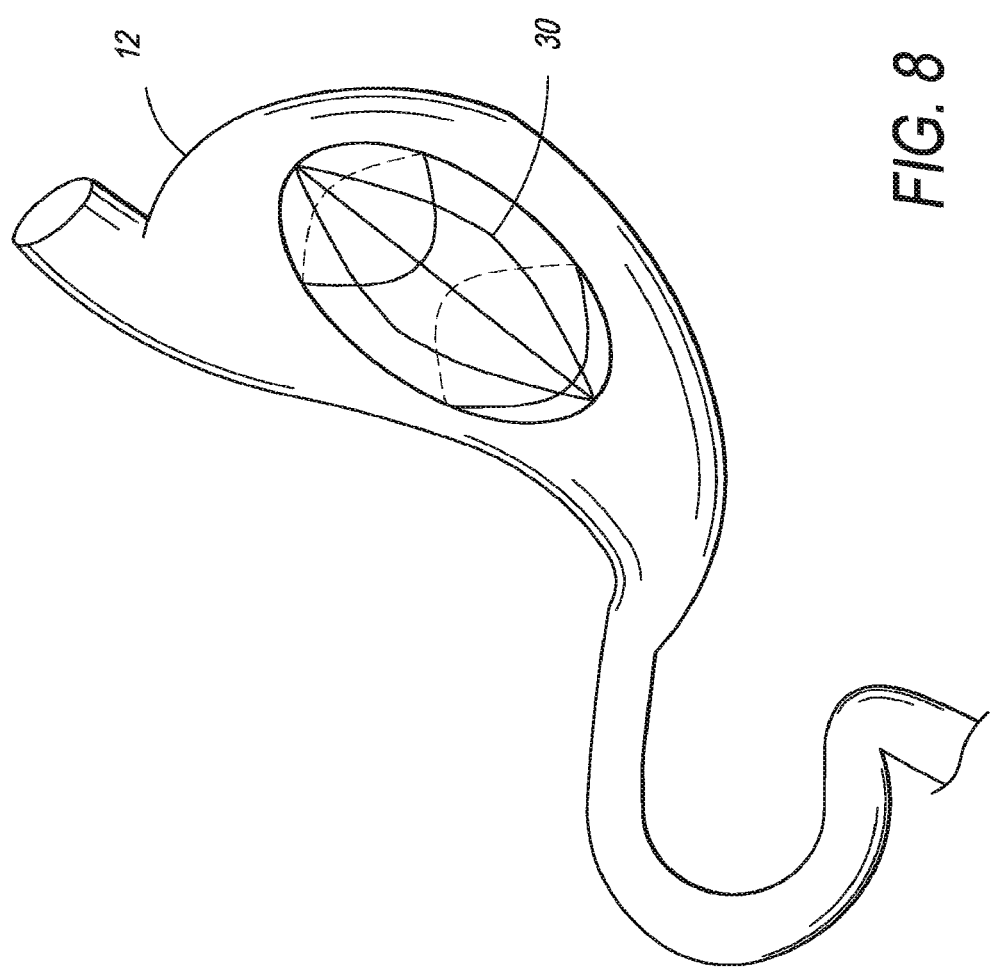
FIG. 8 is an illustration of one embodiment of a fully deployed intragastric device in the stomach.

FIG. 8 is an illustration of the fully deployed intragastric device 30 in the stomach 12. The intragastric device 30 occupies a significant portion of the stomach 12, thereby limiting the available volume to accommodate ingested food. The catheter used for delivery has been removed.

Figure 9:
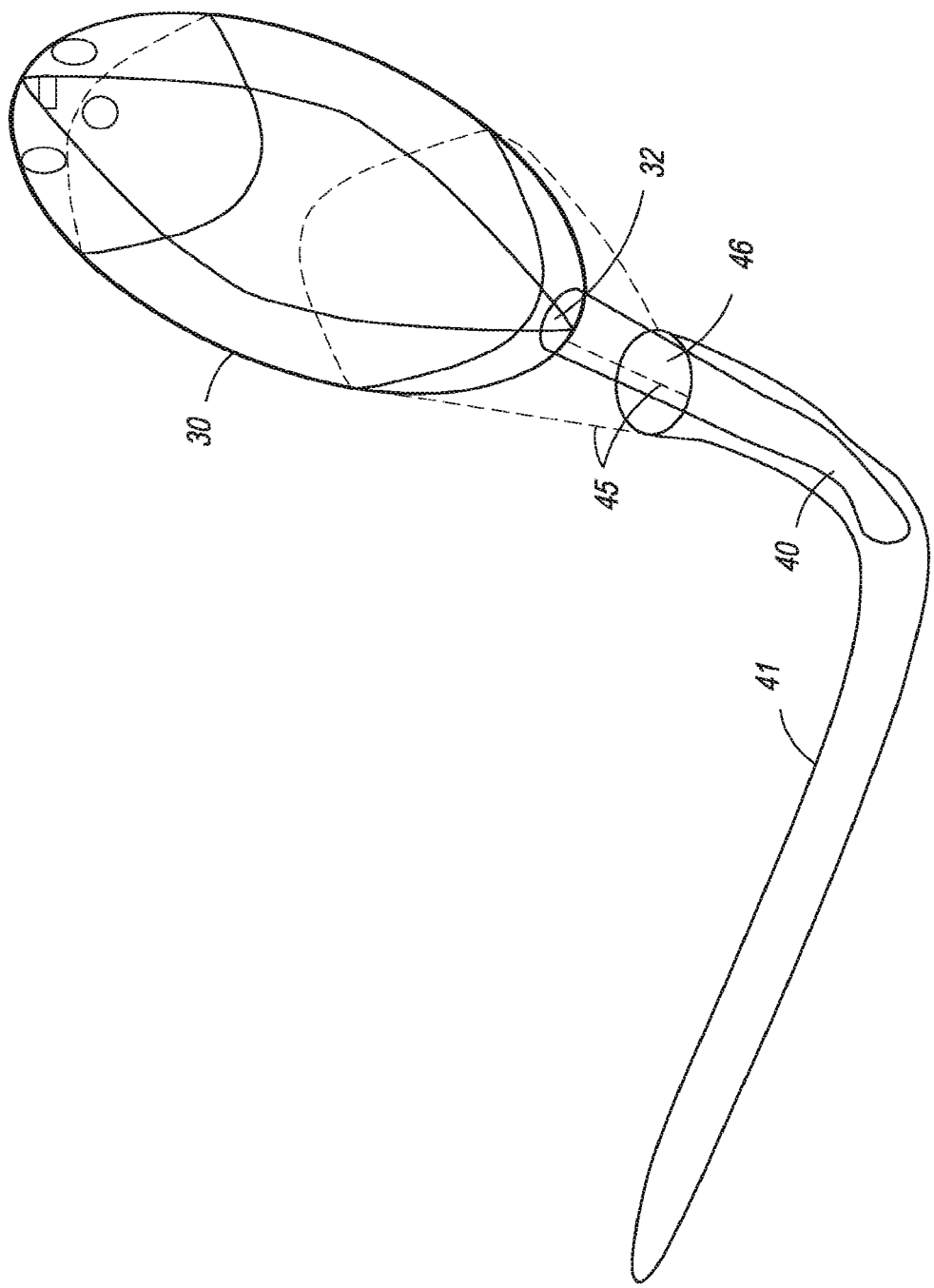
FIG. 9 is an illustration of one embodiment of an intragastric device with an attached sleeve.

FIG. 9 is an illustration of the intragastric device 30 with an attached sleeve 40. The top end of the sleeve 40 is attached to the bottom of the intragastric device 30. The top end of the sleeve 40 completely covers, encases, or otherwise envelopes the bottom holes 32 of the intragastric device 30 so that all chyme released from the intragastric device 30 will enter only into the sleeve 40. A second sleeve 41 is attached to the intragastric device 30 using wires, sutures or strings 45 and the opening 46 of this sleeve resides in the proximal duodenum to capture any food that does not enter the intragastric device 30 but passes alongside the intragastric device through the pylorus into the duodenum.

Figure 9A:
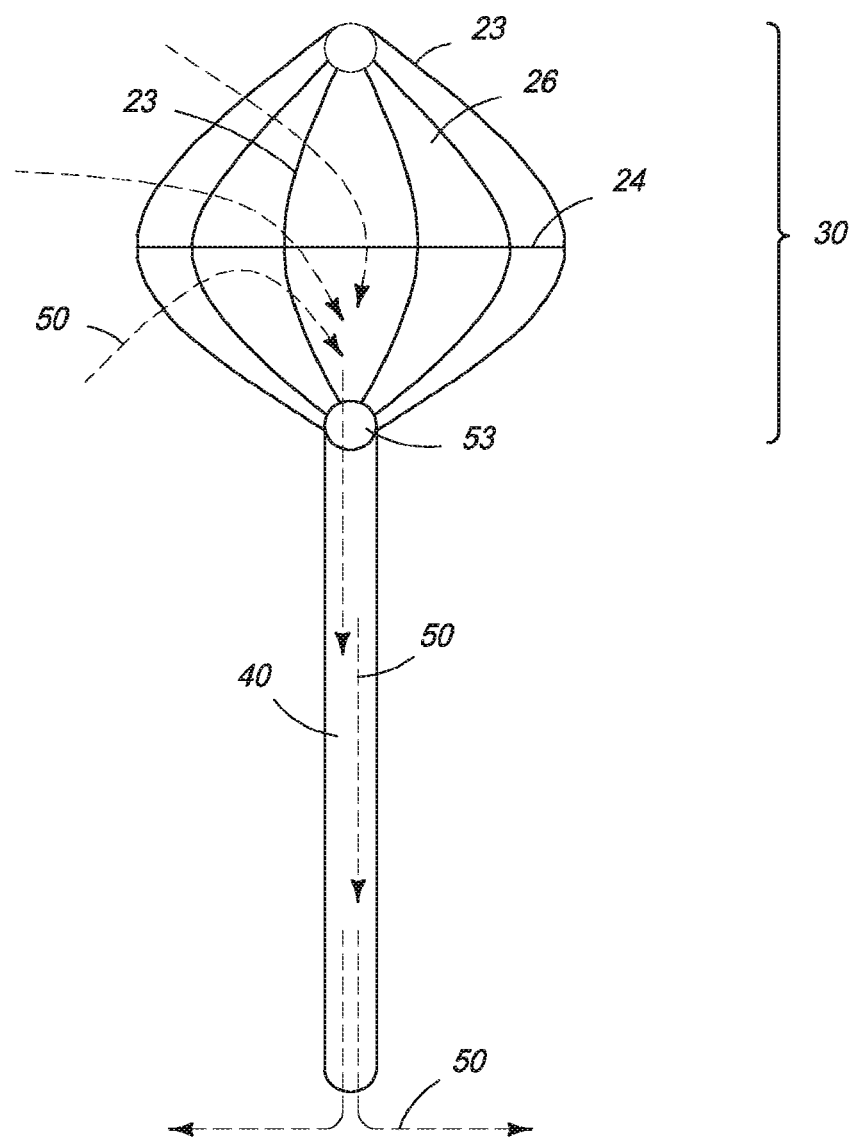
FIG. 9A is an illustration of one embodiment of an intragastric device with an attached sleeve in an exemplary post-deployment configuration.

FIG. 9A is an illustration of one embodiment of an intragastric device 30 with an attached sleeve 40 in an exemplary post-deployment configuration. The vertical members 23 and horizontal members 24 of the wire mesh structure are depicted in their expanded post-deployment configuration. In one embodiment, the device 30 is covered by a membrane 26 containing openings to permit entry of food into the device 30. In one embodiment, the openings have valves to direct the flow of food into the device 30. Once the device is fully deployed into a patient's upper gastrointestinal tract, food 50 passes into the device 30 through the openings located in the membrane 26. The food 50 is sequestered in the device 30 and slowly exits through the bottom of the device 30 through the opening 53 and into an attached sleeve 40. The food 50 travels along the length of the sleeve 40 and is deposited directly into the jejunum, completely bypassing the pylorus, duodenum, and ampulla of water.

Figure 9C:
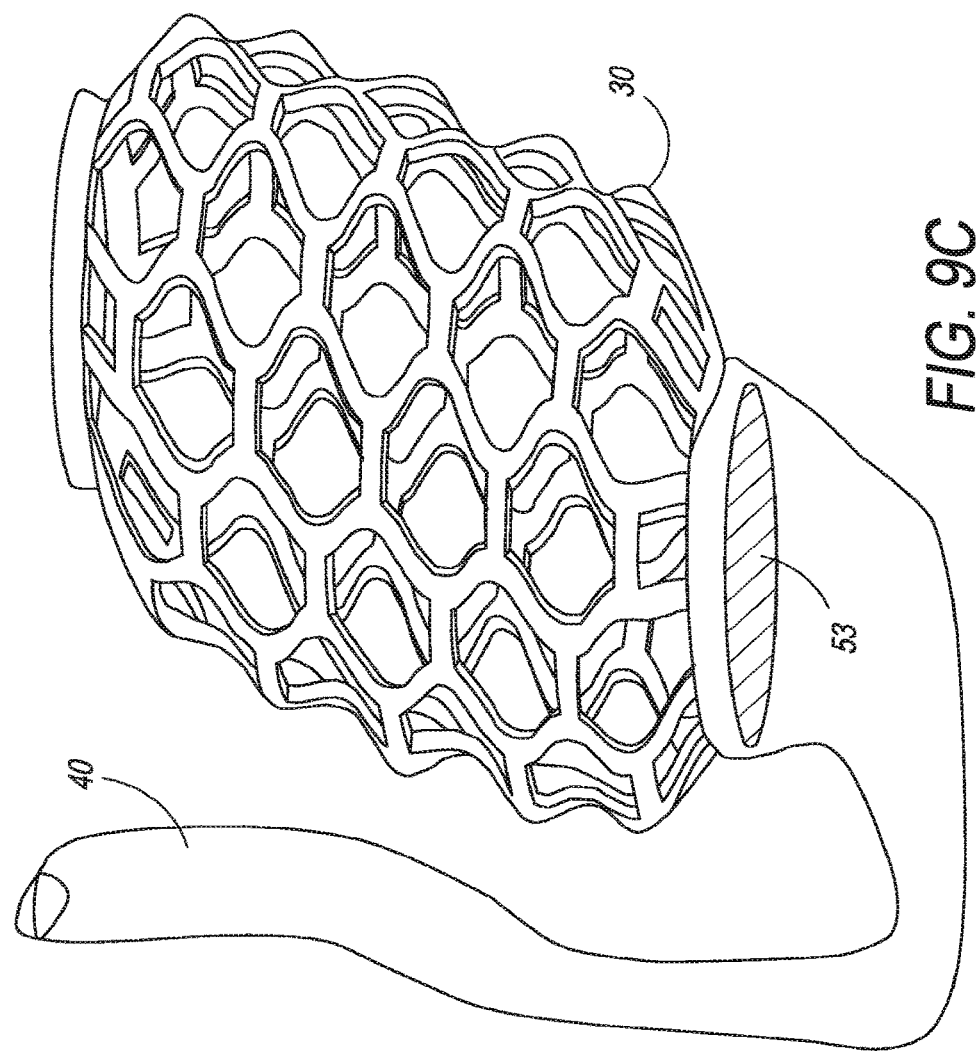
FIG. 9C is an illustration of the intragastric device with an attached sleeve of FIG. 9B in an exemplary post-deployment configuration.
Figure 9B:
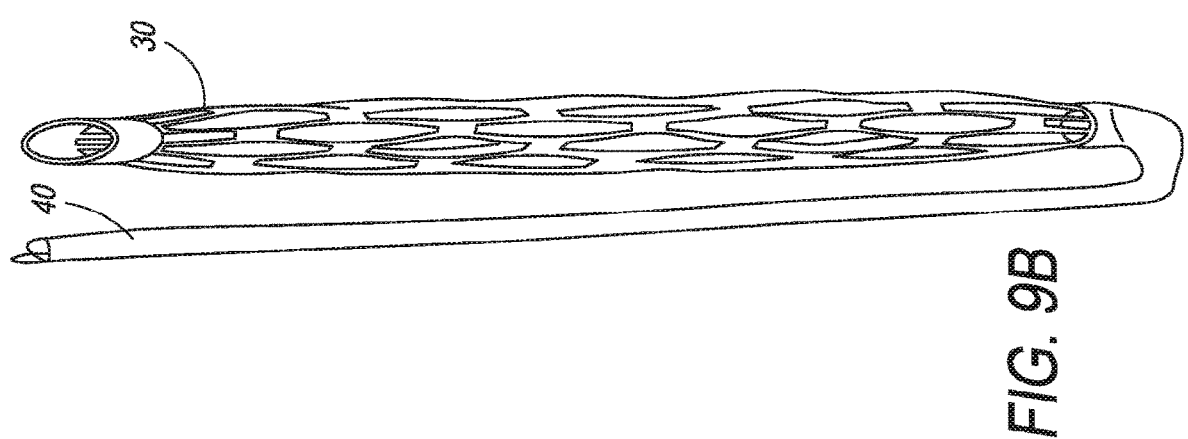
FIG. 9B is an illustration of another embodiment of the intragastric device with an attached sleeve in an exemplary pre-deployment configuration.

FIG. 9B is an illustration of another embodiment of the intragastric device 30 with an attached sleeve 40 in an exemplary pre-deployment configuration. The pre-deployment configuration takes a compressed, cylindrical shape to facilitate insertion.

FIG. 9C is an illustration of the intragastric device 30 with an attached sleeve 40 of FIG. 9B in an exemplary post-deployment configuration. The post-deployment configuration takes an expanded, honeycomb shape to occupy gastric volume and permit the sequestering of food within the device. In one embodiment, the honeycomb shaped device is covered with a membrane containing openings of the same or different sizes. In one embodiment, the openings have valves composed of the same membranous material to direct the flow of food preferentially into the device. In one embodiment, the device 30 contains one large opening 53 at the bottom that is wholly covered by the attached sleeve 40. The opening 53 at the bottom of the device 30 allows for the preferential passage of food into the sleeve 40 which in turn delivers the food into the jejunum.

Figure 10:
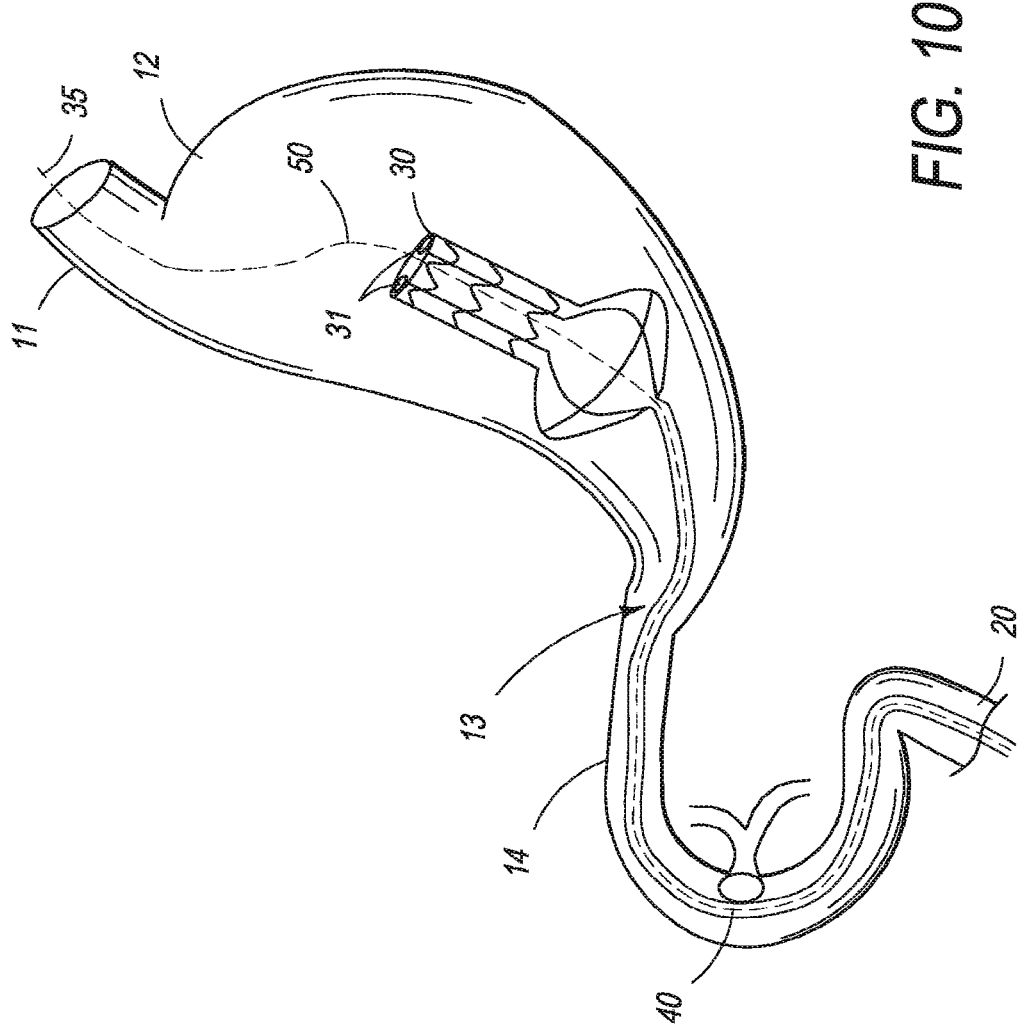
FIG. 10 is an illustration of one embodiment of an intragastric device with an attached sleeve being deployed in the upper gastrointestinal tract.

FIG. 10 is an illustration of the intragastric device 30 with an attached sleeve 40 being deployed over a guidewire 35 in the gastrointestinal tract. The intragastric device 30 is depicted in the stomach 12. The attached sleeve 40 is depicted traveling through the bottom portion of the stomach 12, passing through the pylorus 13 and duodenum 14, and ending and opening up into the jejunum 20. Food 50 passes through the esophagus 11 and into the stomach 12. There it enters the intragastric device 30 through the holes 31 proximate to the top of the intragastric device 30. The food 50 then travels from the intragastric device 30 through the sleeve 40 and into the middle portion of the jejunum 20 without being exposed to the duodenum 14 and proximal jejunum 20.

Figure 11:
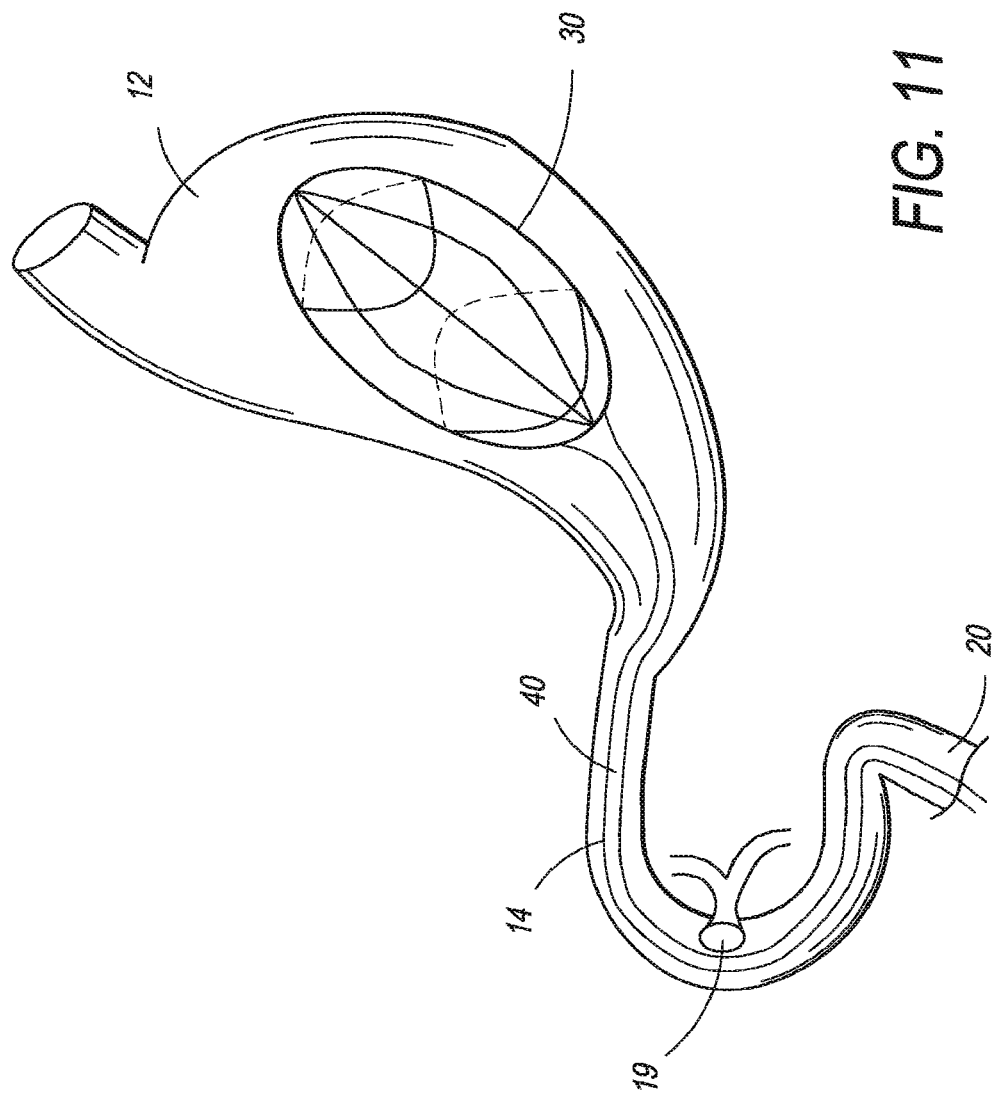
FIG. 11 is an illustration of one embodiment of a fully deployed intragastric device with an attached sleeve in the upper gastrointestinal tract.

FIG. 11 is an illustration of the fully deployed intragastric device with an attached sleeve 40 in the gastrointestinal tract. The intragastric device 30 occupies a significant portion of the stomach 12, thereby limiting the available volume to accommodate ingested food. The sleeve 40 is depicted traveling through the duodenum 14 and into the jejunum 20, bypassing the duodenum 14 and ampulla of water 19.

Figure 12:
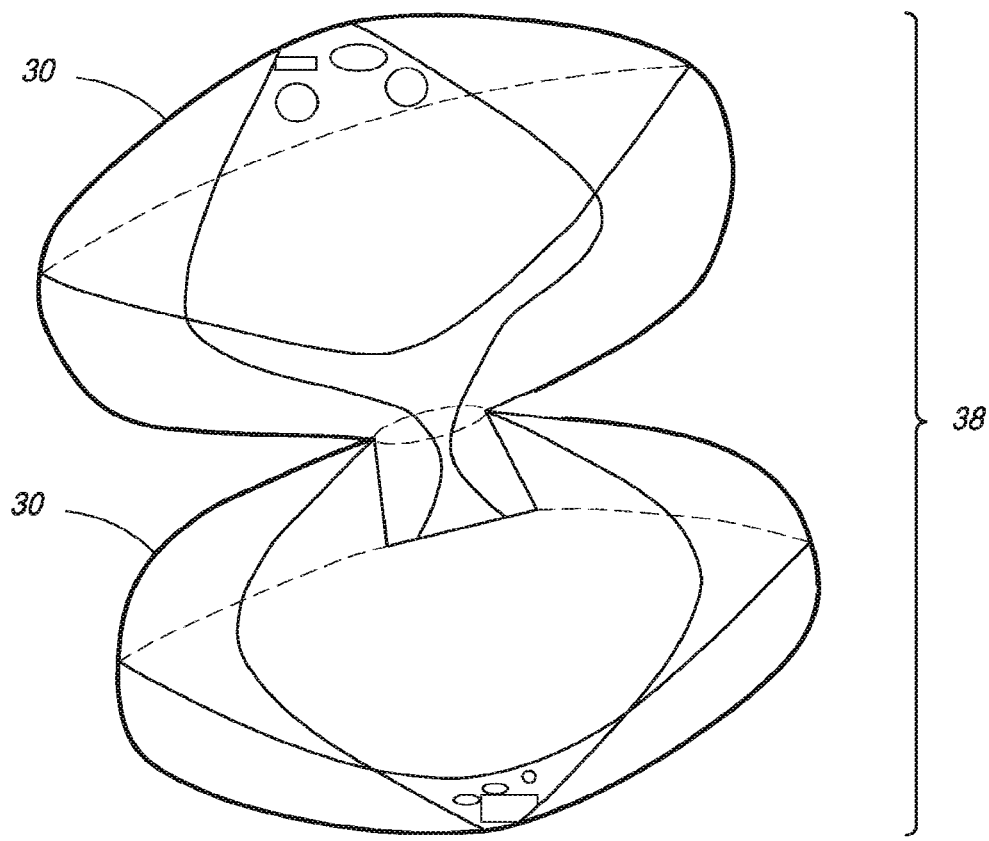
FIG. 12 is an illustration of two single exemplary intragastric devices linked together to form a combined intragastric device.

FIG. 12 is an illustration of two single intragastric devices 30 linked together to form a combined intragastric device 38. The combined intragastric device 38 occupies a greater volume than one single intragastric device 30, thereby inducing satiety even more quickly. The two single intragastric devices 30 are connected, one on top of the other, in such a fashion that food first passes through the large holes 31 in the top of the combined intragastric device 38 and is sequestered in the top single intragastric device 30. The food then slowly passes into, and is sequestered in the bottom of, the single intragastric device 30. Finally, the food slowly releases through the small holes 32 in the bottom of the combined intragastric structure 38 back into the stomach. This double intragastric device configuration acts to further delay gastric emptying, prolonging the sensation of satiety in the patient.

Figure 13:
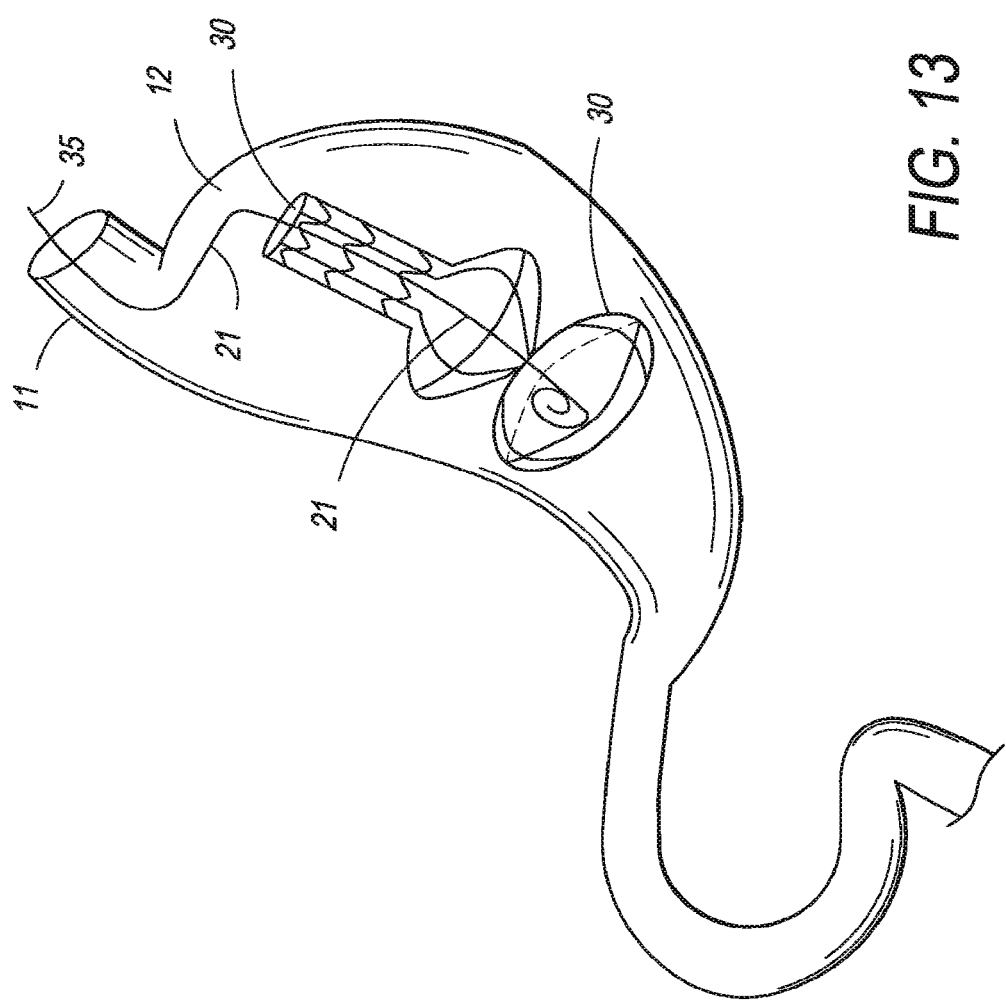
FIG. 13 is an illustration of one single exemplary intragastric device being attached to a previously deployed single intragastric device in the stomach.

FIG. 13 is an illustration of one single intragastric device 30 being passed over a guidewire 35 and attached to a previously deployed single intragastric device 30 in the stomach 12. The catheter 21 is depicted passing through the esophagus 11 and into the stomach 12. The catheter 21 is deploying the second single intragastric device 30 and assisting in its attachment to the previously deployed intragastric device 30. Operationally, the catheter will be passed into an opening of the existing intragastric device, preferably the opening used by the original catheter to deploy the device. The second device is then deployed with a portion of the second device, such as a neck, protrusion, or other member, fixedly attached to the first device, thereby anchoring the two devices together.

FIG. 14 is an illustration of a fully deployed combined intragastric device 38 in the stomach 12. The two single intragastric devices 30 are depicted attached one on top of the other, occupying a greater stomach 12 volume than one single intragastric device 30.

Figure 15A:
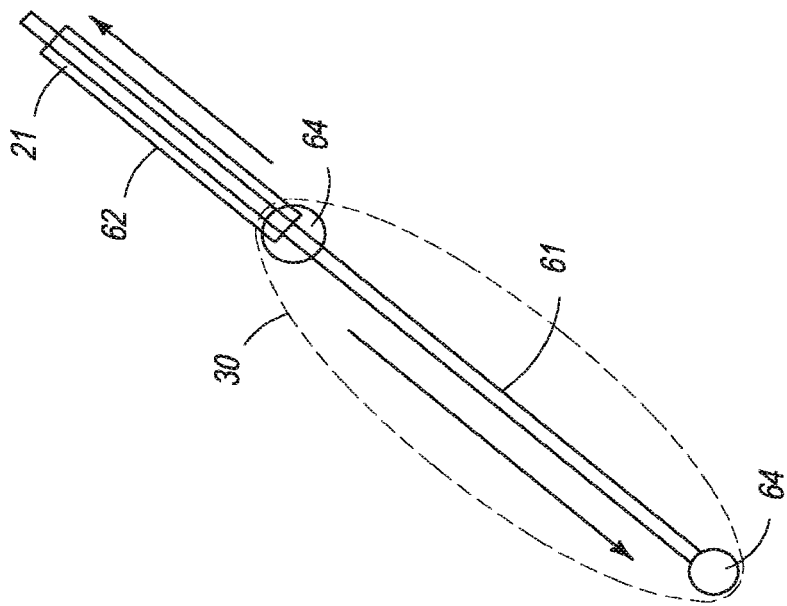
FIG. 15A is an illustration of a gastric device removal catheter attached to an intragastric device in an exemplary pre-deployment configuration.
Figure 15:
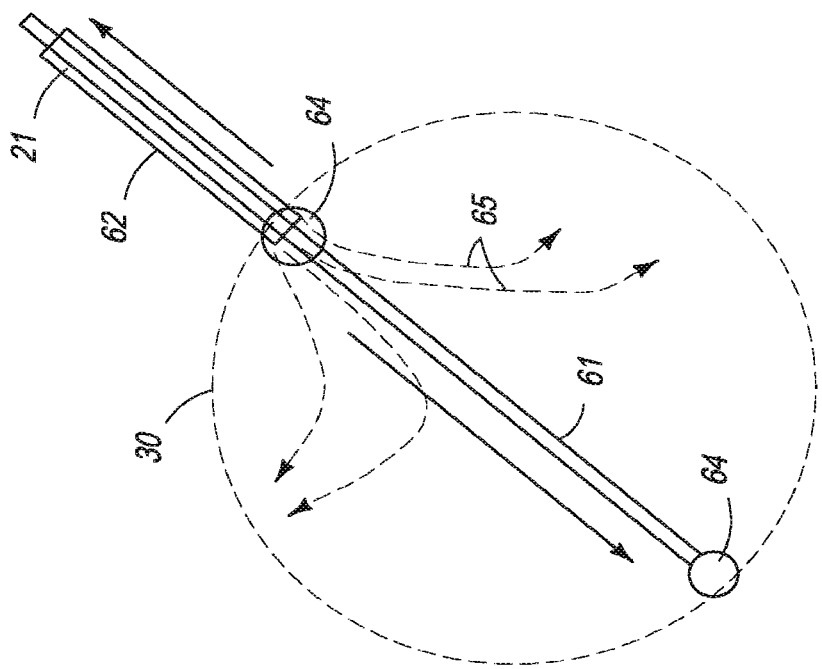
FIG. 15 is an illustration of a gastric device removal catheter attached to an intragastric device in an exemplary post-deployment configuration.

FIG. 15 is an illustration of a gastric device removal catheter 21 attached to an intragastric device 30 in an exemplary post-deployment configuration. The intragastric device 30 is depicted in its expanded, spherical shape. A coaxial catheter 21 is passed through the openings in the gastric device 30 and the walls of the device 30 are engaged by the expanded ends 64 of the catheter 21. The inner catheter 61 and outer catheter 62 are moved in opposite directions resulting in mechanical constriction of the device 30 to its predominantly linear pre-deployment configuration. In one embodiment, cold fluid 65 is instilled into the device 30 via the catheter 21 to lower the temperature of the shape memory structure and assist in further constriction of the device 30 to its predominantly linear pre-deployment structure.

FIG. 15A is an illustration of a gastric device removal catheter 21 attached to an intragastric device 30 in an exemplary pre-deployment configuration. The intragastric device 30 is depicted in its constricted, linear shape after constriction of the shape memory structure via use of the attached gastric device removal catheter 21. The expanded ends 64 of the catheter are depicted engaged with the ends of the linear intragastric device 30. The inner catheter 61 and outer catheter 62 are depicted after having moved opposite one another in order to constrict the intragastric device 30. The constricted, linear pre-deployment configuration facilitates in the removal of the device 30 from a patient's gastric cavity.

FIG. 16 is an illustration of the intragastric device 30 being removed from the stomach 12. The catheter 21 is inserted through the esophagus 11 and attaches to the intragastric device 30 in the stomach 12. The catheter 21 is then used to introduce cold fluid into the intragastric device to lower the temperature of the intragastric device 30, causing the intragastric device 30 to return its shape back to its pre-deployment configuration. Additional mechanical force can be used to constrain the intragastric device 30. Once returned to its initial compressed cylindrical shape, the intragastric device 30 can be removed using the attached catheter 21.

Figure 17B:
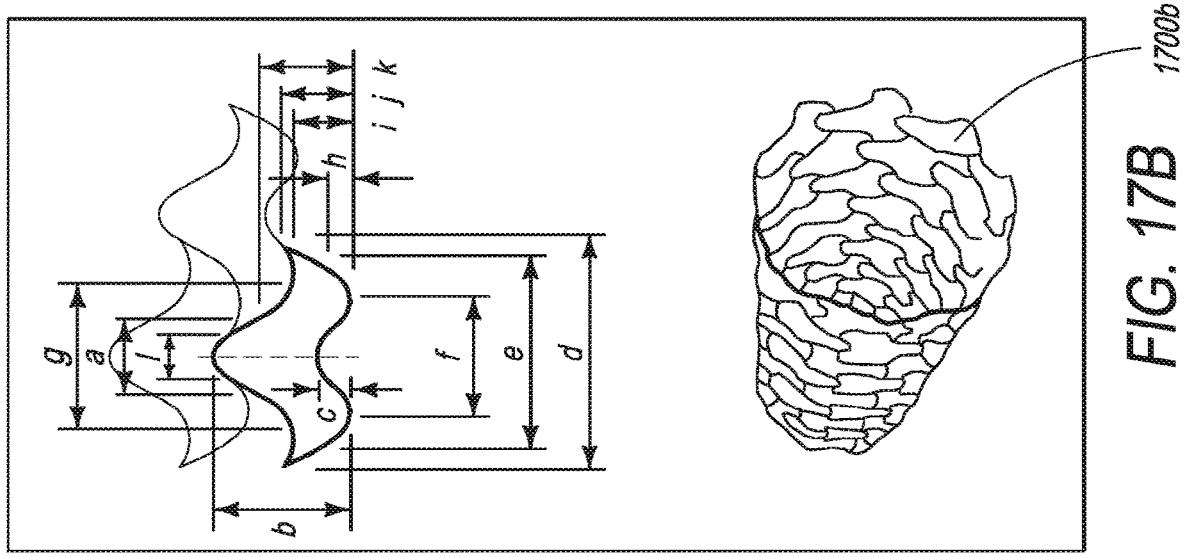
FIG. 17B is an illustration of one embodiment depicting a third exemplary configuration of the wire mesh structure.
Figure 17A:
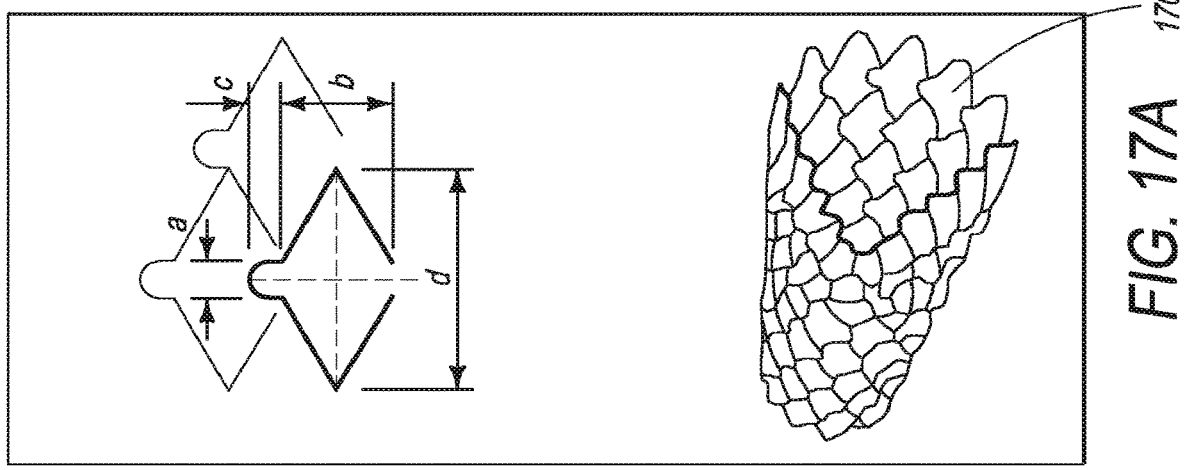
FIG. 17A is an illustration of one embodiment depicting a second exemplary configuration of the wire mesh structure.
Figure 17:
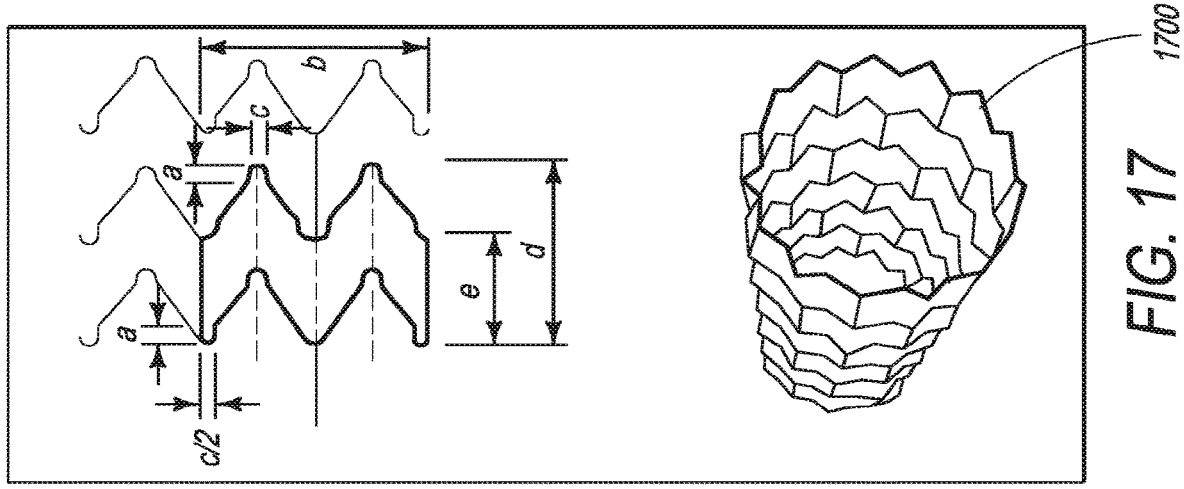
FIG. 17 is an illustration of one embodiment depicting a first exemplary configuration of the wire mesh structure.
Figure 17C:
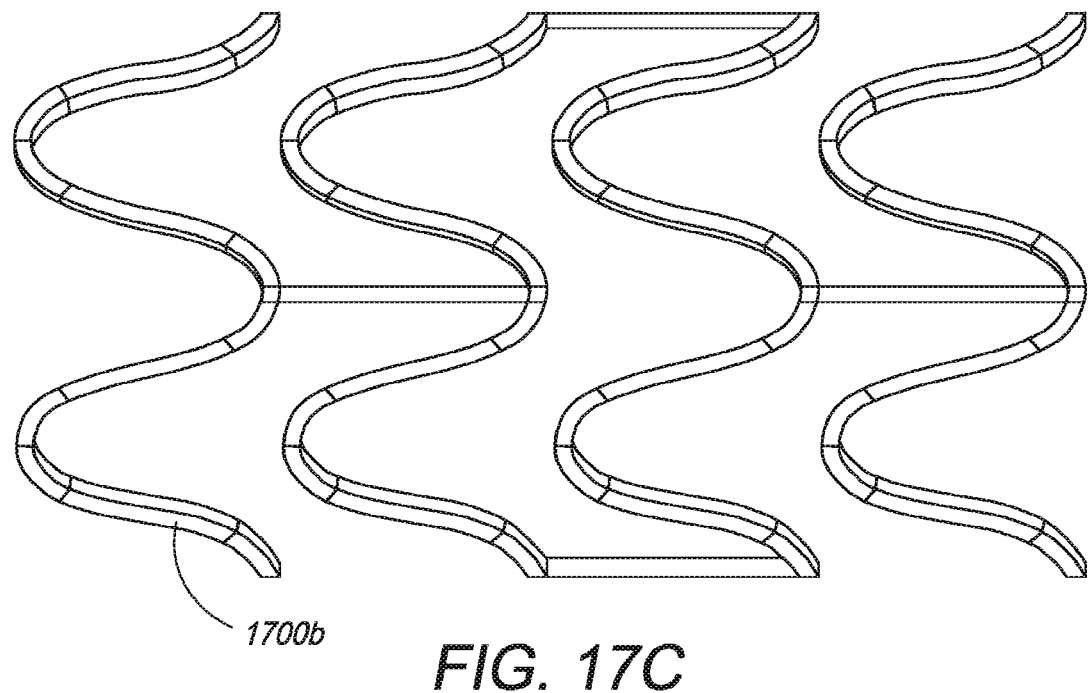
FIG. 17C is an illustration of one embodiment depicting a fourth exemplary configuration of the wire mesh structure.
Figure 17D:
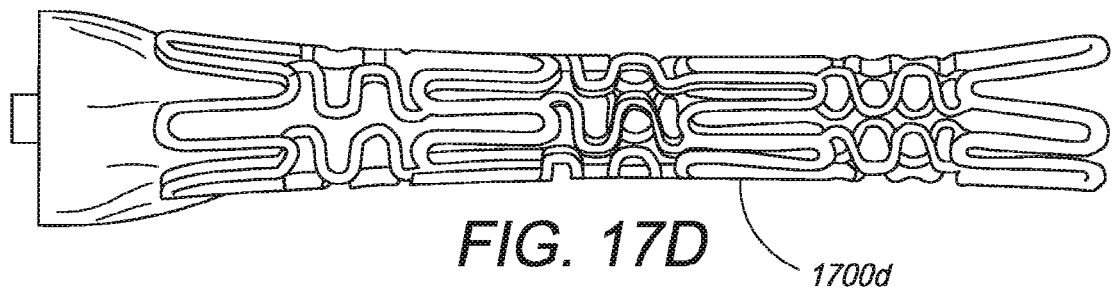
FIG. 17D is an illustration of one embodiment depicting a fifth exemplary configuration of the wire mesh structure.
Figure 17E:
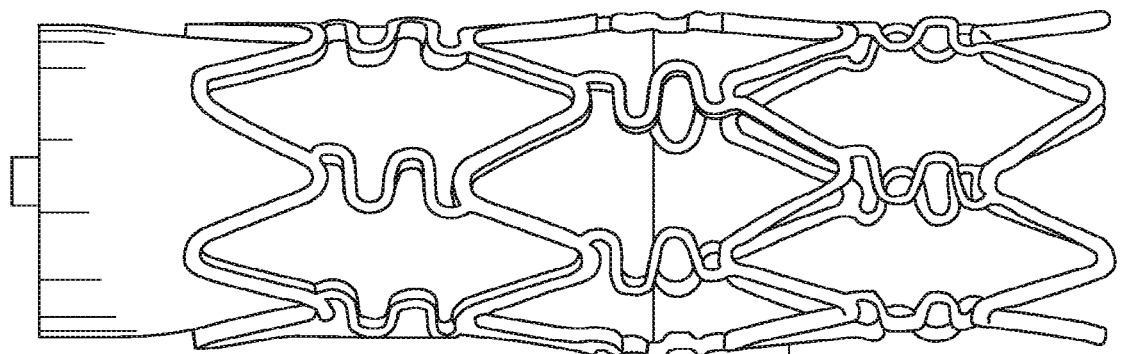
FIG. 17E is an illustration of one embodiment depicting the expanded configuration of the wire mesh structure of FIG. 17D.
Figure 17F:
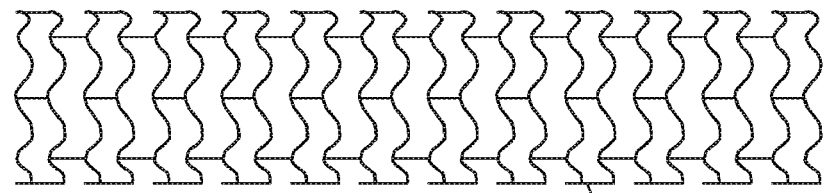
FIG. 17F is an illustration of one embodiment depicting a sixth exemplary configuration of the wire mesh structure.
Figure 17G:
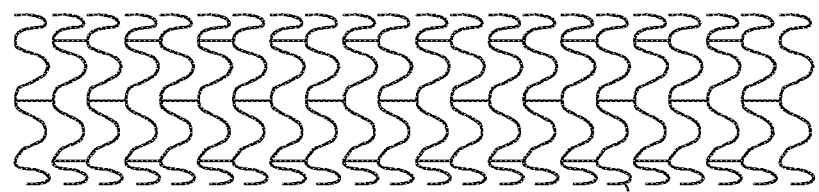
FIG. 17G is an illustration of one embodiment depicting a seventh exemplary configuration of the wire mesh structure.
Figure 17H:
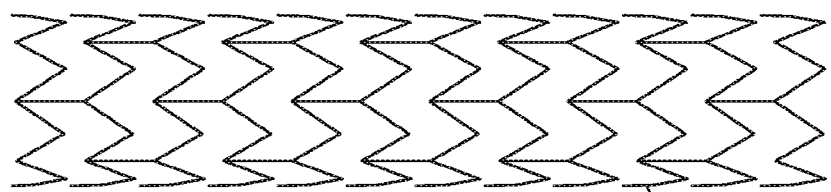
FIG. 17H is an illustration of one embodiment depicting an eighth exemplary configuration of the wire mesh structure.
Figure 17I:
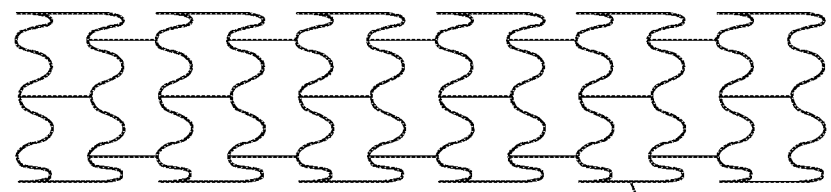
FIG. 17I is an illustration of one embodiment depicting a ninth exemplary configuration of the wire mesh structure.
Figure 17J:
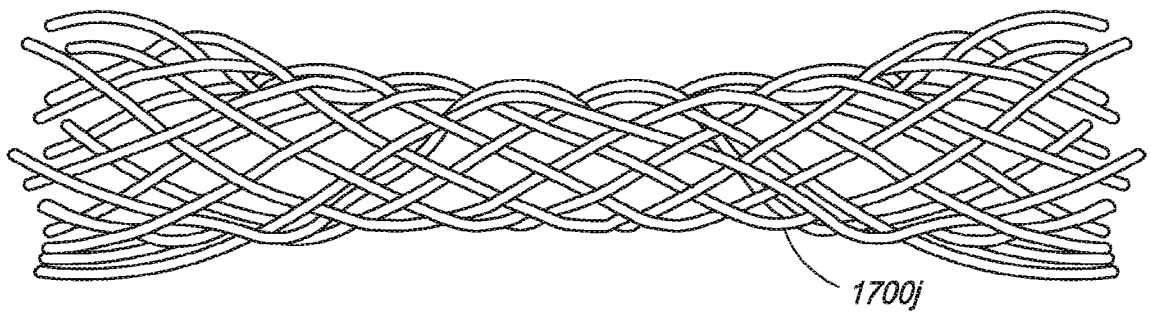
FIG. 17J is an illustration of one embodiment depicting a tenth exemplary configuration of the wire mesh structure; and, FIG. 17K is an illustration of one embodiment depicting an eleventh exemplary configuration of the wire mesh structure.
Figure 17K:
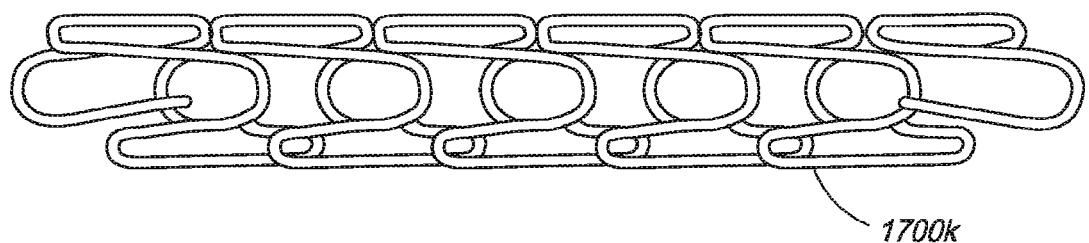

FIGS. 17 through 17K depict various exemplary configurations of the wire mesh structure, 1700, 1700a, 1700b, 1700c, 1700d, 1700e, 1700f, 1700g, 1700h, and 1700i, 1700j, and 1700k, comprised within the intragastric device. As shown in the Figures, the mesh structure can have a plurality of different configurations, with varying degrees of density between the wires components and varying sizes of holes defining the mesh structure. The spatial density may be defined in a plurality of dimensions, including along lengths and spaces a, b, c, d, e, f, g, h, i, j, and k.

It should be appreciated that the present disclosure is intended to provide a teaching of several exemplary embodiments of the present invention and is should not be limited to the specific structures disclosed herein. Other variations of the disclosed embodiments, which would be understood by those of ordinary skill, are covered by the present application and are within the scope of the invention, as further defined by the claims.

The invention claimed is:

1. An intragastric device having a top and a bottom comprising:
   a structure having a pre-deployment shape with a first volume and a post-deployment shape with a second volume, wherein said first volume is less than said second volume;
   wherein, in said post-deployment shape, said device comprises an upper volume near the top of the intragastric device and a plurality of first openings, each of said plurality of first openings defined by an area where a sum of the areas of the plurality of first openings is equal to a first area;
   wherein, in said post-deployment shape, said device comprises a lower volume near the bottom of the intragastric device and a plurality of second openings, each of said plurality of second openings defined by an area where a sum of the areas of the plurality of second openings is equal to a second area;
   wherein said first area is equal to or larger than said second area;
   wherein the structure is configured to be positioned within a stomach such that food is configured to enter the structure via the first openings, sequestered in the upper volume before passing into and sequestered in the lower volume, and released into the stomach via the second openings;
   wherein said structure is at least partially enveloped by a membrane that does not cover said first area or said second area; and
   wherein the structure is a porous structure configured to elastically expand to the post-deployment shape by changing from a pre-deployment compressed cylindrical shape to a post-deployment configuration of a predefined shape of significant volume.

2. The intragastric device according to claim 1, wherein the structure is a wire mesh.

3. The intragastric device according to claim 2, wherein the wire mesh structure is 90 to 99% covered by the membrane.

4. The intragastric device according to claim 2, wherein the membrane covering the wire mesh structure has more number of openings near the top of the structure and less number of openings near the bottom of the structure.

5. The intragastric device according to claim 1, wherein a sleeve is attached to the intragastric device and has a length sufficient to extend from the intragastric device into the jejunum.

6. The intragastric device according to claim 1, wherein a second intragastric device is attached to said intragastric device.

7. The intragastric device of claim 1, wherein the membrane comprises latex, parylene polyurethane, polytetrafluoroethylene (PTFE), fluorinated ethyleneprolylene, Dacron or polyethylene terephthalate (PET).

8. The intragastric device of claim 1, wherein the post-deployment configuration takes an expanded, spiral shape or an expanded wire mesh shape.

9. The intragastric device of claim 1, wherein the membrane contains openings of same or different sizes and the openings have valves to direct the flow of food preferentially in an inward or an outward direction.

10. The intragastric device of claim 1, wherein the intragastric device takes the post-deployment shape of a kidney bean.

11. The intragastric device of claim 1, wherein the intragastric device takes the post-deployment shape of an oval.

12. The intragastric device of claim 1, wherein the intragastric device takes the post-deployment shape of a boot with the lower toe shaped portion positioned proximate to the pylorus.

13. The intragastric device of claim 1, wherein the intragastric device takes the post-deployment shape of an inverted egg.

14. The intragastric device of claim 1, wherein the structure is a non-inflatable wire mesh structure.

15. The intragastric device of claim 1, wherein the structure is a spiral structure.

16. The intragastric device of claim 1, wherein the structure is made of shape memory metal.

17. The intragastric device of claim 1, wherein the structure is made of shape memory polymer.

18. An intragastric device having a top and a bottom comprising:
- a wire mesh structure having a pre-deployment shape with a first volume and a post-deployment shape with a second volume, wherein said first volume is less than said second volume;
- wherein, in said post-deployment shape, said device comprises a plurality of first openings, each of said plurality of first openings defined by an area where a sum of the areas of the plurality of first openings is equal to a first area;
- wherein, in said post-deployment shape, said device comprises a plurality of second openings, each of said plurality of second openings defined by an area where a sum of the areas of the plurality of second openings is equal to a second area;
- wherein said first area is equal to or larger than said second area;
- wherein said first area is closer to the top of said device relative to the second area;
- wherein said structure is at least partially enveloped by a membrane that does not cover said first area or said second area, the membrane having more number of openings near the top of the structure and less number of openings near the bottom of the structure; and
- wherein the structure is a porous structure configured to elastically expand to the post-deployment shape by changing from a pre-deployment compressed cylindrical shape to a post-deployment configuration of a predefined shape of significant volume.

19. An intragastric device having a top and a bottom comprising:
- a structure having a pre-deployment shape with a first volume and a post-deployment shape with a second volume, wherein said first volume is less than said second volume;
- wherein, in said post-deployment shape, said device comprises a plurality of first openings, each of said plurality of first openings defined by an area where a sum of the areas of the plurality of first openings is equal to a first area;
- wherein, in said post-deployment shape, said device comprises a plurality of second openings, each of said plurality of second openings defined by an area where a sum of the areas of the plurality of second openings is equal to a second area;
- wherein said first area is equal to or larger than said second area;
- wherein said first area is closer to the top of said device relative to the second area;
- wherein said structure is at least partially enveloped by a membrane that does not cover said first area or said second area, the membrane contains openings of same or different sizes, and the openings have valves to direct the flow of food preferentially in an inward or an outward direction; and
- wherein the structure is a porous structure configured to elastically expand to the post-deployment shape by changing from a pre-deployment compressed cylindrical shape to facilitate insertion to a post-deployment configuration of a predefined shape of significant volume.

* * * * *